(12) United States Patent
Toth et al.

(10) Patent No.: US 12,053,634 B2
(45) Date of Patent: *Aug. 6, 2024

(54) ENDOSCOPIC SYMPATHECTOMY SYSTEMS AND METHODS

(71) Applicant: Autonomix Medical, Inc., Ivyland, PA (US)

(72) Inventors: Landy Toth, Doylestown, PA (US); Robert Schwartz, Inver Grove Heights, MN (US)

(73) Assignee: Autonomix Medical, Inc., Ivyland, PA (US)

( * ) Notice: Subject to any disclaimer, the term of this patent is extended or adjusted under 35 U.S.C. 154(b) by 182 days.

This patent is subject to a terminal disclaimer.

(21) Appl. No.: 17/732,716

(22) Filed: Apr. 29, 2022

(65) Prior Publication Data

US 2022/0249851 A1 Aug. 11, 2022

Related U.S. Application Data

(63) Continuation of application No. 16/252,207, filed on Jan. 18, 2019, now Pat. No. 11,344,731, which is a
(Continued)

(51) Int. Cl.
*A61B 5/00* (2006.01)
*A61B 5/02* (2006.01)
(Continued)

(52) U.S. Cl.
CPC ...... *A61N 1/37205* (2013.01); *A61B 5/02007* (2013.01); *A61B 5/0205* (2013.01);
(Continued)

(58) Field of Classification Search
CPC .... A61N 1/37205; A61N 1/05; A61N 1/0553; A61N 1/0556; A61N 7/02; A61B 5/02007; A61B 5/0205; A61B 5/1107; A61B 5/24; A61B 5/283; A61B 5/296; A61B 5/4839; A61B 5/4848; A61B 5/4875;
(Continued)

(56) References Cited

U.S. PATENT DOCUMENTS 4,402,311 A * 9/1983 Hattori ............... A61B 1/00097
600/117
4,602,624 A * 7/1986 Naples ................ A61N 1/0556
607/118
(Continued)

FOREIGN PATENT DOCUMENTS

AU 2010207062 B2 5/2015
AU 2014233285 A1 9/2015
(Continued)

*Primary Examiner* — May A Abouelela
(74) *Attorney, Agent, or Firm* — Ryan, Mason & Lewis, LLP

(57) ABSTRACT

A system for controlled sympathectomy procedures is disclosed. A system for controlled micro ablation procedures is disclosed. Methods for performing a controlled surgical procedure are disclosed. A system for performing controlled surgical procedures in a minimally invasive manner is disclosed. An implantable device for monitoring and/or performing a neuromodulation procedure is disclosed.

20 Claims, 10 Drawing Sheets

US 12,053,634 B2
Page 2

Related U.S. Application Data continuation of application No. 15/920,775, filed on Mar. 14, 2018, now Pat. No. 10,226,633, which is a continuation of application No. 14/403,891, filed as application No. PCT/US2013/042847 on May 28, 2013, now Pat. No. 9,968,790.

(60) Provisional application No. 61/652,426, filed on May 29, 2012.

(51) Int. Cl.

| | | |
|---|---|---|
| *A61B 5/0205* | (2006.01) | |
| *A61B 5/11* | (2006.01) | |
| *A61B 5/24* | (2021.01) | |
| *A61B 5/283* | (2021.01) | |
| *A61B 5/296* | (2021.01) | |
| *A61B 7/04* | (2006.01) | |
| *A61B 18/14* | (2006.01) | |
| *A61M 5/14* | (2006.01) | |
| *A61N 1/05* | (2006.01) | |
| *A61N 1/372* | (2006.01) | |
| *A61B 10/02* | (2006.01) | |
| *A61B 17/00* | (2006.01) | |
| *A61B 18/00* | (2006.01) | |
| *A61B 18/02* | (2006.01) | |
| *A61N 7/02* | (2006.01) | |

(52) U.S. Cl.
CPC ............. *A61B 5/1107* (2013.01); *A61B 5/24* (2021.01); *A61B 5/283* (2021.01); *A61B 5/296* (2021.01); *A61B 5/4839* (2013.01); *A61B 5/4848* (2013.01); *A61B 5/4875* (2013.01); *A61B 5/6852* (2013.01); *A61B 7/04* (2013.01); *A61B 18/1445* (2013.01); *A61B 18/1492* (2013.01); *A61M 5/14* (2013.01); *A61N 1/05* (2013.01); *A61B 10/02* (2013.01); *A61B 2017/00345* (2013.01); *A61B 2018/00291* (2013.01); *A61B 2018/00345* (2013.01); *A61B 2018/00434* (2013.01); *A61B 2018/00505* (2013.01); *A61B 2018/00511* (2013.01); *A61B 2018/00577* (2013.01); *A61B 2018/00642* (2013.01); *A61B 2018/00648* (2013.01); *A61B 2018/00755* (2013.01); *A61B 2018/00839* (2013.01); *A61B 2018/00875* (2013.01); *A61B 18/02* (2013.01); *A61B 2018/143* (2013.01); *A61B 2562/0214* (2013.01); *A61M 2202/0275* (2013.01); *A61M 2202/048* (2013.01); *A61M 2202/0484* (2013.01); *A61M 2202/049* (2013.01); *A61N 1/0553* (2013.01); *A61N 1/0556* (2013.01); *A61N 7/02* (2013.01)

(58) Field of Classification Search
CPC ..... A61B 5/6852; A61B 7/04; A61B 18/1445; A61B 18/1492; A61B 10/02; A61B 18/02; A61B 2017/00345; A61B 2018/00291; A61B 2018/00345; A61B 2018/00434; A61B 2018/00505; A61B 2018/00511; A61B 2018/00577; A61B 2018/00642; A61B 2018/00648; A61B 2018/00755; A61B 2018/00839; A61B 2018/00875; A61B 2018/143; A61B 2562/0214; A61M 5/14; A61M 2202/0275; A61M 2202/048; A61M 2202/0484; A61M 2202/049
See application file for complete search history.

(56) References Cited

U.S. PATENT DOCUMENTS

| | | | |
|---|---|---|---|
| 5,228,442 A | | 7/1993 | Imran |
| 5,419,312 A | * | 5/1995 | Arenberg ............... A61B 1/042 600/549 |
| 5,450,846 A | | 9/1995 | Goldreyer |
| 5,505,201 A | * | 4/1996 | Grill, Jr. .................. A61N 1/04 600/371 |
| 5,603,711 A | * | 2/1997 | Parins ................ A61B 18/1445 606/51 |
| 5,711,298 A | | 1/1998 | Littmann et al. |
| 5,762,626 A | * | 6/1998 | Lundquist .......... A61B 18/1477 604/22 |
| 5,800,350 A | * | 9/1998 | Coppleson ............ A61B 5/0059 600/382 |
| 5,808,665 A | * | 9/1998 | Green .................. H04N 13/337 348/E13.016 |
| 5,890,510 A | | 4/1999 | Mason |
| 5,980,510 A | * | 11/1999 | Tsonton ......... A61B 17/320092 606/171 |
| 6,246,912 B1 | | 6/2001 | Sluijter et al. |
| 6,277,089 B1 | * | 8/2001 | Yoon .................. A61B 17/4241 606/49 |
| 6,312,425 B1 | * | 11/2001 | Simpson ............ A61B 18/1492 606/41 |
| 6,371,926 B1 | * | 4/2002 | Thorson ................ A61B 18/14 600/549 |
| 6,466,817 B1 | | 10/2002 | Kaula et al. |
| 6,468,204 B2 | * | 10/2002 | Sendai ............... A61B 1/00009 600/118 |
| 6,692,490 B1 | | 2/2004 | Edwards |
| 6,810,281 B2 | * | 10/2004 | Brock ....................... A61B 5/24 600/407 |
| 7,177,677 B2 | | 2/2007 | Kaula et al. |
| 7,255,695 B2 | | 8/2007 | Falwell et al. |
| 7,455,666 B2 | | 11/2008 | Purdy |
| 7,753,908 B2 | * | 7/2010 | Swanson ............ A61B 18/1445 606/49 |
| 7,865,236 B2 | | 1/2011 | Cory et al. |
| 7,885,700 B2 | | 2/2011 | Clark et al. |
| 8,000,782 B2 | * | 8/2011 | Gharib ................ A61B 5/4893 607/117 |
| 8,005,536 B2 | * | 8/2011 | Imran ....................... A61B 5/11 600/587 |
| 8,034,050 B2 | * | 10/2011 | Sharareh .................. A61N 1/06 606/41 |
| 8,097,926 B2 | | 1/2012 | De Graff et al. |
| 8,320,990 B2 | | 11/2012 | Vij |
| 8,523,043 B2 | * | 9/2013 | Ullrich ................ A61B 17/072 227/19 |
| 8,536,667 B2 | | 9/2013 | De Graff et al. |
| 8,613,702 B2 | * | 12/2013 | Feer ........................ A61B 5/24 600/323 |
| 8,702,857 B2 | | 4/2014 | Venema et al. |
| 8,706,219 B2 | | 4/2014 | Feldman et al. |
| 8,712,549 B2 | | 4/2014 | Zdeblick et al. |
| 8,998,802 B2 | * | 4/2015 | Gono ........................ A61F 7/12 600/179 |
| 9,186,060 B2 | | 11/2015 | De Graff et al. |
| 9,295,842 B2 | | 3/2016 | Ghaffari et al. |
| 9,326,788 B2 | * | 5/2016 | Batross .................. A61B 34/30 |
| 9,326,816 B2 | | 5/2016 | Srivastava |
| 9,339,332 B2 | | 5/2016 | Srivastava |
| 9,629,586 B2 | | 4/2017 | Ghaffari et al. |
| 9,662,069 B2 | | 5/2017 | De Graff et al. |
| 9,750,421 B2 | | 9/2017 | Ghaffari et al. |
| 9,801,557 B2 | | 10/2017 | Ghaffari et al. |
| 9,820,673 B2 | | 11/2017 | Feldman et al. |
| 9,931,047 B2 | | 4/2018 | Srivastava |
| 10,186,546 B2 | | 1/2019 | De Graff et al. |
| 10,271,898 B2 | | 4/2019 | Cao et al. |
| 10,292,610 B2 | | 5/2019 | Srivastava |
| 10,426,545 B2 | | 10/2019 | Asirvatham et al. |
| 10,737,123 B2 | | 8/2020 | Sullivan et al. |
| 10,918,298 B2 | | 2/2021 | Rogers et al. |

(56) References Cited

U.S. PATENT DOCUMENTS

| | | | |
|---|---|---|---|
| 11,058,484 | B2 | 7/2021 | Asirvatham et al. |
| 11,515,029 | B2 | 11/2022 | Sullivan et al. |
| 11,540,775 | B2 | 1/2023 | Shachar et al. |
| 2001/0039415 | A1* | 11/2001 | Francischelli ......... A61B 5/411 600/549 |
| 2003/0014016 | A1 | 1/2003 | Purdy |
| 2003/0216792 | A1 | 11/2003 | Levin et al. |
| 2004/0260164 | A1* | 12/2004 | Kilcoyne ............ A61B 5/4233 600/350 |
| 2006/0015165 | A1* | 1/2006 | Bertolero ................ A61B 1/12 600/374 |
| 2006/0041277 | A1 | 2/2006 | Deem et al. |
| 2007/0118039 | A1 | 5/2007 | Bodecker et al. |
| 2007/0265620 | A1* | 11/2007 | Kraas ................ A61B 18/1442 606/51 |
| 2008/0269586 | A1* | 10/2008 | Rubinsky ............... A61B 18/12 606/50 |
| 2009/0005667 | A1 | 1/2009 | Cui et al. |
| 2009/0069808 | A1 | 3/2009 | Pike, Jr. et al. |
| 2010/0298895 | A1 | 11/2010 | Ghaffari et al. |
| 2011/0040347 | A1 | 2/2011 | Libbus et al. |
| 2011/0112569 | A1* | 5/2011 | Friedman ............... A61B 17/29 600/509 |
| 2011/0166482 | A1 | 7/2011 | Stack et al. |
| 2011/0270121 | A1* | 11/2011 | Johnson ................. A61B 17/29 606/51 |
| 2011/0306851 | A1 | 12/2011 | Wang |
| 2011/0306974 | A1* | 12/2011 | Swanson ............ A61B 18/1492 606/52 |
| 2011/0307034 | A1 | 12/2011 | Hastrings et al. |
| 2012/0017804 | A1 | 1/2012 | Venema et al. |
| 2012/0083784 | A1* | 4/2012 | Davison ............ A61B 18/1445 606/41 |
| 2012/0089153 | A1* | 4/2012 | Christopherson .... A61B 5/4818 606/129 |
| 2012/0157804 | A1 | 6/2012 | Rogers et al. |
| 2012/0172924 | A1* | 7/2012 | Allen, IV ............... A61B 17/29 606/205 |
| 2012/0253370 | A1* | 10/2012 | Ross .............. A61B 17/320092 606/169 |
| 2012/0253372 | A1* | 10/2012 | Ross .............. A61B 17/320092 606/169 |
| 2012/0310237 | A1* | 12/2012 | Swanson ................ A61B 18/08 606/41 |
| 2012/0310241 | A1* | 12/2012 | Orszulak ................ A61B 18/12 606/41 |
| 2012/0330351 | A1* | 12/2012 | Friedman ......... A61B 17/12013 606/205 |
| 2013/0053831 | A1* | 2/2013 | Johnson ............. A61B 17/2909 606/1 |
| 2013/0053840 | A1* | 2/2013 | Krapohl ............. A61B 18/1445 606/33 |
| 2013/0121366 | A1* | 5/2013 | Misuchenko .. A61B 17/320092 73/649 |
| 2013/0226178 | A1* | 8/2013 | Brandt .................. A61B 18/12 606/49 |
| 2013/0267874 | A1* | 10/2013 | Marcotte .............. A61B 5/4893 606/41 |
| 2013/0267947 | A1* | 10/2013 | Orszulak ............ A61B 18/1233 606/41 |
| 2014/0275993 | A1 | 9/2014 | Ballakur |
| 2015/0066000 | A1* | 3/2015 | An ....................... A61B 5/1455 606/1 |
| 2015/0190194 | A1 | 7/2015 | Weber et al. |
| 2017/0188942 | A1 | 7/2017 | Ghaffari et al. |
| 2018/0078169 | A1 | 3/2018 | Feldman et al. |
| 2019/0069949 | A1 | 3/2019 | Vrba et al. |
| 2020/0337765 | A1 | 10/2020 | Smith |
| 2020/0375541 | A1 | 12/2020 | Shachar et al. |
| 2021/0307824 | A1 | 10/2021 | Asirvatham et al. |
| 2022/0047202 | A1 | 2/2022 | Shachar et al. |
| 2023/0057437 | A1 | 2/2023 | Sullivan et al. |

FOREIGN PATENT DOCUMENTS

| | | |
|---|---|---|
| AU | 2013230893 B2 | 12/2015 |
| AU | 2013305279 B2 | 7/2017 |
| AU | 2015358385 B2 | 9/2020 |
| CA | 2934245 A1 | 7/2015 |
| CA | 2969129 A1 | 6/2016 |
| CA | 2749024 C | 10/2016 |
| CN | 203138452 U | 8/2013 |
| CN | 102292395 B | 7/2014 |
| CN | 103284693 B | 12/2014 |
| CN | 103271766 B | 8/2015 |
| CN | 105828709 A | 8/2016 |
| CN | 106068105 A | 11/2016 |
| CN | 105120785 B | 11/2017 |
| CN | 107802341 B | 7/2020 |
| CN | 105658163 B | 8/2020 |
| CN | 111700677 A | 9/2020 |
| DK | 2389415 T3 | 11/2014 |
| EP | 1451595 B1 | 7/2009 |
| EP | 2347726 A2 | 7/2011 |
| EP | 2389415 B1 | 8/2014 |
| EP | 2435129 B1 | 7/2015 |
| EP | 13798005.8-1659 | 10/2015 |
| EP | 2513953 B1 | 10/2017 |
| EP | 3038555 B1 | 7/2018 |
| EP | 2986243 B1 | 6/2020 |
| EP | 3226795 B1 | 8/2020 |
| EP | 2887900 B1 | 12/2020 |
| EP | 2967713 B1 | 12/2020 |
| EP | 3799815 A1 | 4/2021 |
| EP | 3038556 B1 | 5/2021 |
| EP | 3884897 A1 | 9/2021 |
| EP | 4144294 A1 | 3/2023 |
| ES | 2329773 T3 | 12/2009 |
| ES | 2523498 T3 | 11/2014 |
| IN | 202048041803 | 9/2021 |
| JP | 2006509547 A | 3/2006 |
| JP | 5405706 B2 | 2/2014 |
| JP | 5681117 B2 | 3/2015 |
| JP | 5694947 B2 | 4/2015 |
| JP | 2016534842 A | 11/2016 |
| JP | 2017502752 A | 1/2017 |
| JP | 6109863 B2 | 4/2017 |
| JP | 2017148514 A | 8/2017 |
| JP | 6204616 B2 | 9/2017 |
| JP | 2017536187 A | 12/2017 |
| JP | 6574134 B2 | 9/2019 |
| KR | 101590005 B1 | 1/2016 |
| KR | 20160106582 A | 9/2016 |
| KR | 101743628 B1 | 6/2017 |
| NL | 2002442 C2 | 7/2010 |
| WO | 2001093759 A1 | 12/2001 |
| WO | 2003048789 A2 | 6/2003 |
| WO | 2004052182 A2 | 6/2004 |
| WO | 2006044868 A1 | 4/2006 |
| WO | 2007008057 A1 | 1/2007 |
| WO | 2010030373 A2 | 3/2010 |
| WO | 2010082993 A2 | 7/2010 |
| WO | 2010085140 A1 | 7/2010 |
| WO | 2010129661 A1 | 11/2010 |
| WO | 2011084450 A1 | 7/2011 |
| WO | 2011093991 A1 | 8/2011 |
| WO | 2012027320 A2 | 3/2012 |
| WO | 2013134479 A1 | 9/2013 |
| WO | PCT/US2013/042847 | 10/2013 |
| WO | 2014029355 A1 | 2/2014 |
| WO | 2014172398 A1 | 10/2014 |
| WO | 2015031643 A1 | 3/2015 |
| WO | 2015031648 A1 | 3/2015 |
| WO | 2015061457 A1 | 4/2015 |
| WO | 2015102951 A2 | 7/2015 |
| WO | 2015103541 A1 | 7/2015 |
| WO | 2016090175 A1 | 6/2016 |
| WO | 2020242753 A1 | 12/2020 |
| WO | 2023038682 A1 | 3/2023 |
| WO | 2023038748 A1 | 3/2023 |

* cited by examiner

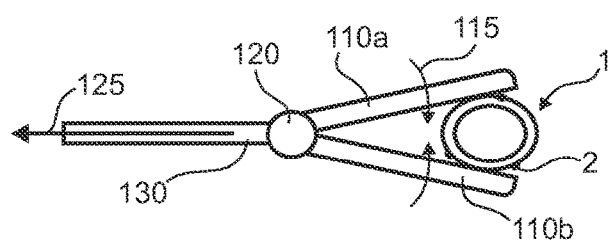
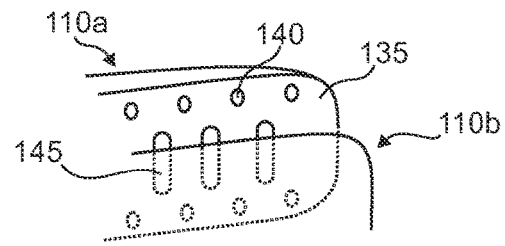
Fig 1a  Fig 1b
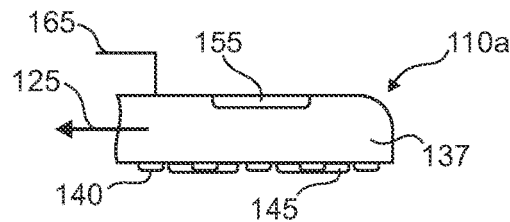
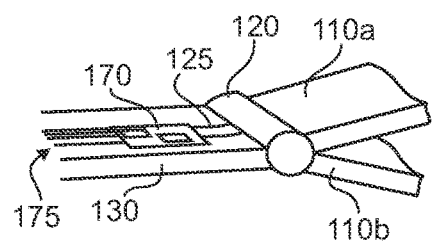
Fig 1c  Fig 1d
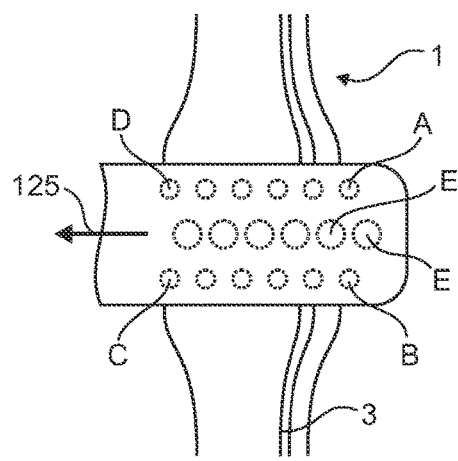
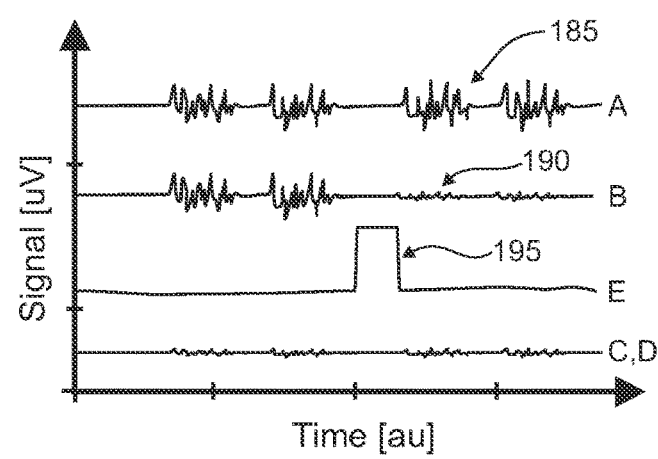
Fig 1e  Fig 1f

ENDOSCOPIC SYMPATHECTOMY SYSTEMS AND METHODS

CROSS-REFERENCE TO RELATED APPLICATION

The present application is a continuation of U.S. application Ser. No. 16/252,207 filed on Jan. 18, 2019, which is a continuation of U.S. application Ser. No. 15/920,775 filed on Mar. 14, 2018, which is a continuation of U.S. application Ser. No. 14/403,891 filed on Nov. 25, 2014, which is a national stage application of International Application No. PCT/US2013/042847 filed on May 28, 2013, which claims benefit of and priority to U.S. Provisional Application Ser. No. 61/652,426 filed on May 29, 2012, entitled "Endoscopic Sympathectomy Systems and Methods", by Landy Toth et al., the entire contents of which are incorporated by reference herein for all purposes.

BACKGROUND

Technical Field

The present disclosure relates to the field of minimally invasive sympathectomy. The disclosure relates to methods for locating, monitoring, and/or mapping nerve distributions before, during, and/or following a surgical process. The disclosure relates to systems and methods for monitoring the extent of a surgical process as it pertains to a surgical goal, such as denervation. The invention also relates to endoscopic systems specifically designed for use in nerve monitoring and ablation.

Background

Congestive heart failure, hypertension, diabetes, and chronic renal failure have many different initial causes; however, all may include some form of renal sympathetic nerve hyperactivity. Renal sympathetic nerves communicate signals with sympathetic centers located in the spinal cord and brain via afferent renal nerve activity, increasing systemic sympathetic tone; meanwhile, through efferent activity, renal nerves and arteries participate in sympathetic hyperactivity in response to signals from the brain, further increasing systemic sympathetic tone.

Sympathetic activation can initially be beneficial but eventually becomes maladaptive. In a state of sympathetic hyperactivity, a number of pathological events take place: abnormalities of hormonal secretion such as increased catecholamine, renine and angiotensin II levels, increased blood pressure due to peripheral vascular constriction and/or water and sodium retention, renal failure due to impaired glomerular filtration and nephron loss, cardiac dysfunction and heart failure due to left ventricular hypertrophy and myocyte loss, stroke, and even diabetes. Therefore, modulation (reduction/removal) of this increased sympathetic activity can slow or prevent the progression of these diseases.

Although ablation of such nerves can have positive effects on drug resistant hypertension and glucose metabolism abnormality, current methodologies for denervation (e.g. ablation) are conducted without adequate feedback (with respect to the site of a denervation event, the extent of denervation, the effect of denervation on local physiology, etc.).

SUMMARY

One objective of this disclosure is to provide a microsurgical tool for monitoring, evaluating, mapping, and/or modulating electrophysiological activity in the vicinity of an organ or a vessel within a body. Another objective is to provide a system and method for evaluating the sympathetic tone of a subject. Yet another objective is to provide a system for neuromodulating an anatomical site in the vicinity of an organ or vessel within a body. Another objective is to provide an implantable device for monitoring and/or performing a neuromodulation procedure.

The above objectives are wholly or partially met by devices, systems, and methods according to the appended claims in accordance with the present disclosure. Features and aspects are set forth in the appended claims, in the following description, and in the annexed drawings in accordance with the present disclosure.

According to a first aspect there is provided, a microsurgical tool for monitoring electrophysiological activity within the vicinity of an organ within a body, the microsurgical tool including an endoscopically deliverable elongate structure configured so as to extend from an entry site within the body to the vicinity of the organ; and a sensing tip electrically and mechanically coupled to the elongate structure, configured to interface with tissues in the vicinity of the organ, the sensing tip configured to convey one or more electrophysiological signals associated with the activity.

In aspects, the electrophysiological signals may be related to one or more of water concentration, tissue tone, evoked potential, remotely stimulated nervous activity, sympathetic nervous activity, an electromyographic signal [EMG], a mechanomyographic signal [MMG], a local field potential, an electroacoustic event, vasodilation, vessel wall stiffness, muscle sympathetic nerve activity [MSNA], central sympathetic drive, nerve traffic, combinations thereof, or the like.

In aspects, one or more sensing tips may include an electrode. In aspects, the electrode may include embossed, plated, and/or filament loaded structures thereupon.

In aspects, the microsurgical tool may include a microcircuit, electrically coupled with one or more of the sensing tips.

In aspects, the sensing tip is electrically coupled with a microcircuit, the microcircuit configured to condition the signal. In aspects, the microcircuit is embedded into the microsurgical tool and at least a portion of the electrical coupling is provided via the elongate structure. In aspects, the microcircuit is embedded into the sensing tip or the elongate structure.

In aspects, one or more of the sensing tips may include one or more needle electrodes and/or one or more whiskers each of which having a characteristic length and a tip, the needle electrode and/or whiskers arranged so as to extend from the sensing tip into the tissues adjacent thereto. In aspects, one or more of the needle electrodes and/or the whiskers may include electrical insulation along the length thereof and may include an electrically exposed tip. In aspects, one or more sensing tips may include a mechanomyographic (MMG) sensing element configured to generate a mechanomyographic signal (MMG) from the activity, a compliance sensor, configured to generate a tissue tone signal, or the like. In aspects, one or more sensing tips may include a microelectrode configured to interface with the adjacent tissues, the microelectrode having an area of less than 5000 µm$^2$, less than 1000 µm$^2$, less than 250 µm$^2$, less than 100 µm$^2$, or the like.

In aspects, the microsurgical tool may include one or more stimulating electrodes, each electrically and mechanically coupled to the elongate structure, the stimulating electrodes configured to provide a stimulating and/or ablating current to the adjacent tissues during use. In aspects, the microsurgical tool may be configured to coordinate stimulating and/or ablating currents between two or more of the stimulating electrodes via the adjacent tissues. One of more of the sensing tips may be configured so as to monitor the effect of the stimulating and/or ablating current(s) on the adjacent tissues and/or tissues related thereto. In aspects, the stimulating electrodes may have an area of greater than 0.1 mm$^2$, 0.5 mm$^2$, 1 mm$^2$, 2 mm$^2$, or 10 mm$^2$.

In aspects, a microsurgical tool in accordance with the present disclosure may include means for delivering a therapeutic substance to the adjacent tissues. In aspects, one or more sensing tips in accordance with the present disclosure may be configured to monitor the effect of the therapeutic substance on the adjacent tissues or tissues related thereto. In aspects, the therapeutic substance may include a chemical, a drug substance, a neuromodulating substance, a neuroblocking substance, an acid, a base, a denervating agent, or a combination thereof. In aspects, the therapeutic substance may include a neurotoxin, a botulinum toxin, a tetrodotoxin, a tetraethylammonium, a chlorotoxin, a curare, a conotoxin, a bungarotoxin, arsenic, ammonia, ethanol, hexane, nitric oxide, glutamate, resiniferatoxin, alchohol, phenol, capaicin, an anesthetic, lidocaine, tetanus toxin, quaternary ammonium salts, a pachycurare, a leptocurare, acetylcholine, aminosteroids, a combination thereof, or the like.

In aspects, the therapeutic substance may include a restraining matrix, which may or may not be at least partially biodegradable. In aspects, the restraining matrix may include a photopolymerizable polymer, and the microsurgical tool may include a light source, for performing in situ photopolymerization thereof.

In aspects, the microsurgical tool may include a clamp, one or more sensing tips and/or stimulating electrodes comprised within the clamp, arranged so as to bias towards the tissues when the clamp is closed thereupon. In aspects, the clamp is configured to controllably close down onto the tissues with a predetermined clamping force. In aspects, wherein the clamp is configured so as to produce a pressure of greater than 20 mmHg, 40 mmHg, 60 mmHg, 80 mmHg when closing down onto the tissues. In aspects, one or more sensing tips is configured to monitor the effect of the closing on the adjacent tissues.

In aspects, the microsurgical tool includes a self-wrapping tool comprising one or more sensing tips and/or stimulating electrodes, the sensing tips and/or stimulating electrodes arranged so as to bias towards the tissues when the self-wrapping tool is bent there around.

In aspects, the microsurgical tool may include a clamp, a self-wrapping tool, or the like each in accordance with the present disclosure. In aspects, the self-wrapping tool may include an electroactive material actuator electrically and mechanically coupled to the elongate structure, to provide movement thereof during use.

In aspects, the self-wrapping tool may include one or more microchannels, the microchannels configured to support a vacuum to provide movement thereof during use, and/or facilitate attachment to the tissues. In aspects, the self-wrapping tool may include one or more tendons, each tendon arranged so as to run along the length of the elongate structure, the tendons arranged so as to provide the movement when pulled during use.

In aspects, the microsurgical tool includes means to deliver a feature enhancing medium to the adjacent tissues. In aspects, the feature enhancing medium comprises a visual marking moiety to assist with visualization of a one or more tissue types in the adjacent tissue.

According to another aspect there is provided, use of a microsurgical tool in accordance with the present disclosure to monitor electrophysiological activity in the vicinity of a vessel, an artery, a vein, a tubule, a renal artery, an organ, a kidney, a spleen, a pancreas, a prostate, a combination thereof, or the like.

According to yet another aspect there is provided, use of a microsurgical tool in accordance with the present disclosure to perform a surgical procedure.

According to another aspect there is provided, use of a microsurgical tool in accordance with the present disclosure to perform a renal neuromodulation procedure.

According to yet another aspect there is provided, a system for neuromodulating an anatomical site in the vicinity of an organ or vessel, including a subsystem configured to perform a surgical procedure on the anatomical site; a microsurgical tool in accordance with the present disclosure configured to monitor electrophysiological activity in the vicinity of the site; and a control unit configured to accept signals from the microsurgical tool, and to adjust the surgical procedure dependent upon the signals, to display the signals, to evaluate the surgical procedure dependent upon the signals, to plan a surgical path dependent upon the signals, and/or to determine the extent of the procedure dependent upon the signals.

In aspects, the surgical procedure may be selected from an ablation, an excision, a cut, a burn, a radio frequency ablation, a cryoablation, a radiosurgical procedure, delivery of energy, an ultrasonic ablation, an abrasion, a biopsy, delivery of a substance, a combination thereof, or the like.

In aspects, the system may include a stimulation and/or ablation electrode configured so as to convey a pulsatile and/or radio frequency signal to the anatomical site from the control unit, the microsurgical tool configured to convey one or more feedback signals related to the pulsatile and/or radio frequency signals back to the control unit. In aspects, the feedback signals are related to an electrode impedance, a bioimpedance, a local electrical field, and/or an electrophysiological response to the pulsatile and/or radio frequency signal. In aspects, the stimulation and/or ablation electrode may be included within the microsurgical tool. In aspects, the stimulation and/or ablation electrode is comprised within the sensing tip. In aspects, the control unit is configured to sweep one or more of the sensing tips along the organ or vessel.

In aspects, the system may be configured to use one or more of the electrophysiological signals to locate the anatomical site.

In aspects, the control unit may be configured to use one or more of the electrophysiological signals to exclude the anatomical site from a surgical procedure.

According to yet another aspect there is provided a method for determining an afferent electrophysiological activity and an efferent physiological activity in the vicinity of an organ, including monitoring electrophysiological activity at a plurality of sites within the vicinity of the organ in regions proximal and distal to a target region as measured along a length of the organ or the location of the organ in relation to a connected neurological structure; applying energy to a site within the target region to form a neurological block thereby; and extracting an afferent signal from activity in the distal region and an efferent signal from activity in the proximal region.

In aspects, the method may include comparing activity measured in the proximal region and the distal region to determine if the energy application affected the electrophysiological activity in the vicinity of the target region, evaluating the coherence between activities measured in the proximal region and the distal region, and using the coherence to evaluate the extent of the neural block.

In aspects, the application of energy may be sufficient to form a temporary neural block. The method may include comparing activities from the proximal region and the distal region during the temporary neural block and diagnosing a neurological condition, evaluating a neurological state, or determining if a permanent surgical procedure is required.

According to another aspect there is provided, a method for evaluating sympathetic tone of a subject, including inserting a microsurgical tool in accordance with the present disclosure into the subject within the vicinity of a target organ or vessel; recording the electrophysiological signals conveyed by the microsurgical tool; removing the microsurgical tool from the subject; and generating a metric relating to sympathetic tone from the recorded signals.

In aspects, the method may include monitoring another physiological parameter remotely from the target organ or vessel to generate a corrective signal and using the corrective signal to remove movement artifacts from the electrophysiological signals. In aspects, the method may include stimulating one or more anatomical sites in the subject during the recording, and/or diagnosing a medical condition based at least in part upon the metric.

According to yet another aspect there is provided, a method for monitoring and/or evaluating electrophysiological activity in the vicinity of a vessel, including biasing an electrode against a wall of the vessel from the outside of the vessel; and recording one or more electrophysiological signals from the activity in the vicinity of the electrode.

In aspects, the method may include recording one or more of an evoked potential, remote stimulation of nervous activity, an electromyographic signal [EMG], a mechanomyographic signal [MMG], a local field potential, an electroacoustic event, vasodilation, vessel wall stiffness, muscle sympathetic nerve activity [MSNA], central sympathetic drive, tissue tone, nerve traffic, combinations thereof, or the like in the vicinity of the electrode.

In aspects, the method may include electrically isolating the electrode from a cavity of the vessel, embedding the electrode into the wall of the vessel, sweeping the electrode along the wall of the vessel, generating a map of electrophysiological activity from the recordings obtained during the sweep, recording electrophysiological activity from a plurality of electrodes, cancelling one or more movement artifacts from the recordings, and/or biasing a mechanomyographic (MMG) sensing element against the wall of the vessel and recording a mechanomyographic signal (MMG) from the activity.

In aspects, one or more of the steps may be performed with a microsurgical tool in accordance with the present disclosure.

According to yet another aspect there is provided, a method for performing controlled neuromodulation in the vicinity of an organ or vessel, including: monitoring electrophysiological activity at one or more sites within the vicinity of the organ or vessel to obtain a first activity level; applying energy to a treatment site within the vicinity of the organ or vessel; monitoring electrophysiological activity at one or more sites within the vicinity of the organ or vessel to obtain a second activity level; and comparing the first activity level and the second activity level to determine if the energy application affected the electrophysiological activity, if sufficient energy was applied, or if further energy should be applied.

In aspects, the monitored electrophysiological activity comprises one or more of an evoked potential, remote stimulation of nervous activity, an electromyographic signal [EMG], a mechanomyographic signal [MMG], a local field potential, an electroacoustic event, vasodilation, vessel wall stiffness, muscle sympathetic nerve activity [MSNA], central sympathetic drive, tissue tone, nerve traffic as measured in the vicinity of the organ or vessel.

In aspects, the method may include determining if sufficient energy has been applied to the treatment site based on the comparison, evaluating the first activity level to determine a suitable treatment site in the vicinity of the organ or vessel, mapping electrophysiological activity in the vicinity of the organ or vessel using the first activity level, applying a stimulus in the vicinity of the organ or vessel, recording electrophysiological activity before, during, and/or after the stimulus, recording electrophysiological activity in a proximal region and a distal region measured along the length of the organ or vessel as spaced with respect to the treatment site, to determine if the energy application affected the electrophysiological activity in the vicinity of the treatment site, and/or determining if the energy application was sufficient to form a neural block using the comparison.

In aspects, the method may include applying sufficient energy (i.e. RF energy, ultrasound energy, thermal energy, microwave energy, radiation, etc.) to the treatment site to form a temporary block and assessing if the change in electrophysiological activity is desirable, if so, applying sufficient energy to the treatment site so as to form a substantially irreversible block. In aspects, wherein the energy is in the form of a radio frequency current, an ultrasonic wave, or thermal energy.

In aspects, one or more of the steps may be performed using a microsurgical tool in accordance with the present disclosure.

According to another aspect there is provided, a method for determining a state of a neurological connection along a neurological pathway between one or more regions in a body, including: applying a pacing signal to the wall of a vessel from the outside of the vessel in the vicinity of the neurological pathway; monitoring one or more of water concentration, tone, blood oxygen saturation of local tissues, evoked potential, stimulation/sensing of nervous activity, electromyography, temperature, blood pressure, vasodilation, vessel wall stiffness, muscle sympathetic nerve activity [MSNA], central sympathetic, tissue tone, blood flow, a blood flow differential signal, blood perfusion, a blood analyte level, nerve traffic, or combinations thereof, at one or more sites within the body to generate one or more physiological signals; and evaluating the influence of the pacing signal on the physiological signals and determining the state of neurological connection therefrom.

In aspects, the method may include applying energy in the vicinity of the vessel so as to induce a neurological block along the neurological pathway, pacing and monitoring before and after induction of the neurological block, comparing the physiological signals obtained before the neurological block to those obtained during the neurological block to determine the influence of the neurological block thereupon, determining if the neurological block is favorable in terms of treating an underlying disease state in the body, applying energy in the vicinity of the vessel so as to induce a substantially permanent neurological block along the neurological pathway, and/or monitoring electrophysiological activity at a plurality of sites in the vicinity of the vessel in regions proximal and distal to the pacing site and/or to the site of a suspected or known neurological block.

In aspects, the method may include extracting an afferent signal from activity in the distal region and an efferent signal from activity in the proximal region, and/or comparing activity measured in the proximal region and the distal region to determine if the energy application affected the electrophysiological activity in the vicinity of the target region.

In aspects, one or more of the steps may be performed using a microsurgical tool in accordance with the present disclosure.

According to yet another aspect there is provided, use of a method in accordance with the present disclosure for evaluation of the effectiveness of a neuromodulation procedure within a body.

According to another aspect there is provided, an implantable device for monitoring electrophysiological activity within the vicinity of an organ within a body, the implantable device including: a housing including a microcircuit configured acquire and communicate signals, and a power supply or energy harvesting element; one or more microfingers attached to the housing, configured so as to extend from housing to the vicinity of the organ; and one or more sensing tips electrically and mechanically coupled to one or more of the microfingers, configured to interface with tissues in the vicinity of the organ, the sensing tips configured to convey one or more electrophysiological signals associated with the activity to the microcircuit.

In aspects, the electrophysiological signals may be related to one or more of water concentration, tissue tone, evoked potential, remotely stimulated nervous activity, sympathetic nervous activity, an electromyographic signal [EMG], a mechanomyographic signal [MMG], a local field potential, an electroacoustic event, vasodilation, vessel wall stiffness, muscle sympathetic nerve activity [MSNA], central sympathetic drive, nerve traffic, or combinations thereof.

In aspects, one or more of the sensing tips may include one or more needle electrodes and/or one or more whiskers each of which having a characteristic length and a tip, the needle electrode and/or whiskers arranged so as to extend from the sensing tip into the tissues adjacent thereto. In aspects, one or more of the needle electrodes and/or the whiskers may include electrical insulation along the length thereof and/or electrically exposed tips. In aspects, one or more sensing tips may include a microelectrode configured to interface with the adjacent tissues, the microelectrode having an area of less than 5000 $\mu m^2$, less than 1000 $\mu m^2$, less than 250 $\mu m^2$, or less than 100 $\mu m^2$.

In aspects, the implantable device may include one or more stimulating electrodes electrically and mechanically coupled to one or more of the microfingers, the stimulating electrodes configured to provide a stimulating and/or ablating current to the adjacent tissues. Optionally, the microcircuit may be configured to coordinate stimulating and/or ablating currents between two or more of the stimulating electrodes via the adjacent tissues, and/or one or more of the sensing tips may be configured so as to monitor the effect of the stimulating and/or ablating current(s) on the adjacent tissues and/or tissues related thereto.

In aspects, an implantable device in accordance with the present disclosure may include means for delivering a therapeutic substance in accordance with the present disclosure to the adjacent tissues. In aspects, one or more of the sensing tips may be configured to monitor the effect of the therapeutic substance on the adjacent tissues or tissues related thereto. In aspects, the therapeutic substance is selected from a chemical, a drug substance, a neuromodulating substance, a neuroblocking substance, an acid, a base, a denervating agent, or a combination thereof. In other aspects, the therapeutic substance is a selected from a neurotoxin, a botulinum toxin, a tetrodotoxin, a tetraethylammonium, a chlorotoxin, a curare, a conotoxin, a bungarotoxin, arsenic, ammonia, ethanol, hexane, nitric oxide, glutamate, resiniferatoxin, alchohol, phenol, capaicin, an anesthetic, lidocaine, tetanus toxin, quaternary ammonium salts, a pachycurare, a leptocurare, acetylcholine, aminosteroids, or a combination thereof. In aspects, the therapeutic substance is comprised within a restraining matrix. In aspects, the restraining matrix is at least partially biodegradable.

BRIEF DESCRIPTION OF THE DRAWINGS

Several aspects of the disclosure can be better understood with reference to the following drawings. In the drawings, like reference numerals designate corresponding parts throughout the several views.

FIGS. 1a-f show aspects of a surgical tool in accordance with the present disclosure.

DETAILED DESCRIPTION

Figure 2A:
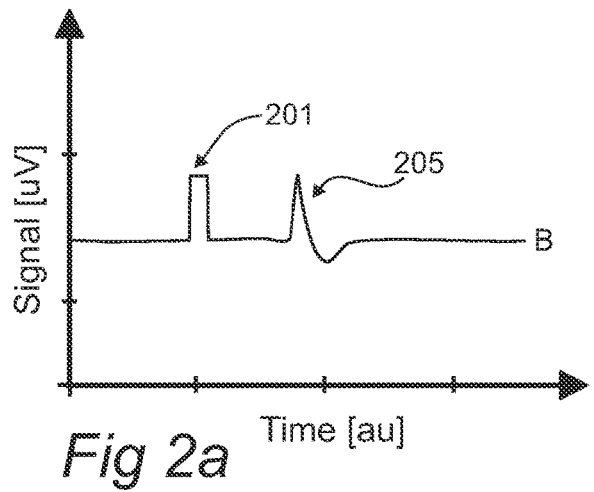
FIGS. 2a-b show stimulation and monitored signals in accordance with the present disclosure.

Particular embodiments of the present disclosure are described hereinbelow with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

A controlled nerve ablation system and/or neuromodulation system in accordance with the present disclosure may include the capability to sense one or more physiological parameters at one or more points in the vicinity of a surgical site, and/or include the capability to stimulate, deliver a neuromodulating substance, and/or ablate tissues at one or more of the same points and/or an alternative point around a surgical site. The nerve ablation and/or neuromodulation system may be configured so as to access vessels and/or surgical sites in the body. In aspects, one or more examples disclosed herein may be directed towards such system configurations (e.g. so as to controllably ablate renal nerves along a renal artery via an endoscopic procedure, to controllably modulate the function of an organ, to controllably modulate neural activity in the vicinity of a surgical site, etc.).

A controlled nerve ablation system and/or neuromodulation system in accordance with the present disclosure may include one or more sensing tips (e.g. as located on a micro-tip, a wire, an electrode in a matrix, on a flexible balloon, a clamp, a hook-like structure, a net-like structure, etc.). One or more sensing tips may include a pressure sensor, a tonal sensor, a temperature sensor, an electrode (e.g. to interact with a local tissue site, provide a stimulus thereto, measure a potential therefrom, monitor current to/from the tissues, to measure a bioimpedance, measure an evoked potential, neural activity, an electromyographic signal [EMG], an electrocardiographic signal [ECG], a mechanomyographic signal [MMG], a local field potential, etc.), an acoustic sensor, an oxygen saturation sensor, or the like.

The sensing tips may be configured to elucidate a range of key physiological aspects before, during, and/or after a procedure. The following description outlines some non-limiting approaches in this respect. Such sensing tips may be integrated into one or more microfingers, micro-tips, clamp faces, tool surfaces, flexible circuits, stretchable substrates, etc.

In aspects, one or more sensing tips in accordance with the present disclosure may be configured to monitor bioimpedance between one or more sensing tips to determine the degree of contact between the finger tips and the anatomical site, and/or potentially the bias force between the finger tips and the anatomical site. Additionally, alternatively, or in combination, bioimpedance measurements between one or more sensing tips may be useful in determining when adequate contact has been made as well as how much current should be applied to an anatomical site during an ablation procedure. Furthermore, additionally, alternatively, or in combination bioimpedance between one or more sensing tips may be used to determine the status of tissue positioned there between. In one non-limiting example, the bioimpedance spectrum between two or more sensing tips may be used to map the local tissue impedance. Such information may be useful to elucidate where such tissue has been completely ablated, where tissue has yet to be ablated, etc.

In aspects, bioimpedance measurement between on or more sensing tips, a sensing tip and a separate electrode, etc. may be used to determine a state of isolation between one or more of the sensing tips and a local fluid (i.e. to determine a state of isolation between a sensing tip and fluid within a lumen, between a sensing tip and blood, etc.).

In aspects, one or more sensing tips in accordance with the present disclosure may be configured to obtain mechanomyographic information during a procedure as determined by slight changes in an associated strain measurement, tip vibration, and/or contact force measurement (e.g. via direct force measurement between the tip and the local anatomy, and/or via changes in the deformation of the microfinger as measured by an associated micro strain gage attached thereupon). Mechanomyographic information may be related to local nervous activity either naturally occurring or in response to a stimulus (e.g. optionally applied by one or more sensory tips, locally, remotely, during and/or via a local RF pulse, etc.). In aspects, a sensing tip may include a piezoresistive strain gauge, a piezoelectric microtransducer, an interfacial pressure sensing membrane, or the like to detect mechanomyographic signals. In one non-limiting example, the sensing tip may be coated with a micro or nano coating of a piezoresistive and or piezoelectric material (e.g. a piezoelectric polymer, an electret, a nano-particulate filled elastomer, a conjugated polymer, etc.). In aspects, the mechanomyographic tip may be configured so as to measure one or more aspect of the tissue compliance of the local tissues (e.g. so as to identify calcified material, cancerous tissues, etc.).

In aspects, one or more sensing tips in accordance with the present disclosure may be configured to monitor an electrophysiological signal. Such electrophysiological monitoring at and/or between one or more sensing tips, may be used to map nervous response, electromyographic response (EMG), evoked potential, local field potential, extracellular field potentials, etc. along and/or within the wall of the local anatomical site (e.g. the wall of a lumen, a vessel wall, an artery wall, a venous wall, an organ wall, within a body of tissue, near an organ, near a ganglion, in the vicinity of a nerve plexus, etc.). Such information may be advantageous for selecting tissues on which to perform a surgical procedure (e.g. an ablation procedure, a neuromodulation procedure, signal interruption, chemical delivery, a biopsy, etc.), to follow and/or map a nerve along the length of the surgical site (e.g. along the wall of an artery, a vein, a tubule, in the vicinity of a body of tissue, a ganglion, etc.), to determine the state of a surgical procedure, etc. In aspects, one or more sensing tips may be configured to monitor a local electromyographic (EMG) signal before, during and/or after a surgical procedure as a means for monitoring local nervous activity (i.e. muscular activity associated with nerve traffic, etc.). In such aspects, the EMG signals may be used as feedback for monitoring the extent of a denervation or neuromodulation procedure.

In aspects, one or more sensing tips in accordance with the present disclosure may be configured to monitor the tone of a tissue within a body. Monitoring the tone (e.g. mechanical properties, wall stiffness, elastic spectral response, mechanical impedance, physiological properties, etc.) of the adjacent tissues may be determined by combining strain and/or force measurement of the sensing tips while applying movement (optionally cyclical or oscillatory movement) to one or more sensor tips. Such sensing tips may be excited locally (e.g. such as by a local piezoelectric transducer, a capacitive transducer, an electrochemical transducer, a smart material, etc.) or globally (e.g. such as by oscillatory torsional oscillations, axial oscillations, linear oscillations of the surgical tool tip, the associated guide wire, catheter, etc.).

In aspects, one or more of the sensing tips may be interfaced asymmetrically with the associated tissues (i.e. with a bent tip, a micro finger, a wire-like finger configured substantially parallel to the tissue surface, oriented at an acute angle thereto, etc.). By asymmetrically is meant such that the sensing tip approaches the associated tissue surface at an angle other than perpendicular thereto. To describe the use of such a tip to monitor local tissue tone and/or for providing a controlled interfacial force before, during and/or after a procedure, for purposes of discussion, a clockwise torsion may be used to advance the sensing tip along the surface of the local tissues and a relatively small counterclockwise torsion may be used to measure the tone of adjacent tissues. By relatively small is meant an excitation that is sufficiently small in amplitude such that the sensing tip may not appreciably slide along the tissue surface. In aspects, one or more sensory tips, in a structure attached thereto, and/or a system in accordance with the present disclosure may include a vibratory exciter, which may be configured to generate the excitation.

In aspects, such a tone monitor may be combined with interfacial contact sensing, electrophysiological measurement, and/or sensor tip strain measurement in order to generate a wealth of local tissue related physiological information before, during, and/or after a surgical procedure. In one non-limiting example, the local tissues may stiffen during an ablation procedure. By monitoring local tissue tone, a stiffness level may be used to characterize when a suitable degree of ablation has been applied so as to irreversibly damage the tissues. Monitoring of a local tissue tone, perhaps at a monitoring site significantly removed from the surgical site such that the surgical procedure does not directly affect tissues in the vicinity of the monitoring site (i.e. does not directly cut, heat, ablate, abrade, the tissues, etc.) may also be advantageous for determining an effect of the surgical procedure on one or more physiological parameters of a tissue (e.g. a vessel wall stiffness, change in nerve activity, change in blood perfusion, etc.) adjacent to the monitoring site.

In aspects, such tone measurement may be useful in determining the local stiffness of tissues (and/or overall wall stiffness of an adjacent vessel, organ, etc.) in contact with a sensing tip array (e.g. so as to determine the type of tissue adjacent to one or more sensing tips, locate plaque, locate a cancerous tumor, etc.). Tone measurement may further be used to characterize the type of tissue with which the tip is interfacing (e.g. muscle, nervous tissue, fat, plaque, cancerous tissue, etc.). In aspects, such information, possibly in combination with bioimpedance data, electrophysiological monitoring, or the like, may be used to determine how much RF energy to apply locally during an RF ablation procedure.

In aspects of a method for RF ablating tissue in accordance with the present disclosure, the local tissue tone may be measured before, during, between individual RF pulses, and/or after a train of RF pulses. As the local tissue tone changes during application of the RF pulses, the tonal changes may be used to determine the extent of the therapy. As the RF ablation process is applied to the adjacent tissues (perhaps via one or more sensing tips), the tonal measurements (as determined by one or more sensing tips, perhaps the same tip through which the RF signal may be applied) may be monitored as the tonal measurements may not be significantly affected by the local RF currents.

In aspects, electrophysiological stimulation and/or sensing from one or more sensing tips in a sensing tip array, or a system in accordance with the present disclosure may be used to interface with, monitor and/or stimulate nervous function within a local anatomical structure (e.g. a lumen wall, a vessel wall, along a nerve, an organ wall, a duct, etc.). Such information may be used to hunt for target tissues (e.g. nerves), select tissues for a surgical procedure, to determine the degree of progression of a surgical procedure (e.g. a degree of ablation during RF surgery, etc.), determine interconnection of a neural target with an adjacent organ and/or physiological function thereof, or the like.

In aspects, an array of sensing tips may be configured to apply a directional stimulation and/or multi-site sensing so as to selectively treat/monitor only nerves that are configured to send signals in the preferred direction (e.g. to selectively target primarily efferent nerve bundles, afferent nerve bundles, etc.). Such a configuration may be advantageous for treating a neurological disorder with minimal impact to the surrounding anatomy and physiological function of the associated organs.

In aspects, one or more sensing tips in accordance with the present disclosure may include the capability to apply/receive an RF current to/from the surrounding tissue. The RF current may be provided locally between two of more sensing tips, or alternatively between one or more sensing tips and a macroelectrode placed elsewhere on the body (e.g. on a large skin patch over the surgical site, as selected from multiple patches placed over the body, etc.). In a non-limiting example where current is restricted to being applied between sensing tips, the path for current flow may be well controlled, yet may be highly localized. Alternatively, in an example where RF current is passed between one or more sensing tips and one or more macroelectrodes, the direction of current flow may be more challenging to control, but may be used to access tissues more remote from the sensing tips (i.e. farther into the adjacent tissues, deeper into an organ, farther from a lumen wall, etc.).

In aspects, network impedance measurements between one or more sensing tips and one or more macroelectrodes (e.g. as attached to the body of the patient), may be monitored prior to and/or during application of an RF ablation current. Each sensing tip and/or macroelectrode may include an impedance control circuit that may be adjustable such that the overall current flow through the network formed from all the elements is controlled therethrough. Such a configuration may be advantageous to more precisely control the local ablation process, thus targeting the local tissues with more accuracy, precision, spatial discrimination, and confidence than less controlled approaches.

In aspects, a plurality of sensing tips may be engaged with the flow of RF current during an ablation process. In aspects, the local impedance of each microfinger and/or sensing tip may be monitored and/or controlled so as to better optimize the current delivered thereto. Additionally, alternatively, or in combination, the local current flow through each sensing tip may be monitored so as to determine the path of the RF current flow, to ensure no leakage currents are detected, etc. Such information may be used to more precisely control the delivery of RF currents to the local anatomy during an ablation procedure.

Additionally, alternatively, or in combination, before, during and/or after the RF current is applied to the surrounding tissues, one or more sensing tips may monitor a physiological parameter (e.g. water concentration, tone, blood oxygen saturation of local tissues, evoked potential, stimulation/sensing of nervous activity, local field potential, extracellular activity, EMG, temperature, etc.) to determine the extent of completion of the intended surgical procedure.

In aspects, one or more sensing tips may include an optical microsensor (e.g. a micropackage including a light source and/or a CMOS photosensor) and/or a fiber optic element. During a surgical procedure, the optical microsensor may be positioned against or near to the local tissues for analysis before, during and/or after an ablation procedure.

In aspects, an optically configured sensing tip (or group of tips) may be configured to locally assess blood perfusion and/or blood oxygenation in the tissues adjacent thereto. The system may be configured to automatically adjust and/or halt the surgical procedure based upon changes in this signal. Alternatively, additionally, or in combination, the system may alert a user (e.g. a surgeon, an attendant, etc.) to a change in this signal before, during, and/or after a surgical procedure. Such a configuration may be useful for assessing local tissue health before, during, and/or after a surgical procedure, the extent of a surgical procedure, etc.

In aspects, one or more optically configured sensing tips may be configured so as to be biased towards the tissues of a lumen, a vessel, or the like in the vicinity of the surgical site. The optical sensing tips may include one or more light sources (e.g. light emitting diodes, fiber optic tips, etc.) configured to deliver narrow, multiband, and/or wideband light to the adjacent tissues. In aspects, one or more of the optical sensing tips may include one or more photodetectors (e.g. a photodetector, a phototransistor, a fiber optic tip, etc.) to receive and/or analyze the light reflected from the adjacent tissues. The received light may be related to that emitted by one or more of the light sources, or may be received from an ambient light source, perhaps located to the exterior of the vessel, or the exterior of the subject's body.

The sources may be configured to emit light at predetermined wavelengths such that different absorption characteristics of the adjacent tissues, perhaps dependent on the wavelengths, may be observed during the surgical procedure. The photodetectors may be configured to receive at least a portion of this light, so as to assess the absorption characteristics with the system (perhaps via a pre-amplification system in accordance with the present disclosure, in an attached electronics unit, etc.). The photodetected signals may be used to determine an oximetry value or a signal related thereto.

In aspects, the optically configured sensing tips may be biased towards a site on the exterior of an adjacent vessel wall before, during, and/or after the surgical procedure. Alternatively or in combination, the optically configured sensing tips may be substantially stationary with respect to the vessel wall (such as via being attached to a collar of known size, attached to a structure of known width, as part of a structure that is expanded to a known radius, etc.). In aspects, the magnitude of the bias may be controlled by sensors and actuators both in accordance with the present disclosure. Changes in the optical signals detected by the photodetectors (perhaps due to changing bias force) before, during and/or after a surgical procedure may be related to changes in the bias force with which they are held against the vessel wall. Such a configuration may be advantageous for determining a change in sympathetic tone and/or vasodilation before, during and/or after a surgical procedure.

In aspects, the optically configured sensing tips may be coupled with one or more strain and/or interfacial force measurement methods, perhaps to give a more precise reading of the bias force between the sensing tip(s) and the adjacent tissues, to compensate for movement related artifacts, or the like.

In aspects, one or more of the optical sources may be selected such that the penetration of the light into the adjacent tissues may be controlled. In one non-limiting example, a substantially blue wavelength and a substantially red wavelength may be emitted into the tissues. The blue wavelength may provide information relating to the deformation and absorption near to the surface of the tissues, while the red wavelength may penetrate more deeply into the adjacent tissues, providing a signal that changes in response to deformation of tissues farther from the contact site(s) between the tip(s) and the tissue. The photodetectors or equivalent optical detection pathway may include filters, polarized windows, or the like to separately assess the different spectra during an analysis. Comparison between photodetected signals in the blue spectrum with those obtained from the red spectrum may be used to determine tone and/or elastic modulus of the tissues of the vessel in the vicinity of the sensing tip(s). Such a configuration may be advantageous for assessing sympathetic tone (i.e. via muscular tension measurement), and/or vasodilation, vessel wall stiffness, and/or local tissue stiffness before, during and/or after a surgical procedure. Changes in such properties may be indicative of the degree of completion of the surgical procedure.

In aspects, an externally placed (e.g. onto the body of the subject) light source (e.g. infrared, near infrared, visible, etc.) may be directed into the body towards the surgical site. The light source may optionally be modulated to provide a more easily detected signal within the subject. One or more sensing tips equipped with optical microsensors may sense light emitted from the light source. The mapping of received light may be used to locate and/or localize one or more anatomical features such as nerves near to one or more of the optical microsensor equipped sensing tips.

In aspects, one or more externally placed light sources and/or radiation based imaging source may be used to help locate the anatomical sites of interest during the procedure. An external energy source may include a narrow band light source, a broad band light source, radiological source, ultrasonic source, light sources spaced apart from each other, and/or combinations thereof, or the like. The energy sources may be modulated so as to be more easily detectable by sensors located on, in, or near to the anatomy of interest. In one non-limiting example, a plurality of light sources may be aimed at the surgical site from distinct vantage points within the body (i.e. as accessed via an endoscopic procedure, etc.) or externally to the body (i.e. as positioned at locations on the body).

In aspects, an endoscopic camera may be placed near to the anatomy, lumen wall, and/or surgical site of interest during a procedure to observe both the anatomy, as well as placement of the surgical tools in the vicinity of the anatomy.

In one non-limiting example, the endoscopic camera and/or light source may provide a suitable macroelectrode for RF ablation processes performed during the surgical procedure.

In aspects, one or more sensing tips may be equipped with a corresponding micro-light source (e.g. an oLED, an LED, etc.). The micro-light source may be used to direct light into the adjacent tissues. One or more sensing tips equipped with optical microsensors may be configured to detect light emitted from the micro-light source as back scattered by and/or transmitted through the adjacent tissues. Such information may be used to detect anatomical features (e.g. nerves, tumors, etc.) in the adjacent tissues.

Such optical configurations may be advantageous for mapping the local tissues before, during and/or after a surgical procedure. They may also be advantageous for implementation into a nerve detection system (e.g. perhaps as input to a nerve hunting algorithm, etc.). In aspects, such a system may be embodied by an optical coherence tomographic (OCT) configuration.

In aspects, the system may include a micro balloon catheter for placement into a vessel (e.g. a renal artery, etc.) or within tissues adjacent thereto, etc. The micro balloon catheter may be coated with a thin layer of an indicator molecule. The indicator molecule may be tagged to attach to the target tissue of interest and/or tagged so as to change chromatic properties when bound to the target tissue (e.g. nervous tissue, etc.). The molecules may be delivered to the desired tissues during a balloon catheterization procedure. During such a procedure, the micro balloon catheter may be placed into the vessel of interest and inflated so as to kiss the walls of the vessel. While in contact with the vessel walls, the indicator molecules may attach and migrate/diffuse into the local tissues. Such a procedure may be performed as a first surgical step or as combined with other aspects in accordance with the present disclosure. In aspects, the balloon may also be configured to deliver a therapeutic agent (i.e. a neuroblocking agent, ethyl alcohol, botox, etc.) to the anatomy of interest.

In a method in accordance with the present disclosure, one or more sensing tips may be inserted into a tissue adjacent to a target organ (i.e. a kidney, a ganglion, etc.), and/or a lumen with a wall within a body and biased towards the wall of the lumen or the target organ, and one or more electrophysiological signals obtained therefrom. The electrophysiological signals may be analyzed to locate one or more target tissues for a surgical procedure (i.e. one or more sympathetic nerves, parasympathetic nerves, etc.). A bolus of therapeutic agent (e.g. a neural ablative chemical, a neuroblocking substance, a neuromodulating substance, etc.), an RF current, a thermal energy source, and/or the like may be delivered to the identified tissues so as to perform the surgical procedure thereupon. In aspects, one or more post-procedural electrophysiological signals may be analyzed to determine the extent of the surgical procedure.

In aspects, the therapeutic agent may be provided via a micro balloon catheter in accordance with the present disclosure. In aspects, the therapeutic agent may be delivered via one or more microfingers in accordance with the present disclosure (i.e. via a fluid communicating lumen located there within).

In aspects, the micro balloon catheter may include one or more sensory tips (e.g. in the form of functional elements attached to the balloon, attached to a superstructure surrounding the balloon, etc.) in accordance with the present disclosure.

In aspects, the bioimpedance and/or electrophysiological signals between one or more sensing tips in the array and one or more sensing tips in the array, an external electrode, a reference electrode, or the like may be used to determine changes in the structure of the adjacent tissues during an ablation procedure. Such information may be useful in determining the extent of the ablation procedure, char accumulation, etc.

In aspects, bioimpedance measurements may be correlated with nerve damage data, perhaps obtained during prior surgeries, development of the procedure, and/or obtained during specific testing procedures, such that changes in local bioimpedance data may be used during a surgical procedure to determine the extent of the ablation procedure. Such a configuration may be advantageous in the case that the surgical procedure itself overwhelms the local electrophysiological activity to the extent that neurological monitoring may be hindered for a prolonged period of time after the procedure has been completed.

In aspects, one or more sensing tips may be configured to monitor local electrical fields during an ablation procedure in accordance with the present disclosure in order to better determine the current flow path through the adjacent anatomy, perhaps connected to a warning system to indicate to an operator when the ablation field is insufficient for achieving the intended goal. Such a configuration may be advantageous for avoiding unnecessary damage to the tissues during a misfired or misdirected ablation session.

In aspects, a system in accordance with the present disclosure may include a micro balloon catheter including one or more sensory tips (e.g. in the form of functional elements attached to the balloon, attached to a superstructure surrounding the balloon, etc.). The micro balloon catheter may be configured so as to bias the sensory tips against the adjacent vessel walls, thus providing a reliable interface from which selective ablation and detection processes may be performed. Such a micro balloon catheter may be advantageous for single placement type surgical procedures in accordance with the present disclosure.

In aspects including a plurality of sensing tips (e.g. as placed onto a micro balloon catheter, a microfinger array, a microtool set, a flexible cage assembly, a tree-like array of branching microfingers placed into tissues around a vessel, etc.), the sensing tips may be interconnected with each other, with signal processing circuitry, a local control circuit, and the like and/or combinations thereof. In order to substantially reduce the number of signal wires that must be sent to the surgical site during the procedure, the networked array of sensing tips may be multiplexed together with a locally placed control circuit (e.g. an application specific integrated circuit, distributed/interconnected circuit elements, a collection of flexible semiconducting circuit elements, etc.). The control circuit may be configured to communicate such signals with an extracorporeal system (e.g. a computer, a control system, an RF ablation controller, a data acquisition system, etc.). The control circuit may be configured to communicate with the extracorporeal system via analog and/or digital means and/or methods. In one non-limiting example, the communication may be of primarily digital means such that the control circuit may exchange data pertaining to any sensing tip in the array, as well as switch data, control data, RF pulse routing, etc.

In aspects, the networked array of sensing tips may be interconnected with distributed electronic elements and flexible electrical interconnects (e.g. as applied to a balloon wall, as provided by structural wires, microfingers, wire mesh elements, etc.). In aspects, one or more of the sensing tips, microfingers, or the like may be included upon a flexible or stretchable electronic substrate, the electronic substrate configured to interface the sensing tips with the anatomy as well as to electrically connect one or more sensing tips, or the like with a controller, a control system, an operator, a graphical user interface, a display, or the like.

A controlled nerve ablation system in accordance with the present disclosure may include one or more microfingers.

To this effect, a microfinger array microsurgical tool is disclosed herein. Any element in the microfinger array may include a sensing tip in accordance with the present disclosure to interact with the local anatomy during a surgical procedure.

The microfinger array may be advantageous for accessing very small anatomical sites within a body, perhaps through or adjacent to tortuous vessels, deep into an organ, in tissues nearby a ganglion of interest, etc.

In aspects, a microfinger array may be arranged in a surgical tool in accordance with the present disclosure such that one or more of the microfingers may substantially independently interface with the adjacent tissues. Thus if an array of microfingers is placed against a rough or otherwise uncontrolled surface, each microfinger may be able to contact, maintain a controlled bias force against, substantially embed an associated sensing tip into, and/or substantially maintain contact with the surface during use, even if the microfinger array is dragged along the surface as part of a procedure, during movement of the surface, etc. Such independently adjustable microfingers may be advantageous so as to maintain a known interfacial pressure, especially while monitoring, stimulating and/or ablating the tissue with the microfingers. Such independently adjustable microfingers may be advantageous to substantially embed an associated tip (i.e. an associated sensory tip) into an adjacent tissue during a procedure.

By microfinger is meant a substantially curved finger like member (i.e. with curvature at one or more points along the length thereof, with multi-axial curvature, etc.). Such microfingers may generally have a characteristic width (although may be of any cross sectional makeup). The microfingers may generally have characteristic widths on the order of approximately 1 mm, 0.5 mm, 0.1 mm, 0.05 mm, 0.01 mm, or the like. In one non-limiting example, one or more microfingers may include a Nitinol structure (e.g. a wire, a ribbon, etc.) with characteristic width of approximately 100 um, approximately 50 um, approximately 25 um, etc.

In aspects, one or more regions of a microfinger in accordance with the present disclosure may be selectively coated with an isolation layer (e.g. an oxide layer, a dielectric coating, a polymer layer, a lubricious layer, etc.). In aspects, such an isolation layer may be selectively applied to regions of the microfingers (i.e. so as to create isolated regions and sensitive regions thereof).

In aspects, the microfingers may be configured so as to deploy and/or bias against one or more adjacent tissue structures during a procedure and may be used to contactably sweep the local anatomy, for purposes of sensing, stimulating, and/or ablating during a surgical procedure. In aspects, one or more microfinger dimensions and structure may be designed so as to provide substantially uniform and predictable bias forces on the adjacent tissues over a wide range of movements and dimensional variation.

In aspects, an array of microfingers in accordance with the present disclosure may be configured so as to sufficiently collapse down into a delivery catheter while expanding radially outwards upon deployment so as to form a controllably biased contact within a tubular anatomical structure (e.g. an artery, a vein, an intestinal wall, etc.) or for convenient delivery to a surgical site (e.g. within tissues surrounding a renal artery, renal vein, etc.).

In aspects, one or more microfingers in accordance with the present disclosure may be configured into the shape of a wire basket, a mesh-like structure, or the like. In aspects, one or more regions of such microfingers may be patterned with an isolation layer, so as to direct signals over the microfingers, towards associated sensing tips, to provide communication between associated sensing tips and control electronics, to control one or more mechanical properties thereof, or the like.

Such a configuration may be advantageous for accessing tight anatomical spaces of interest (e.g. small vessel walls, accessing regions of the body with minimal damage, etc.), while also maintaining consistent contact forces at a surgical site during a procedure, substantially embedding one or more sensory tips into a lumen wall, tissue structure of interest, substantially isolating one or more sensing tips from an adjacent fluid, or the like.

In aspects, a microfinger array in accordance with the present disclosure may include a plurality of fingers, one or more such fingers configured to interface with the surrounding tissues and biased radially outwards from a deployment site (e.g. a guide wire, a catheter, etc.). In aspects, the microfinger array may be deployed via longitudinal retraction of a restraining shell (i.e. a restraining layer in the catheter), via application of heat or current (i.e. in the case of a shape memory microfinger, etc.), via projection of the microfinger array out of a delivery catheter (i.e. by advancing the microfinger array beyond the tip of the delivery catheter, etc.).

In aspects, one or more microfingers may include a spring-like wire element (e.g. Nitinol, spring steel, etc.) and/or may include composite structures including a spring-like element to provide a bias force so as to push the tip and/or one or more regions of the microfinger towards the wall of a vessel into which it is placed (i.e. towards a surface, a lumen wall, a vessel wall, etc.).

In aspects, a microfinger may include a Nitinol structure, optionally configured for passage of current flow, to and from the surrounding tissues, and/or communication of electrophysiological information between an associated sensing tip and a connected microcircuit. In aspects, the Nitinol structure may be configured such that, when an RF pulse is applied therethrough towards the surrounding tissues, the Nitinol structure may retreat from the tissues after a predetermined amount of energy has passed therethrough, upon reaching a predetermined temperature, or the like. Thus the Nitinol structure may provide an inherently controlled method for applying a quantum of RF energy to the surrounding tissues. Such a configuration may be adapted for use simultaneously, additionally, alternatively and/or in combination with one or more of the other aspects described in this disclosure.

In aspects, each finger in the array may move somewhat independently of the others such that all fingers may maintain contact with a vessel wall, a target tissue, or the like, during a procedure.

Such a configuration may be advantageous for maintaining robust contact with the interior and/or exterior walls of a tortuous anatomical site (e.g. a plaque filled artery, a tortuous vein, a damaged vessel, etc.) within the body. Such a configuration may be advantageous for maintaining robust contact with the walls of a lumen, surgical site, etc. while performing a procedure (i.e. scanning a surface with one or more microfingers, dragging a microfinger along a surface, monitoring a tissue site, ablating a tissue site, etc.) or during periods of relative movement (i.e. in the presence of organ movement, perhaps due to physiological processes, stresses related to biorhythms, breathing, blood pressure variation, etc.).

In aspects, at least a portion of the microfingers may be formed as spirals such that torsion applied at the operator end of the catheter may rotate the microfingers about the central axis of the lumen (i.e. blood vessel, etc.), thus allowing one to sweep the contact of the microfingers around the entirety of the vessel interior. Such movements may be advantageous for analyzing the adjacent tissues, selectively mapping and ablating the tissues, etc. In one non-limiting example, a microfinger array in accordance with the present disclosure may be swept circumferentially along the wall of a vessel, optionally starting and stopping so as to analyze the local tissues. If a suitable site for ablation is detected, the microfinger array may be used to ablate the tissues as well as monitor the ablation process to ensure controlled ablation is achieved before continuing with the sweeping procedure.

In aspects, the microfingers may be formed slightly off axis to a delivery catheter, such that relative axial movement of an overlying sheath may be used to retract the microfingers into the sheath or conversely to deploy them towards the anatomical site. Additionally, alternatively, or in combination, off axis arrangements may provide the capability to sweep the microfingers circumferentially along the anatomical site via applying torsion to the guide wire, delivery wire, and/or catheter to which they are attached.

Such a configuration may be advantageous for simultaneously mapping and selectively ablating an anatomical site during a surgical procedure.

Furthermore, such a configuration may be advantageous for working upon an anatomical site, while maintaining flow of fluid therethrough (i.e. as opposed to an occlusive tool, which may block flow during expansion thereof).

In aspects, one or more microfingers may be provided with highly miniaturized and flexible structure so as to more easily access highly restricted anatomical sites within the body, and/or so as to reach surgical sites of interest with minimal damage to the surrounding tissues.

In aspects, one or more microfingers may include one or more sensing tips in accordance with the present disclosure for capturing information from the local surgical site. Some non-limiting examples of sensing options include temperature sensors, electrodes, strain gauges, contact force sensors, combinations thereof, and the like. For purposes of discussion, a sensing tip may also be referred to as a microsensor.

The sensing tips may be configured to elucidate a range of key information during a procedure. Some aspects are discussed in more detail below.

Bioimpedance between one or more microfinger tips may be used to determine the degree of contact between the finger tips and the anatomical site, the water content of tissues between the microfinger tips, the state of tissues between the microfinger tips, as well as potentially the bias force between the finger tips and the anatomical site. Such information may be useful in determining when adequate contact and to gauge how much current should be applied to an anatomical site during an ablation procedure.

Mechanomyographic information may be obtained from fingertips during a procedure as determined by slight changes in an associated strain measurement and/or contact force measurement (e.g. via direct force measurement between the tip and the local anatomy, and/or via changes in the deformation of the microfinger as measured by an associated micro strain gage attached thereupon).

Evoked potential monitoring at or between one or more finger tips, may be used to map nervous response, electromyographic response, extracellular potentials, local field potentials, evoked potential, etc. along the wall of the local anatomy (e.g. vessel wall, organ wall, etc.) or within tissues associated with the surgical site, etc. Such information may be advantageous for selecting tissues on which to perform a surgical procedure (e.g. an ablation procedure, a biopsy, a stimulation procedure, a chemical delivery event, etc.).

The tone of the adjacent tissues may be determined by combining strain and/or force measurement of the microfingers while applying an excitation to one or more microfingers (e.g. optionally clockwise torsion to advance the microfingers and small counterclockwise torsion to measure the tone of adjacent tissues, a vibratory exciter in combination with contact and/or microfinger strain measurement, etc.).

Such tone measurement may be useful in determining the local stiffness of tissues in contact with the microfinger array (e.g. so as to determine the type of tissue adjacent to one or more microfingers, to locate plaque, to locate a cancerous tumor, etc.).

Stimulation and sensing from one or more microfingers in the microfinger array may be used to elicit nervous function of local anatomy. Such information may be used to select tissues for a surgical procedure, to determine the degree of progression of a surgical procedure (e.g. a degree of ablation during RF surgery, effect of a chemical substance delivered into the surrounding tissues, etc.). Directional stimulation and sensing may be used to selectively treat only nerves that are configured to send signals in the preferred direction (i.e. via combination of stimulation and/or sensing from a plurality of sensing tips, sensing sites, etc.).

In aspects, one or more microfingers may include the capability to apply/receive an RF current to/from the surrounding tissue.

Such RF currents may be applied between one microfinger in the array and an (optionally) distant counter electrode, between two or more microfingers in the array, to a extracorporeal patch on the body, etc.

In aspects pertaining to multiple microfinger RF current passage, the local impedance of each microfinger may be altered so as to control the current delivered thereto.

In aspects pertaining to multiple microfinger RF current passage, the local current flow through each microfinger may be monitored so as to determine the path of the RF current flow, to ensure no leakage currents are detected, etc. Such information may be used to more precisely control the delivery of RF currents to the local anatomy during an ablation procedure.

In aspects, prior to, during, and/or after the RF current is applied to the surrounding tissues, one or more microfingers may be configured to monitor a physiological parameter (e.g. water concentration, tone, blood oxygen saturation of local tissues, evoked potential, one or more local field potentials, stimulation/sensing of nervous activity, EMG, temperature, etc.) to determine the extent of completion of the intended surgical procedure.

In aspects, the bioimpedance between one or more microfingers in the array may be used to determine changes in the structure of the adjacent tissues during an ablation procedure. Such information may be useful in determining the extent of the ablation procedure, char accumulation, changes in tissue impedance, etc.

In aspects, bioimpedance measurements may be correlated with nerve damage data, perhaps obtained during prior surgeries or obtained during specific testing procedures, such that changes in local bioimpedance data may be used during a surgical procedure to determine the extent of the procedure. Such a configuration may be advantageous in the case that the surgical procedure itself overwhelms the local electrophysiological activity to the extent that neurological monitoring may be hindered for a prolonged period of time after the procedure has been completed.

In aspects, one or more microfingers may be configured to monitor local electrical fields during an ablation procedure in order to better determine the current flow path through the adjacent anatomy, perhaps connected to a warning system to indicate to an operator when the ablation field is insufficient for achieving the intended goal, to assist with the direction of energy towards the intended surgical site, to conserve energy, etc. Such a configuration may be advantageous for avoiding unnecessary damage to the tissues during a misfired ablation session.

In aspects, a system in accordance with the present disclosure may include an embolic net to capture char that may form during the ablation procedure. Such netting may be advantageous for preventing surgically related emboli from traveling throughout the body after the surgery.

In aspects, the system and/or microfingers may include a coolant delivery system (e.g. a saline delivery system) in order to cool the microfingers during and/or after an ablation procedure. Such coolant delivery may be advantageous for minimizing char and excessive damage associated with an ablation procedure. In aspects, such coolant delivery may be part of a cryogenic surgical procedure (i.e. cryoablation), or the like.

In aspects, the system may include multiple microfinger arrays, perhaps located at specific radii from each other such that when sweeping a tubular anatomical site (e.g. a vessel), the bias forces may be reasonably maintained between the microfingers and the tissue walls.

In aspects, one or more microfingers may include an exposed electrode area (i.e. as part of an electrode based sensing tip) that only touches the walls of the adjacent anatomy. Such a configuration may be advantageous for minimizing current flow into the adjacent fluids within the vessel (i.e. to substantially isolate the electrode from fluids within a vessel, an organ, etc.), to better control RF current flow in the vicinity of the electrodes, minimize conductivity between the exposed area and the surrounding fluid, so as to substantially embed the exposed electrode area in to the wall of the adjacent anatomy, etc.

In aspects, one or more microfingers may include one or more active material elements. Control signals delivered to the active material element may help to bias the microfingers towards the intended surgical site, actively control the contact forces between finger tips and the surgical sites, etc. Some non-limiting examples of active materials that may be suitable for application to one or more microfingers include shape memory materials (e.g. shape memory alloys, polymers, combination thereof), electroactive polymers (e.g. conjugated polymers, dielectric elastomers, piezoelectric polymers, electrets, liquid crystals, graft elastomers, hydrogel actuators, etc.), piezoceramics (e.g. amorphous piezoceramics, single crystals, composites, etc.). In addition the active material may be used as a vibratory exciter and/or mechanical probe, for use in monitoring the tone of the adjacent tissues (see above), alternatively, in addition or in combination, to cause vibratory/ultrasonic ablation and/or local heating to the tissues. In such aspects, the active material may be included along the length and/or over a region of the microfinger (i.e. so as to influence the shape of the microfinger during contraction or expansion of the active material).

In aspects, one or more microfingers may include an electrical shield such that the microfinger tips are effectively shielded from other currents flowing through an associated catheter, the body, etc. during a procedure.

In aspects, one or more elements of a microfinger based catheter may include a bidirection switching network, micro amplifier array, a sensory front end, combinations thereof, or the like in order to amplify sensed signals as close as possible to the anatomical interface, to switch the function of a microfinger tip between sensory, stimulatory, and/or ablative functions, perform combinations thereof, or the like. In aspects, the circuitry may be included in the delivery wire within the catheter of the system. In such aspects, the circuitry may be coupled to one or more microfingers and/or sensing tips each in accordance with the present disclosure, and a secondary signal acquisition circuit, a digital communication block, a controller, an RF signal generator, combinations thereof, and the like.

In aspects, a bidirectional switching network may be used to enable bifunctional stimulation/sense capabilities in one or more microfingers, etc. The switching network may be included in a local amplifier array, as a flexible circuit, or silicon die interconnected to or placed upon one or more microfingers, etc. Alternatively, additionally, or in combination, an extracorporeal circuit element may be coupled to the switching network and/or microfingers, sensing tips, etc. and to a controller included within a surgical system including a microfinger array in accordance with the present disclosure.

In aspects, a micro amplifier array may be used to preamplify the signals obtained from one or more sensory aspects of the microfingers, so as to improve the noise signature, etc. during use. The microamplifier may be coupled to the catheter, embedded into the catheter, embedded into one or more microfingers, etc.

In aspects, one or more microfingers in accordance with the present disclosure may be provided such that they are sufficiently flexible so as to buckle, or change orientation during back travel, so as to prevent puncture of the local anatomy. A configuration as outlined in this non-limiting example may be advantageous for providing contact with the local anatomy without significant risk of damaging the adjacent anatomy (e.g. puncturing a vessel wall, etc) which may be a concern with stiffer, more traditional structures. Such microfingers may include a characteristic width of less than 200 um, less than 100 um, less than 50 um, less than 25 um, less than 10 um.

In aspects, one or more microfingers in accordance with the present disclosure may include a substantially hyper elastic material (e.g. formed from a memory alloy material, a superelastic material, a spring steel, etc.) so as to effectively deploy from a very small deployment tube/catheter and expand outward to accommodate a large range of vessel diameters or changes in shape during deployment. Such a configuration may be advantageous in so far as a small number of unit sizes may be suitable for treating a wide range of anatomical structures. In addition, the designed curvature and form of a microfinger may be substantially chosen so as to further enable a wide deployable range of movement.

A surgical tool including a plurality of microfinger arrays (i.e. clusters of microfingers, fans of microfingers, etc.) may be employed so as to determine physiological response more remotely from an intended surgical site than may be available within a single array. Aspects of the disclosed concepts may be employed along the same lines by extending interactions between microfingers within an array, to inter—array interactions. In aspects, a surgical tool including a plurality of clustered microfinger arrays may be advantageous to analyze one or more anatomical sites simultaneously from a plurality of sites (macroscopically separated sites). In aspects, two microfinger arrays may be arranged along a catheter based surgical tool, so as to interface with the walls of a lumen, at two or more longitudinally separated distances, between a surgical site of interest and a (somewhat) remote location, or the like. Physiological sensing from multiple microfingers may be advantageous for determining the extent of neurological traffic between the plurality of sites, determine the direction of traffic, determine if traffic from one direction or the other is blocked (i.e. after a surgical procedure, after RF current application, after a denervation procedure, etc.). Such configurations and methods for determining the state of a plurality of anatomical sites is further disclosed throughout the text and appended figures of this disclosure.

In aspects, a system in accordance with the present disclosure may be used to monitor physiological activity associated with a surgical site prior to, during and/or after a surgical procedure is applied thereto. Some suitable examples of surgical procedures include an RF ablation, Argon plasma coagulation, laser ablation, ultrasonic ablation, cryoablation, microwave ablation, abrasion, biopsy, delivery of a substance (e.g. a chemical, a drug substance, a neuromodulating substance, a neuroblocking substance, an acid, a base, a denervating agent, etc.), combinations thereof, and the like. The local physiological activity (e.g. nervous activity, blood perfusion, tonal changes, muscular sympathetic nerve activity, etc.) may be monitored with one or more sensors (sensing tips, microfingers, etc.), perhaps in combination with one or more physical sensors (i.e. temperature sensors, pressure sensors, etc.), and/or associated stimulators each in accordance with the present disclosure. Additionally, alternatively, or in combination, a technique for assessing one or more physiological properties and/or states of an associated surgical site may be employed. Such techniques include assessing values and/or trends in bioimpedance, blood pressure, tissue oxygenation, tissue carbon dioxide levels, local temperatures, combinations thereof, changes thereof, and the like.

In aspects, the system may include a substrate onto which the sensing tips may be placed. Such a substrate may be formed from a balloon wall, a mesh, an interwoven ribbon array, a cloth, a clamp face, a hook face, etc. In aspects, the substrate may include stretchable and/or flexible electronic materials.

Electrical interconnects may be formed from carbon nanotubes (e.g. SWNTs, MWNTs, etc.), nanowires, metallic wires, composites, conductive inks, patterned versions thereof, combinations thereof, and the like.

In aspects, a portion, or all of the substrate and/or an associated substrate carrier film may be formed from polyurethane, a silicone, a general elastomer, silk fibroin materials, combinations thereof, or the like. Inclusion of microporous or fibrous substrates may be advantageous to allow the substrate or substrate carrier film to adhere to the adjacent tissues via capillary effects (i.e. tendencies to wick fluid from adjacent tissues into the substrate). In aspects, the thickness of films formed from the material may be less than 30 um thick, less than 20 um, less than 10 um, less than 4 um, less than 1 um. Composites of somewhat stiffer materials (such as polyimide, PET, PEN, etc.) and somewhat softer materials (e.g. silicones, polyurethanes, thermoplastic elastomers, etc.) may be used to compromise between overall structural stiffness and conformal capabilities of the substrate.

In aspects, patterned overcoats and/or composite layers may also be used to expose electrode materials and/or sensing tips to the surrounding tissues in the vicinity of measurement regions, etc.

In one non-limiting example, the substrate may be at least partially formed from a silk material (e.g. *Bombyx mori* cocoons). The material may be processed to remove sericin (which may cause undesirable immunological response) using methods known in the art. The resulting material can be solvent cast into shapes and crystallized to form self-supporting structures.

In aspects, adaptive temperature estimation may be used to better control the RF ablation process. Such techniques may be supported by use of a surgical tool in accordance with the present disclosure, including one or more sensing tips configured with temperature and/or bioimpedance monitoring aspects. Modeling of changes in local bioimpedance may be related to local temperature changes during the ablation process. Such measurements as well as local thermoconductive properties, tissue thermoconduction, etc. may also influence the rates at which a local ablation process may take place (i.e. as related to a thermal ablation process).

In aspects, a system in accordance with the present disclosure may include one or more microsensors for monitoring nervous activity and/or related physiological activity during the RF ablation process. Some examples of suitable monitoring techniques include electromyography (EMG), muscle sympathetic nerve activity (MSNA), mechanomyography (MMG), phonomyography (PMG), extracellular potentials, local field potentials, combinations thereof, and the like. Mechanomyography (MMG) measures the force created by local muscle contractions caused by associated neural activity. Phonomyography (PMG) measures low frequency sounds associated with movement generated by associated neural activity. Traditionally, techniques such as MMG and PMG have been employed on externally accessible nervous and muscular tissues. One advantage of such techniques is that they may not be as easily affected by local electrical noise as EMG and the effects of the nervous activity may be generally sensed farther from the associated nerve than with electromyographic techniques.

Alternatively, additionally or in combination the ascribed sensing techniques may be combined with stimulation from local sources in accordance with the present disclosure. Such stimulation and sensing may be advantageous in determining functionality of local nerves without the need to listen to complex biologically generated nervous activity. Furthermore, combined stimulation and sensing may be advantageous for determining functionality of a local nerve in real-time during a denervation and/or ablation procedure (e.g. the successive stimulation and sensing may be used to determine the degree of neurological block and/or neuromuscular block there between). In aspects, such functionality as well as directionality of the nerve signal propagation (e.g. efferent, afferent, etc.) may be more easily determined through use of combined local stimulation and sensing.

In aspects, one or more patterns of nerve stimulation may be used to determine the function of the local nerve structures as well as one or more aspects of neurological block and/or neuromuscular block that may be caused by the surgical procedure (e.g. ablation), anesthesia, heating, chemical delivery, a related condition, etc.

In aspects, a single stimulation may be applied to elicit maximal response from the associated nerve at frequencies of less than 10 Hz, less than 1 Hz, less than 0.1 Hz. The downstream response as measured by any of the described techniques will depend on the frequency with which the stimuli are applied. In aspects, in order to allow for complete recovery of the nerve between stimulations, a frequency of less than or equal to 0.1 Hz may be advantageous.

During RF ablation of an associated nervous structure, the evoked electrical and/or muscular responses may be dramatically affected. Such changes in the response may be useful in determining the state of the denervation procedure. Thus they may be advantageous to determine the exact degree of RF energy that must be applied to a given structure in order to cause sufficient denervation as desired by a surgical procedure. Such an approach may be advantageous to limit damage to surrounding tissues caused by the denervation procedure, to ensure suitable denervation has been achieved, to determine which nerves are affected by the procedure, to control the extent of a denervation procedure, etc.

Another technique for stimulation and sensing of the nervous response includes applying a rapid succession of pulses followed by a period of inactivity. Pulse trains may be used to gradually force a nerve into a blocked state. The rate at which a nerve enters a blocked state and later recovers therefrom may be a suitable indicator of the overall health and functionality of the nerve (i.e. a suitable metric for determining how a procedure has affected that nerve).

In aspects, the sensing of the nervous response may not need to be local to a surgical site, but rather downstream (in the sense of the flow of an associated nervous signal) from the site. Such sensing of the nervous response may be advantageous for determining the progression of a particular form of communication past a surgical site (i.e. afferent, efferent traffic, etc.).

In aspects, various mapping techniques may be applied to the surgical site, before, optionally during, and/or after a surgical procedure. Some mapping techniques as used in cardiac interventions include pace mapping, activation mapping, entrainment mapping, and substrate mapping. It may be feasible to adapt such techniques for use in the intended application and/or a system in accordance with the present disclosure. In general, these techniques may complement each other in localizing where amongst a surgical site to target the ablation procedure.

In aspects, the micro fingers and/or associated sensing tips may be arranged in a polar configuration as an array of arches (i.e. an array of thin, arch-like elements each extending radially outwards from a central axis). The arches may be attached at each end, a first end connected to an axially oriented draw wire and the other end attached to a collar. The arches may be collapsed and/or expanded radially by extending and/or retracting the length of the draw wire between the first end and the collar respectively. The draw wire may extend through the surgical tool to the operator or a machine, where force on the draw wire may be used to achieve this function (i.e. deployment or retraction of the arches). Thus the arches may be provided in a substantially collapsed state (i.e. with small overall diameter) for easy delivery to the surgical site. Upon delivery to the surgical site, the draw wire may be retracted, perhaps automatically and/or with the help of an operator, and the arches may be extended radially outwards, so as to contact the adjacent tissues of the vessel, or to fan out into the tissues of interest, etc. In aspects, such a procedure may be used to bias the array of sensing tips and/or micro fingers towards the walls of the vessel while maintaining blood flow therethrough.

Alternatively, additionally, or in combination the arches may be deployed at a surgical site by removal of a restraining sheath (perhaps by retraction), by dissolution of a restraining element (e.g. an adhesive, an electrochemically destructible member, etc.), via thermal self-expansion of one or more elements of the arches, by combinations thereof, or the like.

Additionally, or in combination to the aspects described herein, the surgical system may be configured to monitor one or more physiological parameters at one or more locations in the body remote from the surgical site. Some non-limiting examples of what may be monitored include water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive (e.g. bursts per minute, bursts per heartbeat, etc.), tissue tone, blood flow (e.g. through an artery, through a renal artery), a blood flow differential signal (e.g. a significantly abnormal and or sudden change in blood flow within a structure of the body, a vessel, an organ, etc.), blood perfusion (e.g. to an organ, an eye, etc.), a blood analyte level (e.g. a hormone concentration, norepinephrine, catecholamine, renine, angiotensin II, an ion concentration, a water level, an oxygen level, etc.), nerve traffic (e.g. post ganglionic nerve traffic in the peroneal nerve, celiac ganglion, superior mesenteric ganglion, aorticorenal ganglion, renal ganglion, and/or related nervous system structures), combination thereof, and the like.

In aspects, a surgical system in accordance with the present disclosure may include one or more elements to monitor physiological activity and/or analyte levels (e.g. a hormone level), in and/or near to one or more portions of a gland, an endocrine gland (e.g. an adrenal gland, an adrenal medulla, etc.), etc.

In aspects, a multi catheter surgical system may be employed, each catheter in accordance with the present disclosure. In one non-limiting example, one or more first catheters may be used to probe and/or ablate tissues at a first surgical site (e.g. an artery, a renal artery, a left renal artery, a first nerve structure, a nerve plexus, etc.) while one or more second catheters may be configured to monitor one or more physiological parameters elsewhere in the body (e.g. in an alternative artery, a vein, further along the first nerve structure, in an organ, at a lymph node, at a ganglion, etc.), perhaps to determine the effect of the surgical procedure thereupon. In one non-limiting example, the catheters may be inserted into the same or closely positioned entry points into the body (e.g. the femoral artery, iliac artery, radial artery, femoral vein, transcutaneous entry point, etc.). Such a configuration may be advantageous for providing a minimally invasive surgical tool to perform the surgical procedure (e.g. a sympathectomy, a renal sympathectomy, a neuromodulation procedure, etc.).

Some further aspects relating to systems and methods for adjusting (temporarily and/or permanently) nerve function, while substantially minimizing collateral damage to adjacent structures via endoscopic tools and methods are now discussed. References made to ablation may be considered to refer to a general surgical procedure (to cut, heat, cool, excise, chemical delivery, etc.) on a tissue.

Herein the general reference to electrodes, sensors, etc. may equally pertain to sensing tips in accordance with the present disclosure.

The system may include a clamping tool. The clamp may be used to simultaneously hold and interface with adjacent tissues. The clamp faces may include an array of electrodes and/or sensing tips on one or more sides, the electrodes arranged so as to interface with an anatomical site against or around which the clamp is placed. The array of electrodes may be used to interface circumferentially and axially with the local tissues, so as to select ablation sites, validate ablation success, sense local neural activity, stimulate and sense, etc.

Electrodes in the array may be used to stimulate, sense, and/or ablate local tissues and/or monitor nervous activity before, during, and/or after a related surgical procedure or ablation process.

In aspects, a surgical tool in accordance with the present disclosure may include a switch array in accordance with the present disclosure, optionally with amplifiers such that one or more electrodes could be configured for stimulation, ablation, and/or sensing. In aspects, the tool may include electronics to monitor bioimpedance between one or more electrodes (i.e. so as to determine when the tool is adequately clamped onto the intended anatomical structure, etc.).

In aspects, the tool may include electronics for automatically terminating an ablation signal when a change in the sensed nervous activity is detected. In one non-limiting example, a pulsatile stimulation is applied to one side of the ablation zone, perhaps during the ablation process and/or between ablation pulses (and/or perhaps intermixed with the ablation pulses). Another electrode may be placed to the opposing side of the ablation zone so as to monitor nervous response before, during and/or after the ablation procedure.

In one non-limiting configuration, individual electrodes in the array may be preconfigured during a procedure so as to provide a particular function, sense, stimulate and/or ablate and necessitated by the present procedural context.

One or more electrodes in the array may be a monopolar electrode or part of a bipolar pair. In one example, two or more electrodes may be arranged into pairs, multi-polar interconnects, etc.

The clamp may include electrodes and/or shields placed to the outer surface of the clamp. In the case of electrodes, the readings from these electrodes may be used to balance and/or cancel out macroscopic or environmental action potentials and/or noise from the local microelectrode readings taking place at the clamp-tissue interface. This approach may be used to lower the noise floor and improve the sensitivity of the micro-electrodes on the inner face of the clamp surfaces.

The electrodes may be configured so as to protrude from the clamp face (e.g. via emboss, plating, filament, matted morphology, application of microfiber structures thereupon, etc.). In aspects, one or more of the microelectrodes may be embossed so as to better bias the interfacing aspects towards the tissue during a procedure. This may be advantageous to ensure that each electrode applies adequate pressure to the adjacent tissues and/or to improve the chances of tissue contact with a plurality of the electrodes A method for treating a surgical site with a clamp tool in accordance with the present disclosure may include one or more of locating the surgical site of interest; latching onto the surgical site with the clamp tool; monitoring electrophysiological activity (e.g. neurological activity, MSNA, etc.) using one or more of the electrodes included on at least one face of the clamp to determine a reference signal; applying a denervation signal (e.g. ablation, abrasion, current, light, etc.) to the tissue site for a predetermined timeframe or delivered bolus of energy; monitoring electrophysiological activity using one or more electrodes to determine an updated signal; and/or comparing at least a portion of the reference signal or a metric derived therefrom with the reference signal or a metric derived therefrom in order to determine the extent of the denervation or neuromodulation procedure.

The method may include monitoring with different electrodes for determining the reference and the updated signals, determining a bioimpedance between electrodes during and/or after the latching, or the like.

The method may include the application of multiple pulses, monitoring other physiological signals, algorithmically combining such signals to generate the updated signal, extracting a metric from the neural activity and/or additional physiological signals, confirming a change in the electrophysiological activity, and the like.

A method for determining the functionality, directionality, location of and/or the extent of nerve function degradation before, during and/or after a surgical procedure may include stimulating a one or more nerves located at a proximal and/or distal location on an organ (e.g. a kidney, a renal artery, a gland, etc.) in a body; monitoring an evoked response at a location distal and/or proximal to the location of the stimulation; evaluating the signal quality, spectral content, etc. related to the evoked response and/or changes in the evoked response during and/or after the surgical procedure. The method may be performed with one or more surgical tools each in accordance with the present disclosure.

In aspects, one or more of the methods in accordance with the present disclosure may include stimulating the stimulation location (e.g. a nerve) with one or more pulse trains, the pulse trains including one or more pulses with a predetermined spectral content (e.g. pulses centered around 10 Hz, 50 Hz, 100 Hz, 500 Hz, etc.) at one or more locations proximal and/or distal to the surgical site.

The pulse train may be applied locally to the nervous structure, with an amplitude of generally 1.5× the voltage required to obtain a maximal amplitude compound action potential (CAP), with pulse duration of generally between 0.05 and 0.5 ms and interval of between 2 ms (for 500 Hz spacing) to 100 ms (for 10 Hz spacing). The pulse train may include one or several such pulses, perhaps even spaced with alternative timing over the application of the pulse (so as to better scan through a frequency range of interest). The corresponding nervous response may be monitored at another location on the vessel or in the body. Such response may be monitored with a gain of generally 500 to 5000 and generally over a frequency band of 0.1 Hz to 10 kHz. This configuration may be used to evaluate the overall health and/or capability of the nervous structure connecting the stimulating location and the monitoring location.

During a surgical procedure, early indication of functional alteration to the nerve structure may be determined by monitoring for a change in the properties of the sensed signal (e.g. a change in latency, amplitude, conduction velocity, spectral content, etc.). In aspects, an ablation pulse may be applied to the nerve between the stimulatory and monitoring locations. A change in the properties of the sensed signal (e.g. a decrease in high frequency content therefrom, a change in latency, change in amplitude, etc.) may be an early indicator that the pulse is being applied properly to the nervous structure there between. In addition, additional pulses may be applied and the response monitored in order to observe the nerve response through to a sufficient state of functional alteration, such as during an ablation procedure.

Monitoring may continue during a follow up period immediately after the surgical procedure, and/or during a longer term period (e.g. hours, days, weeks, etc.). Such follow up may be used to determine and/or prognosticate on the longevity of the surgical intervention. Such follow up may be performed with an implantable device in accordance with the present disclosure.

In aspects, one or more of the techniques disclosed herein may be used to identify the particular neurons of interest, or to ensure that the correct neurons are being treated surgically (as well as to ensure that the extent of the treatment is acceptable). Such identification may involve monitoring a level of neurological activity on the sensed nerve(s) to determine if the levels are outside of the norm (i.e. as compared with other sites in the body, an activity metric for the patient population or a subset thereof, etc.).

A method for generating a follow up schedule following a surgical procedure may involve monitoring the neurological activity of the site for a period of time (e.g. hours, days, weeks, etc.) after the surgical procedure; trending the neurological activity to create a metric relating to changes therein over the period of time; and predicting recurrence data (e.g. probability of recurrence, a timeframe of recurrence, etc.) therefrom; and generating a follow up schedule dependent upon the recurrence data.

In aspects, one or more alternative clamp configurations may be used to alter the pressure profile at the tissue interface between the clamp and the anatomy, such changes in shape may include clamps with curved surfaces, soft structures to limit forces applied to the local anatomy, etc. In one non-limiting example, a clamp element may be formed from a bistable cantilever, a bistable laminate, etc. such that the clamp element may have a first form (e.g. a substantially straight form) for delivery to the anatomical site and take on (e.g. through electrical and/or mechanical triggering, etc.) a second form (e.g. a curved form) for more easily interfacing with an adjacent anatomical structure.

In aspects, a hook-like tool in accordance with the present disclosure (e.g. with one or more sensing tips thereupon, etc.) may be used to make consistent and controlled contact with the target anatomy (so as to access large surface of the anatomy with a simple tool). A soft hook-like structure with tissue interfaces (electrode arrays, sensing tips, etc.) fashioned towards the inner surface could be used to delicately contact the key anatomy during a surgical procedure (e.g. such as contact the outer surface of an artery, a renal artery, etc. during a denervation procedure). The hook may include a quick release (e.g. a mechanical quick release, an electroactive material quick release, etc.) for simple removal from and/or positional correction along the anatomy (e.g. a vessel), during, and/or at the conclusion of a surgical procedure.

A sensing tip in accordance with the present disclosure may be attached to the hook to enable sensing and/or interfacing with the adjacent tissues during an associated surgical procedure.

Axially (in the sense of along an elongate anatomical structure adjacent to the tool) spaced electrodes and/or arrays may be used in concert to, perhaps, more precisely stimulate and/or sense the neurological behavior along the anatomical structure before, during and/or after a surgical procedure.

Soft clamping structures and/or hook structures may be used to controllably interface with the tissues, applying contact pressures that are just suitable for ablation procedures while minimizing the changes of unnecessary pressure induced neural blockage during an associated surgery.

In aspects, a method for searching for a nerve of interest on the wall of a vascular vessel may include applying a point pressure on the wall of the vessel while monitoring distal and/or proximal nervous activity (e.g. monitoring, and/or stimulation and sensing on either side of the point pressure probe). Changes in the observed signals may be indicative of pressure induced neural block due to the applied point pressure (i.e. thus identifying the location of the neural anatomy in question).

In aspects, the method may include clamping the vessel with a flat, smooth backing plate (e.g. a flat soft surface, etc.) and a protruding probe on the adjacent wall, to increase pressure at the interface between the probe and the tissues. The probe may be combined with an ablation electrode (thus providing colocation of the pressure application and the ablation zone). Multiple probes may be used together to deliver ablation along the length of a nerve or nerve bundle. In the case of multiple probes, the probes may be relatively placed onto the surface so as to optimize an ablation current passed there between.

Relating to nerve compression syndrome, acute nerve compression studies have shown some loss of nerve function through application of acute transverse pressure above 40 mmHg, and loss of all nerve function at pressure application above 50 mmHg. Other studies have shown functional block under transverse compression when a pressure of 30 mmHg less than diastolic pressure is applied and 45 mmHg less than the mean arterial blood pressure is applied to the nerve. Thus one or more components of the system (e.g. a clamp, an electrode element, a point pressure applicator, etc.) may provide pressure variation above and/or below these ranges in order to assess nerve function, location, etc. as described herein for the application of interest.

The point pressure applicator may be configured to operatively provide an oscillating pressure to the test site, to synchronize pulsatile pressure application with an array of probes, etc. so as to better orient a pair or array of probes for an ablation procedure.

The holding force of one or more surgical elements (e.g. a clamp, a hook, a loop, a point pressure applicator, etc.) may be controlled by various means including feedback via bioimpedance measurements, interfacial pressure sensors, micro-pulse oximetry based measurements, through flow and/or local perfusion measurements, via optically equipped sensing tips, combinations thereof, and the like. It may be desirable to control the application of force for various reasons such as causing signal inhibition via mechanical compression (nerve compression); for imposing a temporary nerve block during an associated procedure; to mask the underlying nervous activity during surgical site selection; to control one or more contact pressures and/or impedance for performing an associated ablation and/or monitoring procedure.

In aspects, a self-wrapping tool including a ringlet-like array of electrodes may be used to interface with an adjacent anatomical structure. The self-wrapping tool may include a thin (i.e. less than 100 um, less than 50 um, less than 10 um, less than 4 um thick) substrate with one or more electrodes attached thereupon. The self-wrapping tool may be substantially formed in a curved shape optionally including one or more microporous or fibrous substrates in order to provide surface tension based wrapping when the structure is placed against an anatomical structure (e.g. an organ, a vessel wall, a renal artery wall, etc.).

In aspects, a surgical tool system in accordance with the present disclosure may include a clamp tool and one or more self-wrapping tools both in accordance with the present disclosure. In accordance with one non-limiting example, two self-wrapping tools may be applied to a vessel at proximal and distal ends thereof, so as to monitor nervous activity and/or EMG signals during a procedure. A clamping tool in accordance with the present disclosure, perhaps including one or more bipolar electrodes may be clamped along the artery between the self-wrapping tools so as to apply an ablation procedure. The self-wrapping tools may monitor the nervous activity (either actively or passively) before, during and/or after the ablation procedure. The clamp may then be repositioned along the vessel for further treatment.

In aspects, a self-wrapping tool may include an electroactive polymer bimorph with electrode patches patterned to one surface to provide combined wrapping and biointerfacing capabilities. Upon placement next to a vessel a release current and/or charge may be applied or removed from the bimorph causing it to coil gently around the vessel wall (so as to circumferentially contact the vessel wall during use).

In aspects, a surgical tool in accordance with the present disclosure may include a means for applying a vacuum at sites in and around the electrodes. Such vacuum attachment may allow for very intimate yet gentle contact between the adjacent tissue surface and the electrodes during a procedure.

A self-wrapping structure in accordance with the present disclosure may have a range of microchannels to facilitate vacuum application thereto. Such microchannels may facilitate drawing the structure against the surface of an adjacent organ.

In aspects, a soft flexible structure in accordance with the present disclosure may be used in conjunction with a surface enhancement and/or wicking function (a hydrophilic material, a porous material, etc.) so as to draw fluid out from the target tissue surface and use the resulting capillary forces and surface tension to form a tight, intimate contact between the tool and the tissue suitable for neurovascular monitoring. This may be an option for long term placement (e.g. placing of an implantable component during a procedure for follow up, etc.). Silk structures included into the flexible structure may be suitable for providing this functionality, optionally with a first layer that can dissolve quickly and a second layer that may dissolve over the course of hours, days, weeks, etc.

In aspects, the flexible structure may include a medicament (e.g. a neural blocking agent, an anesthetic, lidocaine, epinephrine, a steroid, a corticosteroid, an opioid, alcohol, phenol, etc.). In aspects, the flexible structure may include a medicament releasing structure (i.e. a hydrogel structure) into which the medicament is bound, and may be released into the surrounding tissues over the course of minutes, hours, days, weeks, etc. In aspects, the hydrogel may be formed from a radical based crosslinking chemistry, a click crosslinking chemistry, etc.

In aspects, a surgical tool in accordance with the present disclosure may be configured to deliver a bolus of medicament into the tissues of interest. In aspects, The bolus may be housed in a hydrogel prepolymer, the surgical tool including means for polymerizing the hydrogel prepolymer in place after release to form a slow release structure, from which the medicament may leach into the surrounding tissues over a prolonged period of time (i.e. hours, days, weeks, months, etc.). In aspects, the hydrogel may include biodegradable chains, configured so as to allow for breakdown of the hydrogel over time, after being placed within the body of a subject.

In aspects, the structure may include a thin degradable support structure, the support structure may quickly dissolve in the presence of liquid (saline) such that it may be placed beside the vessel and wetted, so as to cause the remaining structure to flop down, wrap around, and/or otherwise contact the vessel walls.

In aspects, a self-wrapping device in accordance with the present disclosure may include a soft actuator including an elastomeric structure and one or more embedded tendons (e.g. polymeric and/or fibrous wires, etc.). Drawing of the tendons may be used to create an off axis compression of the elastomeric structure, causing bending of the self-wrapping device. A combination of tendons could be used to vary stiffness of the structure for better accessing a range of surgical sites. Thus the device may be able to wrap around the intended vessel, snake through a surgical site, etc. Similar effects could be achieved through use of vacuum application, an asymmetric pressurization, fluid movement, electroactive material components, etc. arranged or actuated throughout the self-wrapping device.

In aspects, the system may include one or more sensing tips (e.g. tonal measuring, optically equipped, electrodes, etc.) positioned to the interfacing side, i.e. the side that may interface with the adjacent anatomy.

Such soft configurations may be useful to establish a reliable, yet gentle contact to a vessel surface, intimately contouring to the surface of the vessel without applying excessive pressure thereto. Intimate yet soft contact may be advantageous for reading sensitive neurological signals without interfering mechanically with signal transmission thereof.

A surgical tool in accordance with the present disclosure may include one or more whiskers extending from a tool surface so as to reliably contact an adjacent tissue structure during a surgical procedure. The whiskers may include sensing tips such as electrodes, and the like. Additionally, alternatively, or in combination, a sensing tip in accordance with the present disclosure may include a whisker for interfacing with the adjacent tissues during a procedure.

In aspects, whisker penetration into an adjacent nerve bundle may be used to achieve more intimate contact thereto, as well as to better isolate electrodes from other macroscopic signal interference, etc.

In aspects, whiskers may be formed from microfibers, nanofibers, microneedles, nanoneedles, etc. In one aspect, one or more whiskers may be formed from a carbon structure, e.g. a carbon fiber, a carbon nanotube, etc. In aspects, the whiskers may be insulated along a portion of their length, with an electrically exposed region at the tip thereupon.

In aspects, one or more of the whiskers may be substantially hollow, configured so as to store a medicament in accordance with the present disclosure, to provide a means for delivery of a medicament in accordance with the present disclosure, or the like.

In aspects, a folding tool with a net-like portion may be employed to gently wrap a vessel and/or anatomical feature in accordance with the present disclosure. The net-like portion may include a range of sensor tips, electrodes and the like for sensing physiological parameters before, during and/or after a procedure is performed on the associated organ. The net-like portion may also include electrodes suitable for providing an RF ablation current to the tissues. The net-like portion may be configured so as to remain on the vessel after placement (for a long-term monitoring function and/or stimulation function). One or more members on the net-like portion may be formed from a shape memory material (nitinol, shape memory polymer, etc.) and thus may be used to actively wrap the vessel during placement (and/or selectively unwrap the vessel after a surgical or monitoring procedure), or the like.

In aspects, a boundary method for monitoring a surgical site during a surgical procedure may be employed. During this approach a plurality of sensor tips may be arranged in contact around a perimeter of a surgical region on a tissue surface, whereby the electrophysiological signals measured at locations along the surface may be used to determine the state of the tissues within the boundary. For purposes of discussion, the boundary may be effectively the distal and proximal ends of the vessel or the ends of the surgical area, when applied to a tubular organ of interest.

In aspects, a visual detection approach may be used in combination with, or in addition to any of the endoscopic approaches in accordance with the present disclosure. In aspects, visual assessment may be used to at least partially guide the surgical procedure. The feedback may be in the form of a visible, a near infrared, infrared spectroscopic, or similar camera system, used in conjunction with the surgical tools, so as to better visualize the vessel structure, identification of target anatomy (e.g. a nerve, nerve bundle, etc.) on the target organ (e.g. an artery, an organ, etc.), perhaps placement of tools onto the target anatomy, etc.

In aspects, a backlit vessel lighting system may be used to assist with visualizing the anatomy, locating target anatomy, etc.

In aspects, a system in accordance with the present disclosure may include a feature enhancing medium, to highlight targeted tissue species (e.g. highlight nerve tissues, etc.). The medium may include molecular binding species to selectively bind with surface receptors on the intended target tissue, perhaps changing one or more visual (chromatic) properties in the process and/or including a visual marking moiety. Some non-limiting examples of suitable molecular binding species are peptides and aptamers. Suitable peptides and aptamers may be selected for target tissue (e.g. nerve tissue, fat, etc.) and may be selected as known in the art.

Inclusion of molecular binding species that have been selected for the target cells may be advantageous to assist with anatomical visualization during a surgical procedure. The molecular binding species may be provided suspended in a delivery vehicle, such that it may be conveniently delivered to the target tissues during a procedure. The delivery vehicle may be a gel material, a 1 part curing gel, elastomer, etc. that may be conveniently delivered to the target tissues. A fully curable vehicle may be advantageous for providing a simplified method for completely removing the medium from the body after the surgical procedure and/or targeting process has been completed.

Molecular binding species may include a visual marking moiety that is configured to improve visibility thereof. Thus the molecular binding species may bind to the target tissue sites (e.g. nerve tissue, etc.), and may be highlighted by the visual marking moiety for visualization with an appropriate visualization system. Some non-limiting examples of visual marking moieties include: 5-carboxyfluorescein; fluorescein-5-isothiocyanate; 6-carboxyfluorescein; tetramethylrhodamine-6-isothiocyanate; 5-carboxytetramethylrhodamine; 5-carboxy rhodol derivatives; tetramethyl and tetraethyl rhodamine; diphenyldimethyl and diphenyldiethyl rhodamine; dinaphthyl rhodamine; rhodamine 101 sulfonyl chloride; Cy3, Cy3B, Cy3.5, Cy5, Cy5.5, Cy 7, indocyanine green, IR800CW or combinations thereof.

This visualization approach may be advantageous to identify the key tissues for surgical procedures (such as renal sympathectomy). By providing the material in a form suitable for surgical delivery and complete removal post operatively, the resulting system may be safer compared to approaches that require systemic application of the material.

In aspects, a system in accordance with the present disclosure may include an implantable tool, configured to be left in the body following the surgical procedure for purposes of follow up.

In aspects, the implantable tool may include a self-wrapping sheath in accordance with the present disclosure. The implantable tool and/or self-wrapping sheath may include one or more sensing tips to interface with the adjacent tissues. The implantable tool may include communication circuitry to communicate monitored signals or signals created therefrom to a monitor outside of the body. Such a system may be used to monitor nerve function (e.g. electrophysiological signals, nerve activity, EMG, local field potentials, etc.) to determine if the undesirable signal is returning or not after the surgical procedure.

In aspects, the implantable tool may include a draw cord, configured to mechanically connect the tool to the exterior of the body. Upon completion of the monitoring period, the draw cord may be used to withdraw the implantable tool from the body. Thus the implantable tool may provide follow up monitoring for days, weeks, to months after surgery, but may still be removed from the patient in an out-patient setting.

The system may be used to monitor the site after surgery, to determine if the functional changes will last indefinitely, for a short period of time, etc. May be useful for scheduling follow up, prognosticating on patient outcomes, etc.

The surgical system may include other functionality including: angiographic dye delivery, saline delivery, temperature monitoring, intra and extra vascular coordination between devices, through wall imaging, through wall current flow, saline provision for internal arterial cooling, optical coherence tomographic (OCT) capabilities, and the like.

FIGS. 1a-f show aspects of a surgical tool in accordance with the present disclosure. FIG. 1a shows a surgical tool including an arm 130 and a clamp 110a, 110b arranged around an anatomical site 1 (in this case a vessel). The clamp 110a, 110b includes one or more sensing tips in accordance with the present disclosure. The surgical tool may include a hinge 120, perhaps operable by an external operator to open and/or close 115 the clamp 110a, 110b about the target anatomy 1. In the non-limiting example shown, one or more of the sensing tips is an electrode for electrically interfacing with an adjacent tissue 2 of the target anatomy. The sensing tips, hinge, etc. may be interconnected 125 with a controller, connector, a microcircuit element in accordance with the present disclosure, or the like, via the arm 130 (i.e. equivalently a delivery catheter, endoscope, etc.).

FIG. 1b shows a face of a clamp 110a, 110b in accordance with the present disclosure. The clamp face 135 includes a plurality of electrodes 140, 145 for electrically interfacing with adjacent tissues. The electrodes 140, 145 (or equivalently sensing tips), may be arranged on one or more faces of the clamp 110a, 110b. One or more of the electrodes 140, a group of electrodes, etc. may be configured so as to monitor physiological parameters there-between, as a monopolar, bipolar, and/or multi-polar ablation electrode, combinations thereof, or the like. In the non-limiting example shown in FIG. 1b, the row(s) of small electrodes 140 may be configured to monitor electrophysiological signals (e.g. nerve activity, EMG, local field potentials, etc.) in the adjacent anatomy, while one or more electrodes 145 in the row of big electrodes may be configured to apply ablation current(s) therethrough (i.e. between another electrode on the clamp, a macroelectrode within the body, an electrode patch on the body, etc.).

FIG. 1c shows an aspect of a clamp 110a in accordance with the present disclosure that includes a plurality of embossed electrode elements 140, 145 each in accordance with the present disclosure. The clamp 110a also includes an electrode 155 facing away from the tissue interfacing face, configured in this case to monitor ambient fields, which may be used to construct a reference macroscopic signal, monitor for levels of electromagnetic interference, etc. The outer surface electrode 155 and/or at least a portion of the outer clamp surface 137 may be tied to a reference potential 165, so as to shield the microelectrodes 140, 145, provide a stable reference against which to measure local electrophysiological activity, etc. The electrodes 140, 145, 155, optionally 137 may be interconnected 125 with an external controller, interconnect, a microcircuit in accordance with the present disclosure or the like.

FIG. 1d shows a non-limiting example of a clamp in accordance with the present disclosure. The clamp includes a local control circuit 170 in accordance with the present disclosure, which may be configured to perform tasks such as pre-amplification, signal conditioning, RF signal routing, analog to digital conversion, signal buffering, communication with externally located hardware, multiplexing/demultiplexing functions, signal isolation, etc. The circuit 170 may be interconnected 125 with one or more of the hinge 120, the clamp 110a, 110b, sensing tips located thereupon, etc. The circuit 170 may be interconnected 175 with one or more controllers, interconnects, etc. located at a proximal tip of the arm 130 (i.e. equivalently a delivery catheter, a guidewire, an endoscope, etc.).

In the example shown in FIG. 1d, the local control circuit 170 is shown attached to the control arm 130 of the surgical tool, but may be placed anywhere on the tool, on the clamp members 110a, 110b, clamp faces 135, etc.

FIG. 1e shows aspects of a surgical tool in accordance with the present disclosure interfacing with a vessel 1 (e.g. an artery, a renal artery, etc.). Some aspects of the included electrodes A-E are highlighted so as to demonstrate an aspect of how the device may function during ablation of a target tissue 3 (e.g. here shown as a target nerve). The electrodes to consider in this regard are labeled as sensory electrodes A-D, and ablation electrode pair E (i.e. a biopolar electrode aspect). The configuration shown in FIG. 1e is just to highlight some of the functionality of the system in practice. Each of the electrodes A-E are provided in communication with an external controller, interconnect, a microcircuit, or the like provided by one or more interconnects 125 arranged within the surgical tool.

FIG. 1f shows a time graph of signals to demonstrate a non-limiting example of how the clamp shown in FIG. 1e may be used in practice. To the left of the graph, one can see electrograms taken from electrodes A-D with respect to a reference electrode (e.g. a macroelectrode, a reference on the clamp, etc.). Before the ablation signal is applied, one can see significant activity in the vicinity of electrodes A and B, indicating the presence of the target nerve nearby. The signals monitored at electrodes A and B may be indicative of an overactive nerve (i.e. if nerve activity exceeds a known threshold value, etc.) and thus may be considered directly to determine if the nerve is the right target for a surgical procedure. Additionally, alternatively, or in combination, the relationship between signals A and B may be used to determine the direction of signal traffic along the target nerve, perhaps to determine if it is the right target for a surgical procedure.

After application of an ablation current to the ablation electrode pair E, a change in the signals as monitored by electrode A and B can be seen. In the example shown, the nerve activity at electrode B has decreased significantly indicating that the denervation procedure affected the target nerve and has successfully completed the denervation of the nerve.

Figure 2B:
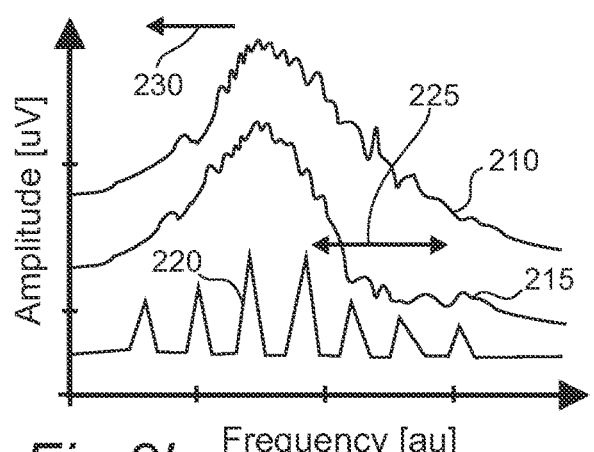

FIGS. 2a-b show aspects of non-limiting examples of stimulation and monitored procedures of electrophysiological signals in accordance with the present disclosure. FIG. 2a shows the signal B obtained at a monitoring location within the body during a procedure. The signal shows the stimulus pulse 201 followed by the evoked response 205 from the nerve in question. Evident from the figure is the latency, amplitude, and character of the evoked response 205. One or more of these aspects may be used to determine the effectiveness or state of completion of a surgical procedure applied to the nerve under study.

FIG. 2b shows aspects of a non-limiting example of monitoring an evoked nervous response at a monitoring location in response to a stimulus applied at a stimulating location within the body. The stimulus 220 is shown as a sequentially applied train of pulses and the monitored evoked response is shown before 210 and after a partial completion 215 of a surgical procedure (given the same stimulus pulse train). As shown, a change in the frequency characteristics can be seen in the signal response after the procedure has been at least partially completed. Demonstrated examples of changes include a shift in the frequency response 230 of the evoked potential spectrum, and changes over a region 225 of the spectrum indicative of changing functionality of the associated anatomical features (i.e. the nerves under study). Such changes may be used to determine if the surgical procedure is being applied to the proper target tissues, if the procedure is effectively completed or if further procedure is necessary.

Additionally, alternatively, or in combination, the stimulus may result from a sequence of input pulses, perhaps caused by an associated ablation procedure (e.g. as caused by an RF ablation procedure, etc.). Thus the act of stimulation may be provided by the ablation procedure itself.

Figure 3A:
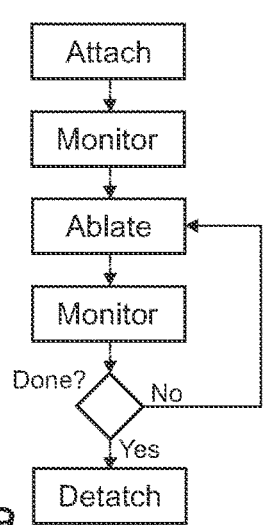
FIGS. 3a-b show aspects of methods for monitoring locations in a body before, during and/or after a surgical procedure.
Figure 3B:
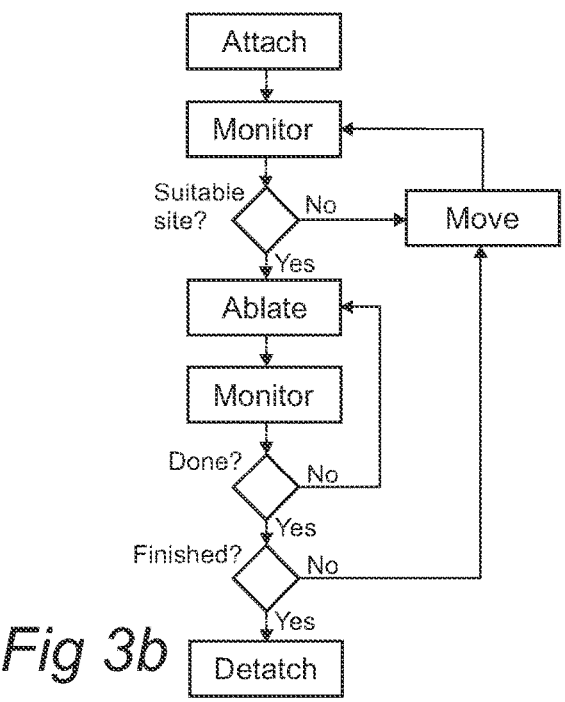

FIGS. 3a-b show aspects of methods for monitoring locations in a body before, during and/or after a surgical procedure in accordance with the present disclosure.

FIG. 3a shows aspects of a method in accordance with the present disclosure including contacting (i.e. attaching, latching onto, clamping around, etc.) at least one surgical tool (e.g. a sensing tip, a microfinger, a clamp, a self-wrapping structure, a microcatheter, a microfinger array, etc.) to a tissue site of interest (e.g. onto an organ, around a vessel, around a renal artery, into a region of neurologically significant tissues, etc.), monitoring a physiological signal at a first monitoring location (e.g. on the wall of the vessel), performing at least part of a surgical procedure (e.g. ablation, chemical delivery, etc.), and monitoring at a location (i.e. the first location, an alternative location, etc.) to determine if the surgical procedure was successful. The method includes making a decision to continue with the surgical procedure if the monitoring response shows that it is not complete, and detaching (i.e. so as to remove the tool from the anatomical site, move to another target location, etc.) the tool from the surgical site. Further aspects of such methods are discussed in the present disclosure.

FIG. 3b shows aspects of a method for detecting a surgical location and performing a surgical procedure thereupon in accordance with the present disclosure. The method includes contacting (i.e. attaching, latching onto, clamping around, etc.) at least one surgical tool (e.g. a sensing tip, a microfinger, a clamp, a self-wrapping structure, a microcatheter, a microfinger array, etc.) to a tissue site of interest (e.g. onto an organ, around a vessel, around a renal artery, into a region of neurologically significant tissues, etc.), monitoring a physiological signal at a first monitoring location (e.g. on the wall of the vessel) to determine if the target tissues (e.g. a nerve, a tumor site, etc.) have been located. If the target tissues are present, performing at least part of a surgical procedure (e.g. ablation, chemical delivery, etc.), and monitoring at a location (i.e. the first location, an alternative location, etc.) to determine if the surgical procedure was successful. The method includes making a decision to continue with the surgical procedure if the monitoring response shows that it is not complete and making another decision if it is completed. The method includes making a decision as to if the overall surgery is completed. If it is not complete the method includes moving (i.e. so as to remove the tool from the anatomical site, move to another target location, etc.) the tool to another target surgical site, and/or selecting another set of electrodes to test for the presence of a target tissue. If the overall procedure is complete, the method includes detaching the tool from the surgical site. Further aspects of such methods are discussed throughout the present disclosure.

Figure 4A:
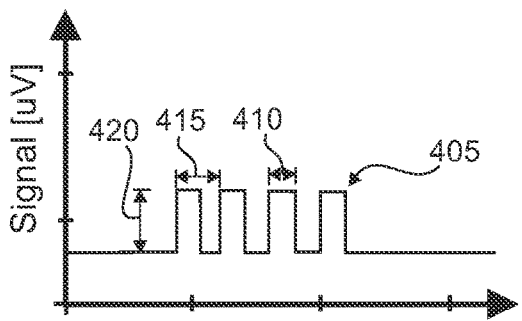
FIGS. 4a-b show signals associated with a method for monitoring electrophysiological activity at one or more locations on a body in accordance with the present disclosure.
Figure 4B:
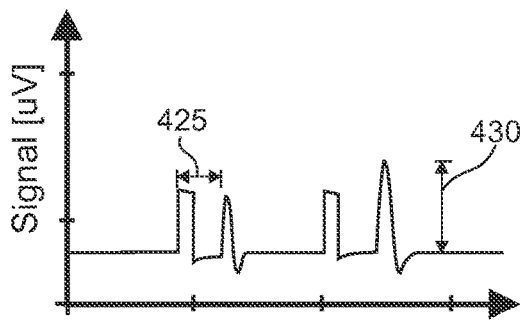

FIGS. 4a-b show aspects of signals associated with a method for monitoring electrophysiological activity at one or more locations on a body in accordance with the present disclosure. FIG. 4a shows an exemplar pulse train 405, highlighting various aspects that may be adjusted during a surgical intervention so as to better elucidate the physiological signals from a monitoring location. A non-limiting example of the pulse train characteristics that may be varied to highlight characteristics of the evoked response includes the amplitude 420, pulse spacing 415, pulse width 410, the number of pulses, etc. Other aspects of suitable stimulation signals are discussed throughout the present disclosure.

FIG. 4b shows an electrophysiological response measured at a monitoring location in accordance with the present disclosure. The time characteristics of the evoked response demonstrates aspects of the sensed signal such as latency 425, amplitude 430, and character (frequency content, signal shape, etc.) that may change as surgical procedure is performed on the target tissues. Other aspects of the evoked signal responses are discussed throughout the present disclosure.

Figure 5A:
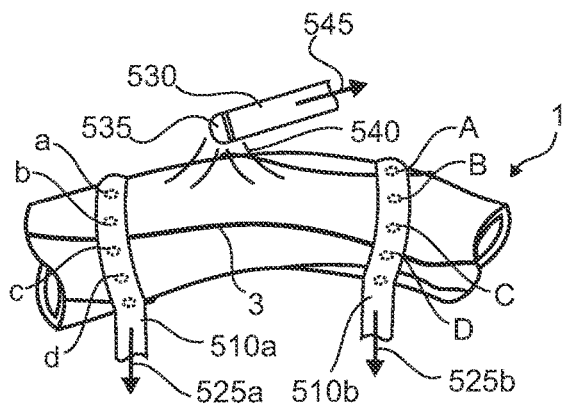
FIGS. 5a-b show aspects of a multi-tool surgical system for performing a surgical procedure in accordance with the present disclosure.
Figure 5B:
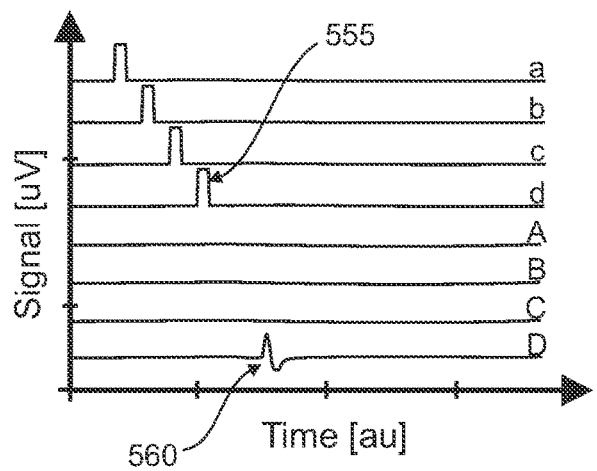

FIGS. 5a-b show aspects of a multi-tool surgical system for performing a surgical procedure in accordance with the present disclosure. The system includes a plurality of self-wrapping tools 510a, 510b (in this case, two self-wrapping tools), arranged around the circumference of a target anatomical structure 1 (in this case, a renal artery), and a surgical tool for applying a surgical procedure 530 (in this case an ablation procedure) at one or more surgical locations along the vessel 1. Each self-wrapping tool 510a, 510b includes a plurality of electrodes a-d, A-D for interfacing with the adjacent tissue (here labeled electrodes a-d and electrodes A-D). A target nerve is shown on the renal artery 3 for purposes of discussion. Each of the self-wrapping tools 510a, 510b includes interconnects 525a, 525b for interconnecting one or more of the electrodes a-d, A-D with a controller, a microcircuit, etc. in accordance with the present disclosure.

The surgical tool 530 is shown including an electrode tip 535 for applying energy 540 to the vessel 1 during a procedure. The surgical tool 530 includes interconnects 545 for interfacing with a controller, an interconnect or the like for providing energy 540 to the vessel 1 during the procedure.

FIG. 5b shows a temporal graph of a series of stimuli 555 (applied at electrodes a-d) and responses (measured at electrodes A-D) signals which may be used to determine the location of the target nerve, determine the extent of a surgical procedure, etc. As shown in the figure, stimuli are applied, optionally sequentially at electrodes a-d and responses are monitored at electrodes A-D. As seen in the figure, a response 560 on electrode D to a stimulus provided to electrode d may be used to positively identify the location of the target nerve. In the example shown, an ablation catheter may be directed to the location of the target nerve and activated to perform the surgical procedure. Additionally, alternatively, or in combination, the self-wrapping tools may include hardware for applying an ablation signal locally to the identified target nerve as part of the surgical procedure.

Figure 6A:
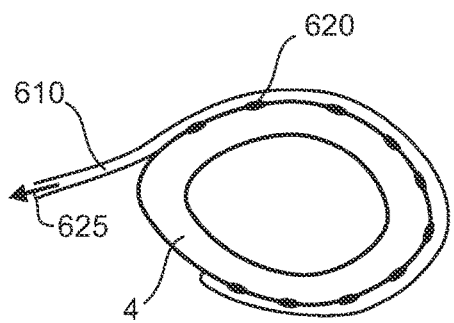
FIGS. 6a-c show aspects of a hook like surgical tool and examples of use thereof in accordance with the present disclosure.
Figure 6B:
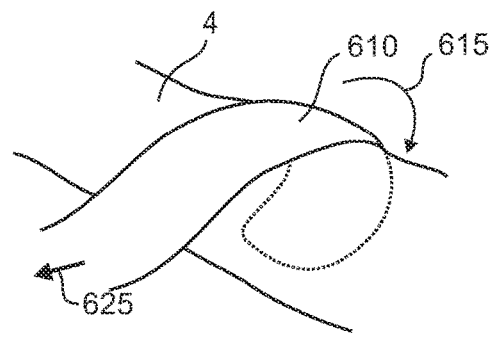
Figure 6C:
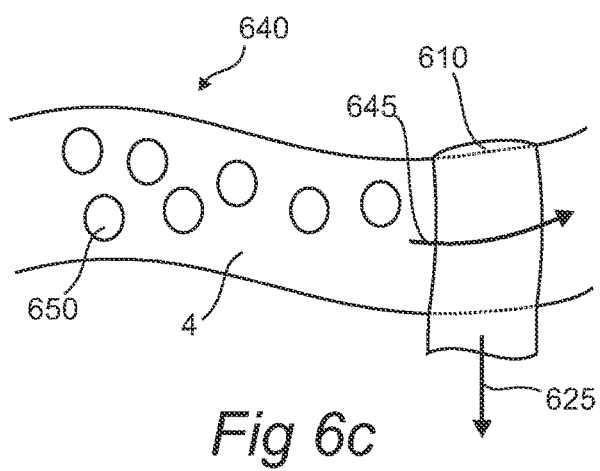

FIGS. 6a-c show aspects of a hook-like surgical tool 610 and some non-limiting examples of use thereof in accordance with the present disclosure. FIG. 6a shows a hook-like surgical tool 610 including one or more sensing tips 620 to interface with an inner surface thereof (i.e. the surface facing towards the center of curvature of the hook-like tool). Additionally, alternatively, or in combination the hook-like surgical tool 610 may include one or more sensing tips 620 arranged upon the outer surface thereof. The hook-like tool 610 is shown coupled to a vessel 4 (post capture thereof). The sensing tips 620 are shown at the interface between the hook-like tool 610 and the captured vessel 4. The hook-like tool 610 may be advantageous for carefully capturing a tubular anatomical structure (e.g. a vessel, an artery, a renal artery, a nerve bundle, etc.) for performing a surgical procedure thereupon without collapsing the structure or applying excessive pressure thereto. After capture, the sensing tips 620 may be configured to monitor, stimulate, and/or selectively ablate the underlying tissues as desired by the surgical process. In the non-limiting example shown, the sensing tip electrodes 620 are embossed so as to further bias them towards the vessel tissues. The hook-like tool 610 may include interconnects 625 to couple one or more of the sensing tips 620 with a controller, a microcircuit, an interconnect, etc. each in accordance with the present disclosure.

FIG. 6b shows another view of the hook-like tool 610 after capture of a vessel 4. The hook-like tool 610 provides a means for contacting the vessel tissues over much of the circumference thereof. The hook-like tool may include a capture mechanism so as to easily wrap around 615 the vessel 4 prior to performing a surgical procedure, and/or a release mechanism so as to easily detach/release the vessel 4 after the intended surgical procedure is completed. Aspects of the hook-like tool 610 may be interconnected 625 with a controller, a microcircuit, and/or interconnect each in accordance with the present disclosure.

FIG. 6c shows use of a hook-like tool 610 in accordance with the present disclosure to selectively ablate target nerves along the surface of a renal artery 4. The hook-like tool 610 may initially be placed upon the artery 4 at a distal or proximal end, depending on the type of signal that is to be corrected for (efferent, afferent). Then the sensing tips (in this case electrodes) in the hook-like tool 610 may be used to assess the electrophysiological activity around the circumference of the artery at the placed location, and selectively ablate tissues around the circumference dependent upon the monitored activity (as well as monitoring the extent of the ablation process). The hook-like tool 610 may be swept 645 along the artery 4, selectively repeating any monitoring and/or ablation process so as to successfully complete the intended surgical procedure and/or form a region 640 of ablation sites 650 as part of the surgical procedure. The hook-like tool 610 may be removed from the tissues after completion of the surgical procedure.

Figure 7A:
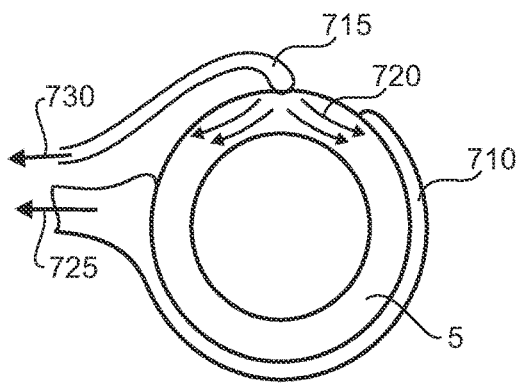
FIGS. 7a-c show aspects of a pressure point based surgical tool and method for monitoring neural activity in an associated anatomical structure in accordance with the present disclosure.
Figure 7B:
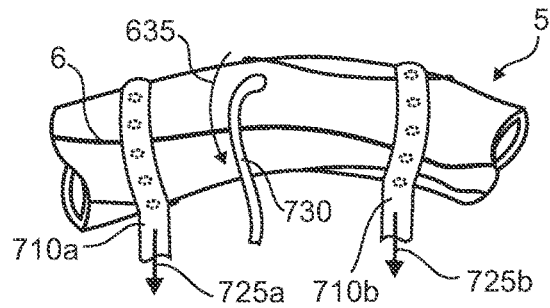
Figure 7C:
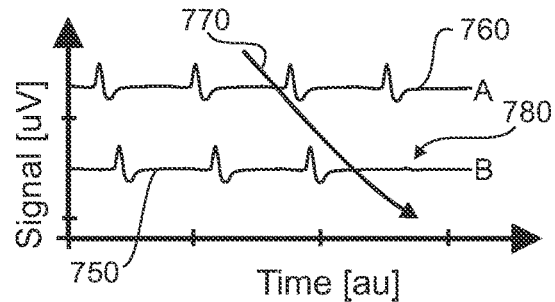

FIGS. 7*a-c* show aspects of a point pressure based surgical tool and method for monitoring neural activity in an associated anatomical structure in accordance with the present disclosure. FIG. 7*a* shows an example of a surgical tool with a holding face 710 (e.g. similar to a hook-like tool, a pressure tool, etc.) and an adjustable point pressure based ablation microfinger 715 (i.e. for sensing, applying pressure, and/or ablating underlying tissues). The point pressure based microfinger 715 may be swept over the surface of the tissue as one or more aspects monitor related physiological activity elsewhere along the artery 5 or in the body. The point pressure based finger 715, may be configured to apply an ablation current 720 to the tissues, possibly using at least a portion of the holding face 710 as a counter electrode for the RF ablation current. The holing face 710 and the point pressure based finger 715 may be interconnected 725, 730 with a controller, a microcircuit, an interconnect, or the like, each in accordance with the present disclosure.

FIG. 7*b* shows an example of a surgical system in accordance with the present disclosure, including two monitoring tools 710*a*, 710*b* arranged proximally and distally to a surgical site on a vessel 5. A point pressure based finger 730 is applied to the surgical site and may scan 635 the surgical site in order to find and selectively ablate tissues thereupon (i.e. so as to perform a surgical procedure on a target tissue 6 in accordance with the present disclosure). In aspects, the monitoring tools 710*a*, 710*b* may include interconnects 725*a*, 725*b* arranged so as to interconnect one or more sensing tips included therein with a controller, a microcircuit, and/or an interconnect each in accordance with the present disclosure.

FIG. 7*c* shows aspects of an example of a method for finding a suitable target tissue (e.g. a target nerve) in accordance with the present disclosure. The method includes monitoring electrophysiological activity 750, 760 at electrode locations (i.e. sensory tip locations) on tools A and B, sweeping 770 a point pressure probe along the circumference of the vessel and stopping when a significant change 780 in the electrophysiological activity amongst electrodes on tool A and/or B is detected. Thus determining when the point pressure probe is applying compressive forces to a neural structure located between sensing tips on tool A and tool B. The method may include applying a surgical procedure to the neural structure after identifying the presence thereof, etc.

Figure 8A:
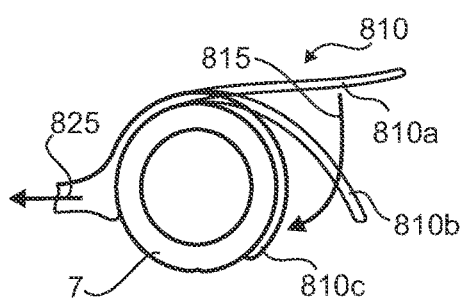
FIGS. 8a-b show aspects of a self-wrapping surgical tool in accordance with the present disclosure.
Figure 8B:
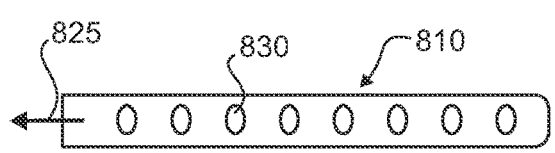
Figure 8B:
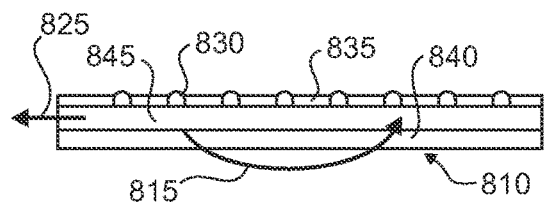

FIGS. 8*a-b* show a self-wrapping surgical tool 810 in accordance with the present disclosure. FIG. 8*a* shows a self-wrapping surgical tool at various stages of actuation, stage A 810*a* (initial shape), stage B 810*b* (intermediate shape), and stage C 810*c* (captured shape) while in the process of capturing 815 a vessel 7. The actuation process may be performed in accordance with the present disclosure. In aspects, the actuation may be performed by an included electroactive material within the self-wrapping tool 810. The self-wrapping tool 810 may be used to actively bias one or more included sensing tips towards the tissues of the underlying anatomy (in this case a vessel 7). The actuator materials, sensing tips, etc. included within the self-wrapping tool 810 may be interconnected 825 with a controller, a microcircuit, and/or an interconnect each in accordance with the present disclosure for purposes of performing a surgical procedure as described herein.

FIG. 8*b* shows some aspects of a self-wrapping tool 810 in accordance with the present disclosure. A row of electrodes 830 is shown along a face of the tool 810, configured so as to interface with an adjacent tissue after it has been successfully captured by the tool 810. The figure also shows a cross section of a self-wrapping tool 810 with a laminar structure, demonstrating how such a tool may be built-up in practice. The structure includes one or more actuator layers 840, 845 (optionally including one or more electrode elements). The actuator layers 840, 845 may include an active material in accordance with the present disclosure, a thermoresponsive material, a capillary actuating material, etc. The structure also include a patterned layer with inter dispersed electrode elements 830 (or more generally speaking sensory tips) and isolated regions 835 (e.g. insulating regions) so as to collectively interface with the adjacent tissues. The actuating layers 840, 845 may be configured to change shape upon command, so as to change the overall shape 815 of the tool 810 and capture/release a target anatomical structure within a body.

Figure 9A:
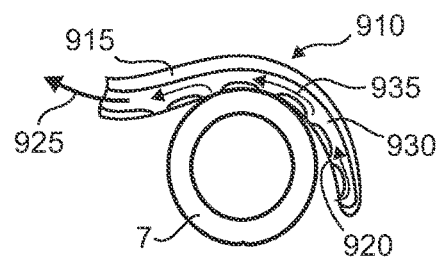
FIGS. 9a-b show aspects of a soft gripping surgical tool in accordance with the present disclosure.
Figure 9B:
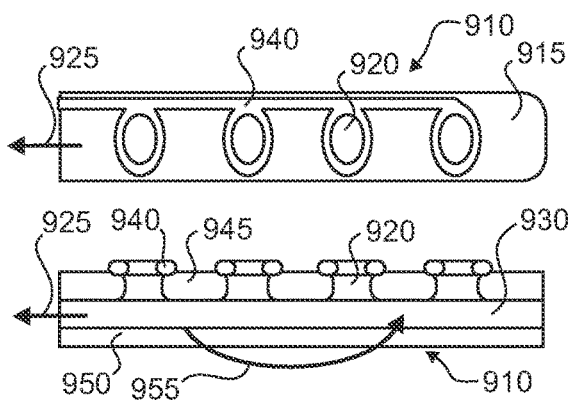

FIGS. 9*a-b* show aspects of a soft gripping surgical tool 910 in accordance with the present disclosure. FIG. 9*a* shows a soft gripping surgical tool 910 including microchannels 930 to connect 925 one or more ports 920 on the tip of the surgical tool, with a suction source (i.e a vacuum source outside of the body, at the far end of the surgical tool, etc.). Fluid may be drawn 935 through the microchannels 930 in order to interface the surgical tool 910 with a local anatomical site 7. The soft surgical tool 910 may include one or more ports 920 situated along with the microchannels 930. The soft surgical tool may include a soft backing material 915 (e.g. an elastomer, a polymer, etc.) and a central member (e.g. film, filament, etc.) in order to control and/or limit distension of the soft-gripping tool 910 during an actuation process. The surgical tool 910 may include one or more sensing tips each in accordance with the present disclosure, optionally included near to one or more of the ports 920, or along the port face, so as to interface with the target anatomy 7 during a procedure.

FIG. 9*b* shows aspects of the soft gripping surgical tool 910 including an array of electrode 940 based sensing tips (4 electrodes shown in FIG. 9*b*). The electrodes 940 may be electrically connected 925 to circuitry elsewhere upon the surgical tool 910, to a local control circuit, an interconnect, or the like, each in accordance with the present disclosure. In aspects, the electrodes 940 may be electrically routed via a flexible circuit included in the central member 945, via microwires, via a cable assembly, etc. In the cross section shown, each of the electrodes 940 includes a centralized port 920 located therein, the ports 920 are connected to the micro-channels 930, which then run along the length of the tool 910 back to a vacuum source 925 (not explicitly shown). The micro-channels 930 may be placed off the neutral axis of the tool 910, such that a vacuum applied thereto may assist in bending 955 the tool 910 towards the target tissue locations. The tool 910 may include a soft backing material 950 (e.g. an elastomer, a polymer, etc.) and a central member (e.g. film, filament, etc. not explicitly shown) in order to control and/or limit distension of the soft-gripping tool 910 during an actuation process 955.

Figure 10:
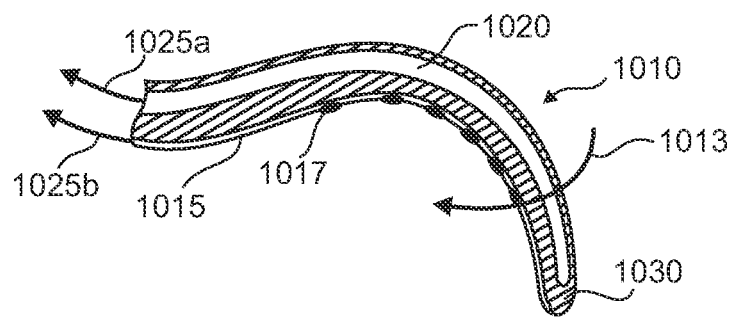
FIG. 10 shows aspects of a soft gripping tool for use in a surgical tool in accordance with the present disclosure.

FIG. 10 shows aspects of a soft gripping tool 1010 for use in a surgical tool in accordance with the present disclosure. The soft gripping tool 1010 includes one or more microchannels 1020 asymmetrically situated off of the neutral axis of the tool 1010 such that application of pressure, vacuum, or changes in the fluid level therein (i.e. via fluid exchange 1025a with a fluid source, vacuum pump, etc.) may be used to bend 1013 the tool towards or away from a surgical site. The tool 1010 may include a substrate 1015, the substrate 1015 including one or more sensing tips 1017, each in accordance with the present disclosure for interfacing with an adjacent target tissue during a procedure. The sensing tips 1017 may be coupled 1025b with a controller, a microcircuit, an interconnect, or the like each in accordance with the present disclosure to perform one or more measurements, stimulations, and/or ablation procedures during the course of a procedure.

Figure 11:
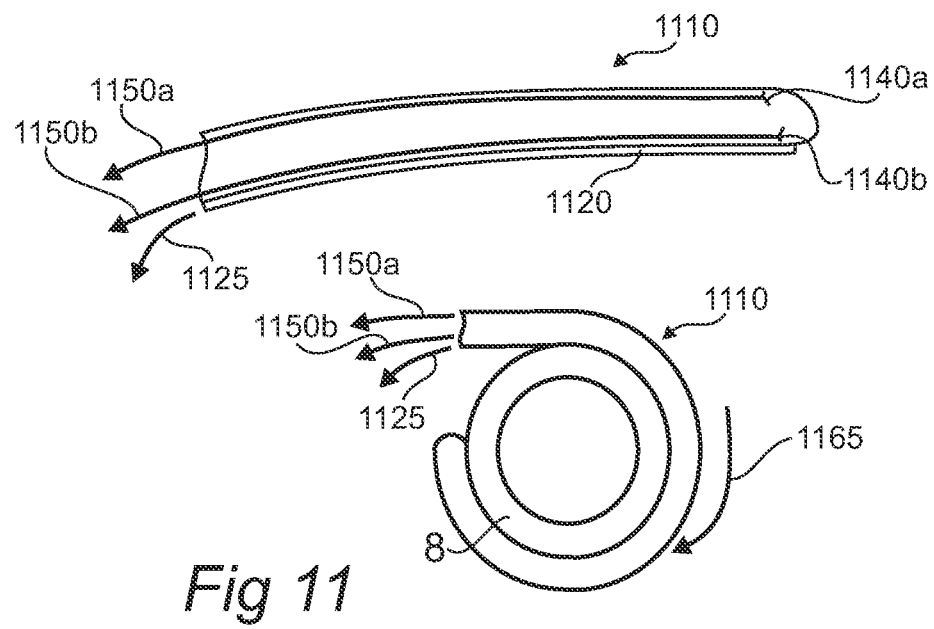
FIG. 11 show aspects of a tendon driven soft gripping surgical tool in accordance with the present disclosure.

FIG. 11 shows a tendon driven soft gripping surgical tool 1110 in accordance with the present disclosure. The soft gripping surgical tool 1110 may be constructed from one or more soft materials (e.g. elastomers, polymers, etc.) and may include one or more tendons 1140a, 1140b, oriented off of the neutral axis of the tool 1110, such that extension and/or retraction of the tendons 1140a, 1140b may be used to bend 1165 the tool 1110 so as to interface with an adjacent tissue structure 8. The soft gripping surgical tool 1110 may include one or more sensing tips arranged upon one or more faces 1120 thereof. The sensing tips may be configured so as to interface with an adjacent tissue 8 upon capture. FIG. 11 shows the tool in a generally extended state as well as coiled around a vessel 8 (so as to interface with the tissues thereupon). The sensing tips (i.e. as included along a surface 1120 of the tool 1110) may be interconnected 1125 with a controller, a microcircuit, an interconnect, or the like each in accordance with the present disclosure. The tendons 1140a, 1140b may be interconnected 1150a, 1150b with tendon drive elements, a mechanism, etc. for providing a pulling force to one or more of the tendons 1140a, 1140b during a procedure.

Figure 12:
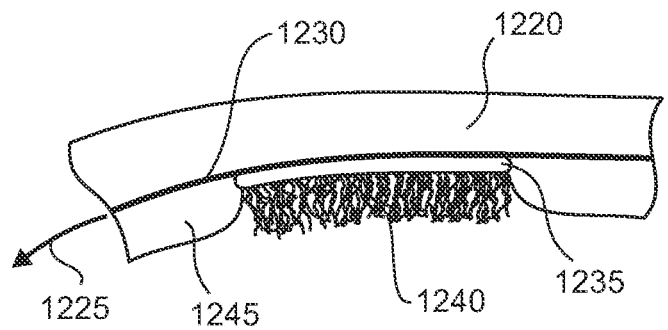
FIG. 12 shows aspects of a whisker electrode configuration in accordance with the present disclosure.

FIG. 12 shows aspects of a non-limiting example of a whisker configuration in accordance with the present disclosure. The tool may include one or more whisker-like structures 1240 extending from an electrode element 1235 included in the tool (i.e. collectively forming a sensing tip in accordance with the present disclosure). The electrode element 1235 may be electrically interconnected 1225 with a circuit element elsewhere in the tool, perhaps a local control circuit, etc. Such electrical interconnects 1230 may be provided by a flexible circuit, wiring, cabling, etc. The tool may include a backing layer 1220 configured such that one or more of the electrical interconnects 1230 may be situated substantially at the neutral axis of the tool (i.e. so as to minimize stress thereupon during bending of the tool). The tool may include insulating regions 1245 configured for similar purposes, and/or as ways to define the extent of the electrode element 1235 on the tool surface.

In aspects, one or more of the whiskers 1240 may be formed from microfibers, nanofibers, microneedles, nanoneedles, etc. In aspects, one or more whiskers 1240 may be formed from a carbon structure, e.g. a carbon fiber, a carbon nanotube, etc. In aspects, the whiskers 1240 may be insulated along a portion of their length, with an electrically exposed region at the tip thereupon.

The whiskers 1240 may be configured with sufficient strength so as to penetrate into a tissue structure when biased there against. The whiskers 1240 may be configured such that the tips may penetrate into an adjacent nerve structure, a nerve bundle, a nerve cell body (often called the soma), a dendrite, an axon, a cable-like bundle of neural axons, the endoneurium, a fascicle, an epineurium, and/or a perineurium during a procedure. Such a configuration may be advantageous for monitoring a neuronal signal from a more highly selective tissue site, than would be achievable with an associated macroscopic electrode.

Figure 13:
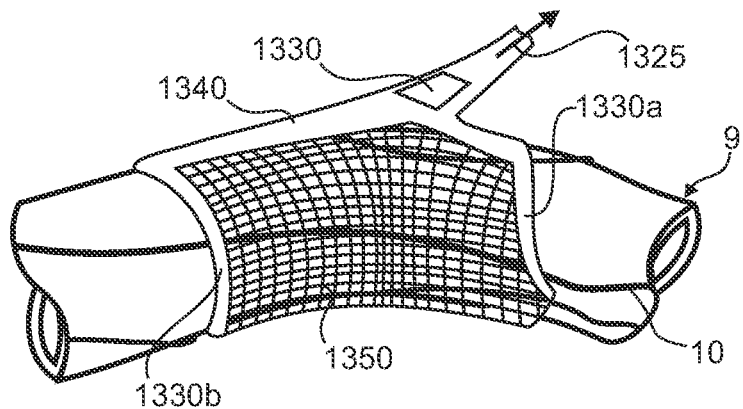
FIG. 13 shows aspects of a net-like surgical tool deployed at a surgical site in accordance with the present disclosure.

FIG. 13 shows net-like surgical tool deployed at a surgical site in accordance with the present disclosure. The net-like surgical tool may include a plurality of sensing tips arranged upon a soft, flexible substrate 1350 (e.g. a net, a fibrous substrate, a porous substrate, a stretchable electronic substrate, etc.). The netting may include one or more actuating elements 1330a, 1330b (e.g. active material elements, capillary force elements, etc.) so as to actively wrap the net 1350 around an adjacent tissue structure 9. The net-like surgical tool may include a local control circuit 1330 in accordance with the present disclosure to communicate 1325 between one or more of the sensing tips and a controller, an interconnect, etc. The netting 1350, actuating elements 1330a, 1330b, control circuit 1330, etc. may be coupled with a substrate 1340 configured so as to lend support to the other elements of the tool, physically interconnect the elements with a proximal connector, etc.

In aspects, the net-like structure 1350 may include one or more interwoven wires, with associated sensing tips. The sensing tips may be arranged such that they contact the local tissues 9 when the net is biased against the tissue 9. In one non-limiting example, the net-like array 1350 may be formed from an interwoven group of superelastic wires (e.g. nitinol wires, spring steel wires, etc.). The net 1350 may be formed as a sock, webbing, an arched structure, a donut, etc. Upon deployment to the surgical site 9, the net 1350 may contract and/or wrap around the anatomical site so as to contact the local tissues of interest (i.e. via capillary effect, via actuation of one or more of the actuating elements 1330a, 1330b, etc.). Electrical interconnects for the sensing tips may be provided via the wires, routed along the wires, etc. In aspects, substrates in accordance with the present disclosure may be interwoven instead of the wires as shown. Such substrates may be used to form a deployable mesh-like structure complete with electrical interconnects, sensing tips, distributed integrated circuits, etc.

The net like structure 1350 may be formed from one or more fibers, wires, ribbons, etc. Additionally, alternatively, or in combination the one or more net-like structures 1350 may be included on a substrate in accordance with the present disclosure (e.g. a porous substrate material such as a silk structure). In aspects, a silk-flex circuit composite may form the net like structure 1350. In this example, the flex circuit may be formed from materials as known to those skilled in the art, the flex circuit may be constructed such that all space, not occupied by electrical interconnects are removed (thus forming a loosely connected webbing of flex circuit elements). The flex circuit may thus be formed in an excessively thin form (e.g. less than 10 um, less than 4 um, less than 1 um thick). A supporting material such as silk may be used to complete the substrate and form a functional, robust net like micro surgical tool.

In aspects, the sensing tips, as arranged over the net 1350 may be selectively used to monitor, stimulate, and/or ablate a target anatomy 10 (i.e. a nerve plexus, etc.) structure near the anatomy of interest 9.

Figure 14:
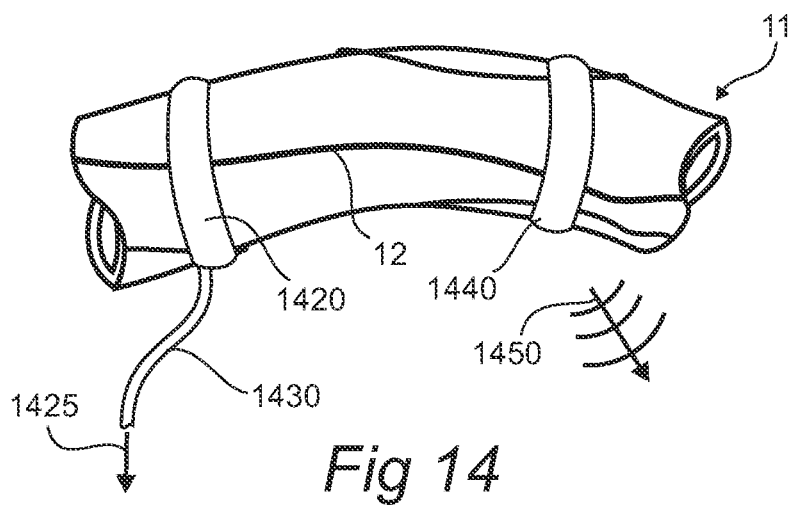
FIG. 14 shows aspects of implantable surgical tools deployed at a surgical site in accordance with the present disclosure.

FIG. 14 shows aspects of implantable surgical tools 1420, 1440 deployed at a surgical site in accordance with the present disclosure. The implantable surgical tools 1420, 1440 may include an interfacing portion (e.g. a clip, a hook-like structure, and/or a self-wrapping structure, any in accordance with the present disclosure). The tools 1420, 1440 may be placed against, around or upon a target anatomical structure during a procedure (e.g. placed around a renal artery 11), so as to interface with the tissues thereupon for purposes of monitoring, stimulating, and/or ablating. FIG. 14 shows two non-limiting examples of implantable surgical tools 1420, 1440 arranged around a renal artery 11. The first implantable surgical tool 1420 includes one or more sensing tips in accordance with the present disclosure and a tether 1430. The tether 1430 may include a cord to mechanically connect 1425 the interfacing portion of the tool 1420 to a location on the body (such as an entry port, etc.). The tether 1430 may include means for electrically communicating between an externally placed device and the interfacing portion of the tool 1420 and/or sensing tips include therein. The tether 1430 may include a lubricous coating to substantially limit bonding between the tether 1430 and adjacent tissues during the placement period. The interfacing portion of the tool 1420 may be equipped to monitor one or more physiological parameters of the adjacent anatomical structure for a prolonged period following placement. A plurality of sensing tips within the interfacing portion of the tool 1420 may be arranged so as to more precisely monitor activity of target anatomy 12, which may be arranged heterogeneously about the target anatomical site 11.

The second implantable surgical tool 1440 shown in FIG. 14 includes means for wirelessly communicating 1450 with an extracorporeal reader, so as to remotely monitor the surgical site 11 for prolonged periods of time without the need for physical access to the site during the monitoring period. Such an implantable tool 1440 may include a plurality of sensing tips, a microcircuit, etc. each in accordance with the present disclosure. The implantable tool 1440 may further include a power source, or means for harvesting energy from a provided signal (i.e. an RF signal), local kinetic motion, undulation of the underlying anatomical structure 11, or the like. Further aspects of implantable surgical tools 1420, 1440 are discussed elsewhere in the present disclosure.

Figures 15A, 15B:
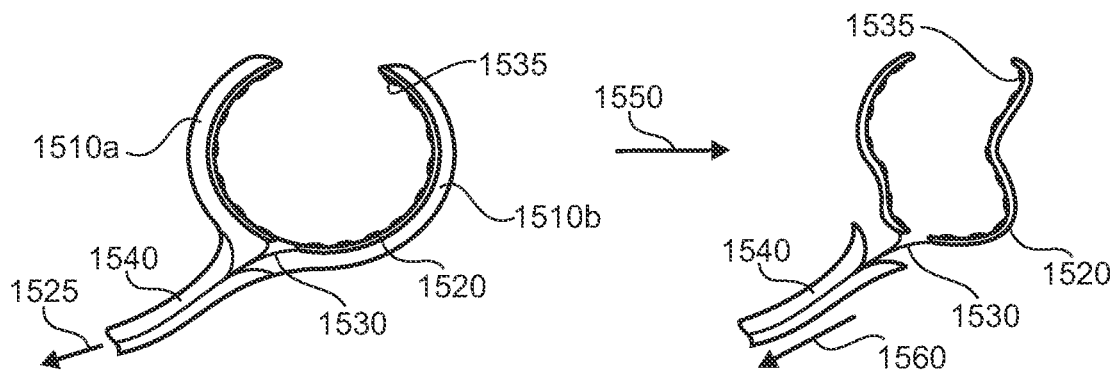
FIGS. 15a-b show aspects of an implantable and partially biodegradable surgical tool in accordance with the present disclosure.

FIGS. 15a-b show aspects of an implantable and at least partially biodegradable surgical tool in accordance with the present disclosure. FIG. 15a shows an implantable surgical tool in accordance with the present disclosure including a clip 1510a, 1510b, 1520 arranged with one or more sensing tips 1535. The implantable surgical tool also includes a biodegradable material (i.e. in this case shown the regions of the clip 1510a, 1510b), configured so as to degrade over a period of time after placement thereof within the body. An optional tether 1540 is attached to the clip 1510a, 1510b, 1520 via a substrate 1530, 1520, the substrate configured to interconnect 1525 one or more of the sensing tips 1535 with a controller, microcircuit, etc. The tether 1540 may be configured to access an extracorporeal reader, an extracorporeal port, a body port, etc. The tether 1540 may be configured for easy removal of the implantable tool after the monitoring period is completed (i.e. via providing a lubricious surface resistant to bioadhesion thereto).

FIG. 15b shows aspects of a non-limiting example of the implantable surgical tool after the degradable portion 1510a, 1510b has disintegrated 1550. In one non-limiting example, the non-degradable portion 1510a, 1510b is configured so as not to bond with adjacent tissues. Such a configuration may be advantageous for easy removal 1560 of the implantable tool after a monitoring period. Such a configuration may be advantageous for maintaining contact between a target tissue and the sensing tips 1535 immediately after placement, while providing a softening of the structure over time, so as to limit movement, between the sensing tips 1535 and adjacent tissues over time.

Figure 16:
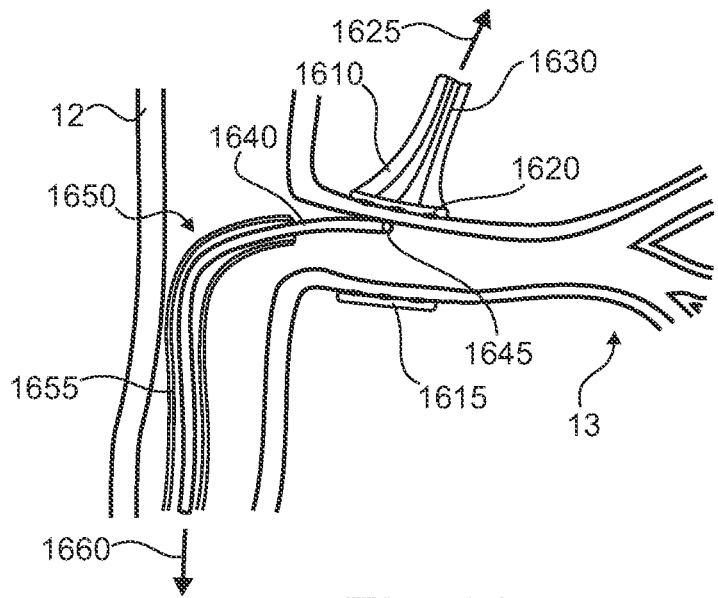
FIG. 16 shows coordinated operation of intra vascular and extra vascular tools for performing a surgical procedure on a renal artery in accordance with the present disclosure.

FIG. 16 shows coordinated operation of intra vascular 1650 and extra vascular tools 1610 for performing a surgical procedure on a renal artery 13 in accordance with the present disclosure. A catheter tool 1640 is shown inserted into a renal artery 13, the tip 1645 of the tool 1640 is arranged so as to bias against a wall of the artery 13 during a procedure. As shown, the catheter tool 1640 has an electrode tip 1645 (e.g. for sensing, stimulation, and/or ablation, etc.). An externally placed tool 1610 is also shown. In this case, an endoscopic surgical system including a clamp tool 1610 is shown engaged with the exterior of the vessel wall 13. The clamp tool 1610 includes a plurality of sensing tips 1620 (in this case shown as electrodes) which may be used to sense, stimulate, and/or ablate the local tissues. One or more of the sensing tips may be covered by an insulating layer 1615 to isolate them from the surrounding tissues during the procedure. The externally placed surgical system includes a control arm 1630, configured to mechanically and/or electrically interface 1625 the clamp tool 1610 with an external control system, a robotic control system, a microcircuit, an interconnect, and/or an operator.

The coordinated action of both the endoscopic surgical system and the catheter tool 1640 may be used to collectively identify and ablate tissues in the vessel wall 12.

As shown in FIG. 16, the catheter tool 1640 is delivered to the renal artery 13 via a delivery catheter 1655 and is interconnected 1660 with a proximal interconnect, controller, microcircuit, operator, or the like for performing the intended surgical task. The catheter tool 1640 is shown with a single electrode tip 1645 but may be equipped with a series of electrodes, may accommodate a guide wire for placement, etc.

Figure 17:
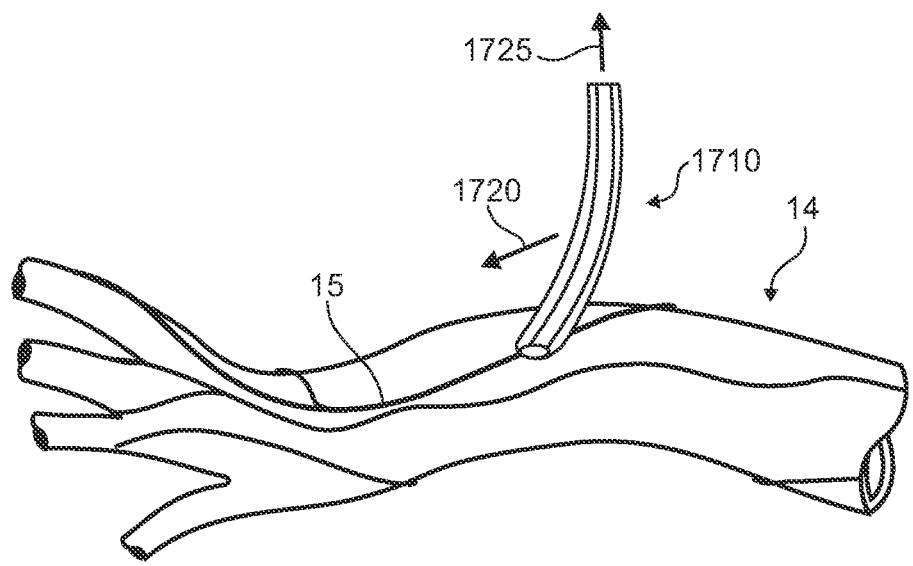
FIG. 17 shows aspects of a system for tracking a nerve structure in accordance with the present disclosure.

FIG. 17 shows a system for tracking a nerve structure in accordance with the present disclosure. A surgical tool 1710 in accordance with the present disclosure may be configured to interface with a nerve tree 15 (in this example shown running adjacent to a vessel 14). Based on monitoring and/or stimulation and sensing information, the surgical tool 1710 may be directed 1720 along the nerve structure 15 to better target an overactive nerve. Such a configuration may be advantageous for tracking an overactive nerve along an organ, a vessel, etc. in order to find a more ideal location at which to ablate it. In the non-limiting example shown, a more distal location may be ideal for the ablation procedure, as less damage may be caused to surrounding nerves in the nerve bundle. Other relevant methods are highlighted throughout the present disclosure and may become apparent through reading of the present disclosure.

The surgical tool 1710 may be arranged in accordance with the present disclosure. In aspects, the surgical tool 1710 may include one or more sensing tips arranged at the tip thereof, one or more of the sensing tips interconnected 1725 with a controller, a microcircuit, an interconnect, an operator, etc.

Figure 18:
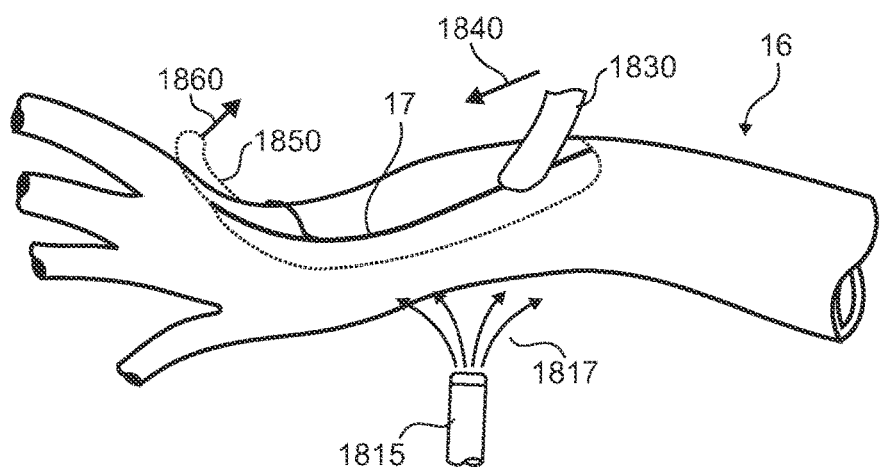
FIG. 18 shows aspects of systems for visualizing target tissues in accordance with the present disclosure.

FIG. 18 shows aspects of systems for visualizing target tissues in accordance with the present disclosure. The figure illustrates a spray type delivery tool 1815, where the medium is provided in a vehicle suitable for spraying 1817 onto an anatomical site 16 within the body. The molecular binding species in the medium may bind to the target tissues 17 (in this case a nerve tissue). The spray delivery tool 1815 may include a light source (e.g. a blue light, an ultraviolet light, etc.) for facilitating rapid curing of the medium after it has been sprayed on to the target tissues. The medium may include a visualization aspect, a gelling aspect (i.e. a radial cross linking or click crosslinking hydrogel, etc.), or the like.

FIG. 18 also shows a touch based applicator 1830 configured to rub 1840 a visualization medium 1850 (i.e. a medium including one or more molecular binding species, one or more visualization aids, visual marking moieties, etc.) in accordance with the present disclosure onto a target anatomy 16. The applicator 1830 may include means for curing the visualization medium 1850 in place, once it has been applied to the tissues.

FIG. 18 also shows a technique for removing a post cured visualization medium 1850 in accordance with the present disclosure. Once cured, the visualization medium may be physically picked up 1860 (i.e. by a vacuum tool, a clamp, a gripper, an adhesive tool, etc.) for removal from the body. In the non-limiting example shown, a gripper based removal tool may be shown peeling a post cured visualization medium 1850 off of the adjacent tissues for subsequent removal from the body.

Figures 19A, 19B:
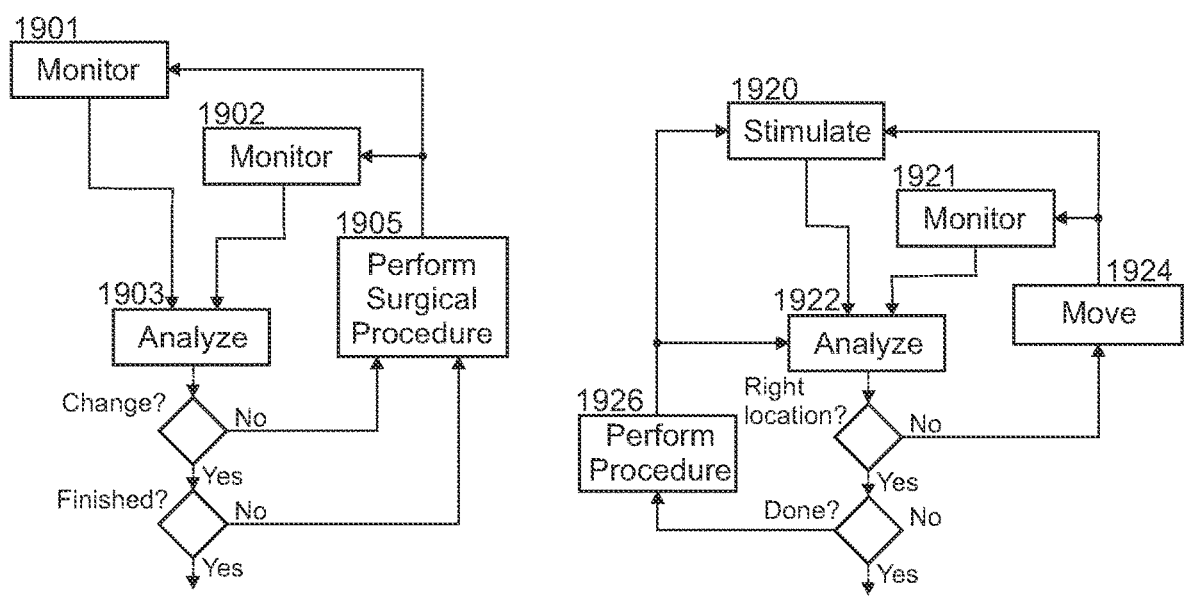
FIGS. 19a-b show methods for performing aspects of a surgical procedure in accordance with the present disclosure.

FIGS. 19a-b show methods for performing aspects of a surgical procedure in accordance with the present disclosure. FIG. 19a shows aspects of a surgical procedure including monitoring 1901 a physiological signal at a first monitoring location (e.g. on an organ, on the wall of a vessel, etc.) to generate a first signal set, and monitoring 1902 a physiological signal at a second monitoring location (e.g. on the organ, on the wall of the vessel, elsewhere in the body, etc.) and/or the first monitoring location to generate a second signal set. The method includes analyzing 1903 the signal sets to generate a result (e.g. a difference between the signal sets, a change in a set compared with a previous result, a patient population, etc.). The result may be compared with predetermined criteria to determine if a procedure 1905 should be performed or not. The procedure 1905 may be a surgical procedure, at least a portion of an ablation, stimulation, further monitoring, etc. The first comparison may be used to determine if the surgical procedure is having the intended effect on the tissues. The method may include another comparison to determine if the overall procedure is finished or not finished. In the case that the overall procedure is finished the method may include moving to another surgical site, stimulating an alternative tissue site, cleanup and/or removal of a surgical tool from the body, or the like. In the case that the procedure is not finished an additional procedure 1905 may be performed.

One or more aspects of the method may be performed with a surgical tool in accordance with the present disclosure.

FIG. 19b shows a method for locating a surgical location on a body and performing a surgical procedure thereupon. The method may include stimulating 1920 a tissue location; monitoring 1921 one or more physiological parameters at the tissue location or another location in the body; analyzing 1922 the stimulation 1920 and/or the monitoring 1921 processes to generate a result set (e.g. one or more parameters determined from the data sets associated with either the stimulation 1920, and/or the monitoring 1921, etc.). The method may include assessing the result set to decide if the location is suitable for performing a surgical procedure, if it is not then the system may move 1924 and/or assess an alternative location in the body. If the location is suitable for a surgical procedure then the method may include performing 1926 at least a portion of a surgical procedure thereupon and potentially repeat the overall process. The method may include determining from the result set if the surgical procedure has been completed, if so finalize the procedure, if not perform another procedure 1926 and/or move 1924 to a new location.

The method may include moving to another surgical site, stimulating an alternative tissue site, cleanup and/or removal of a surgical tool from the body, or the like.

One or more aspects of the method may be performed with a surgical tool in accordance with the present disclosure.

The method may include performing at least part of a surgical procedure (e.g. ablation, chemical delivery, etc.), and monitoring at a location (i.e. the first location, an alternative location, etc.) to determine if the surgical procedure was successful.

Figure 20A:
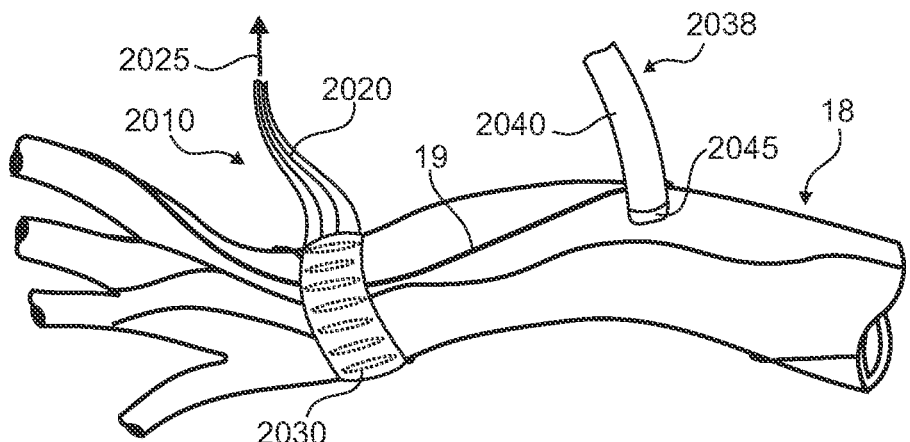
FIGS. 20a-c show aspects of a surgical tool in accordance with the present disclosure.
Figure 20B:
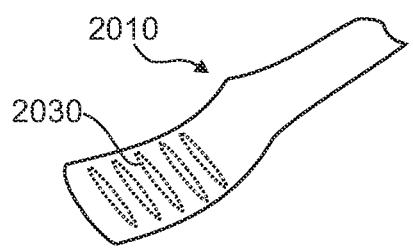
Figure 20C:
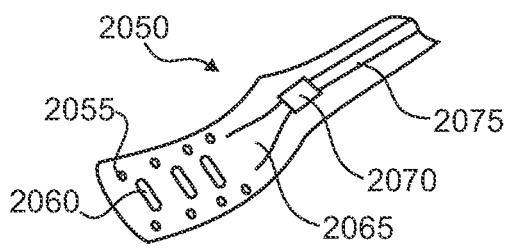

FIGS. 20a-c shows aspects of a surgical tool system in accordance with the present disclosure. The surgical system includes an endoscopic tool 2010 in accordance with the present disclosure with a control arm 2020 and a tissue interfacing tool 2030 including one or more sensing tips each in accordance with the present disclosure. The surgical system includes an optional stimulating probe 2038, configured to interface with a tissue site elsewhere on an anatomical point of interest 18 (e.g. as shown a renal artery or a nerve plexus 19). The stimulating probe 2038 may include an electrode 2045 (for electrically interfacing with a tissue site) and an insulator 2040 (for substantially isolating the probe from surrounding tissues). The stimulating probe 2038 and the endoscopic tool 2010 may be used in conjunction to perform a surgical procedure in accordance with the present disclosure. In aspects, the tissue interfacing tool 2030 may be electrically interconnected 2025 with a controller, a microcircuit, an operator, an interconnect, etc.

FIG. 20b shows aspects of a non-limiting example of a tissue interfacing tool 2010 in accordance with the present disclosure. The tool 2010 includes a row of electrode elements 2030 arranged so as to cover at least a portion of an adjacent vessel during use (optionally in a circumferential direction, a longitudinal direction, etc.). Other aspects of such tools are discussed elsewhere in the present disclosure.

FIG. 20c show aspects of a non-limiting example of a tissue interfacing tool 2050 in accordance with the present disclosure. The tool 2050 includes multiple rows of electrode elements 2055, 2060 arranged so as to cover at least a portion of an adjacent vessel during use (optionally in a circumferential direction, a longitudinal direction, etc.). Other aspects of such tools are discussed elsewhere in the present disclosure.

The interfacing tool 2050 includes a local control circuit 2070 in accordance with the present disclosure. In this non-limiting example, the local control circuit 2070 is configured to multiplex, pre-amplify, and/or digitize signals obtained 2065 from one or more electrodes 2055, 2060 on the tissue interfacing tool 2050 and to communicate 2075 with an external controller, interconnect, operator, etc. during use.

Figure 21A:
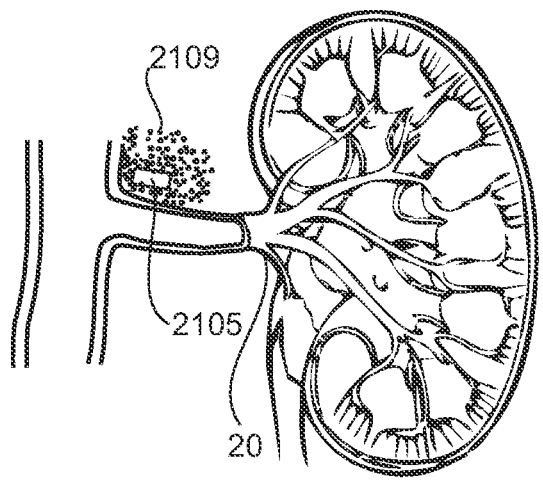
FIGS. 21a-b show aspects of an implantable device for sustained release of a neuromodulating substance in accordance with the present disclosure.
Figure 21B:
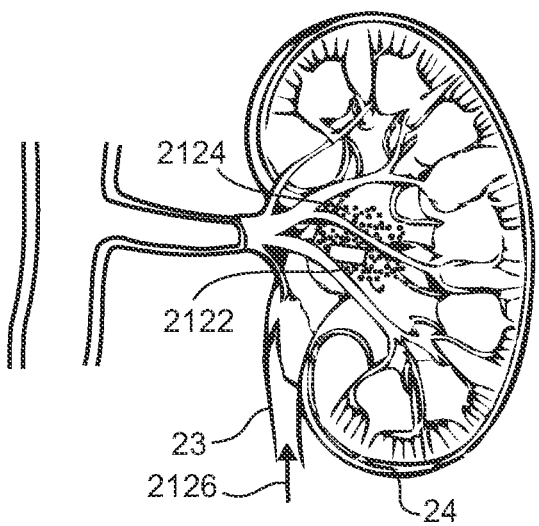

FIGS. 21a-b show aspects of an implantable device for sustained release of a neuromodulating substance in accordance with the present disclosure. FIG. 21a shows an implantable device 2105 placed in the vicinity of a renal artery 20 as part of a procedure in accordance with the present disclosure (i.e. as part of a denervation procedure). In aspects, such an implantable device 2105 may be placed by a surgical tool in accordance with the present disclosure. In aspects, the implantable device 2105 may include a neuromodulating substance 2109, perhaps confined in a retaining medium (i.e. a hydrogel matrix, etc.) and may leach into the surrounding tissues over time, after placement during a surgical procedure. In aspects, the neuromodulating substance may be a potent denervating agent (i.e. a neurotoxin, a botulinum toxin, a tetrodotoxin, a tetraethylammonium, a chlorotoxin, a curare, a conotoxin, a bungarotoxin, arsenic, ammonia, ethanol, hexane, nitric oxide, glutamate, resiniferatoxin, alchohol, phenol, etc.), a neuroblocking agent (capaicin, an anesthetic, lidocaine, tetanus toxin, quaternary ammonium salts, a pachycurare, a leptocurare, acetylcholine, aminosteroids, etc.).

In aspects, the implantable device 2105 may be injected into the body and cross-linked in place in order to form the final structure. The retaining medium may be configured so as to crosslink via a radial polymerization procedure (i.e. photopolymerization), a click polymerization procedure (i.e. an oxime click chemistry based hydrogel), or the like. Such form-in-place hydrogels known in the art of bioscaffold formation and bioadhesives may be adapted for use in this application.

In aspects, the retaining medium may be configured with one or more biodegradable aspects, such that over time (i.e. in a controlled fashion), the retaining medium may breakdown and further neuromodulating substance may be released into the surrounding tissues.

FIG. 21b shows an implantable device 2124 including a neuromodulating substance 2122 in accordance with the present disclosure placed within the renal pelvis of a kidney 24. In aspects, the implantable device 2124 may have been placed 2126, injected, or formed in place via access through the ureter 23, through the wall of the kidney 24, etc. In aspects, the implantable device 2124 may be formed with a shape (i.e. a cage, a horned shape, etc.) so as to improve retention of the implanted device within the renal pelvis of the kidney 24. The implantable device 2124 may include a retaining medium in accordance with the present disclosure for providing a controlled release of the neuromodulating substance into the renal pelvis of the kidney 24.

In aspects, the implantable devices discussed in FIGS. 21a,b may be combined with the implantable devices discussed in FIGS. 14, 15a,b, 22, etc. in order to provide a means for monitoring the effect of the neuromodulating substance over time, for following up on a surgical procedure, etc.

Figure 22:
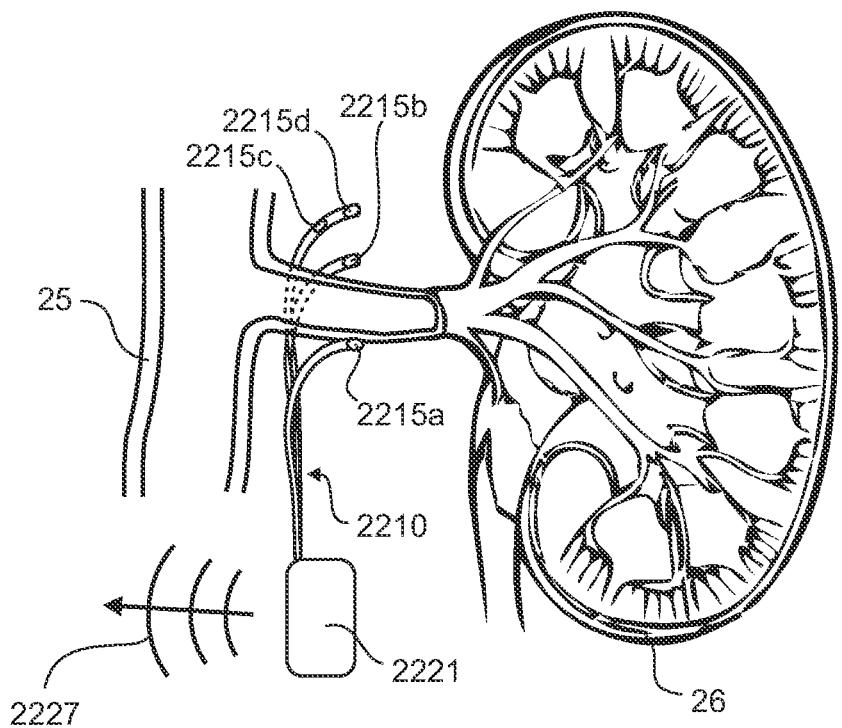
FIG. 22 shows aspects of an implantable device for monitoring and/or modulating neural activity in accordance with the present disclosure.

FIG. 22 shows aspects of an implantable device for monitoring and/or modulating neural activity in accordance with the present disclosure. The implantable device includes one or more microfingers 2210 each in accordance with the present disclosure. Each microfinger includes one or more sensing tips 2215a-d configured so as to monitor one or physical or physiological parameters in the vicinity thereof during a surgical procedure, or following a surgical procedure. The implantable device is shown positioned near to a renal artery 25, so as to monitor and/or modulate neurological function of the kidney 26 or communication between the kidney 26 and other neurological structures within the body via the renal plexus.

The implantable device includes a housing 2221 including one or more microcircuits configured to monitor signals at the sensing tips 2215a-d, to perform signal conditioning, and to communicate 2227 with an outside reader, controller, operating device, etc. The housing may further include a power source such as a battery, a biofuel cell (i.e. a glucose biofuel cell), or an energy harvesting subsystem so as to capture kinetic energy, energy from an incident RF signal, or the like.

The implantable device may be configured to monitor neural activity and/or physiological information for a period of time following a surgical procedure (i.e. days, weeks, months, indefinitely) following such a procedure. In aspects, the implantable device may perform additional neuromodulation procedures (i.e. RF ablation procedures) in the case that the neural activity returns to an abnormal state, etc. In aspects, the power supply may be configured to store sufficient amounts of energy such that the RF ablation procedure may be performed without external interconnection. Between procedures, the power supply may be recharged, for example via a wireless recharging system, or the like.

Figure 23:
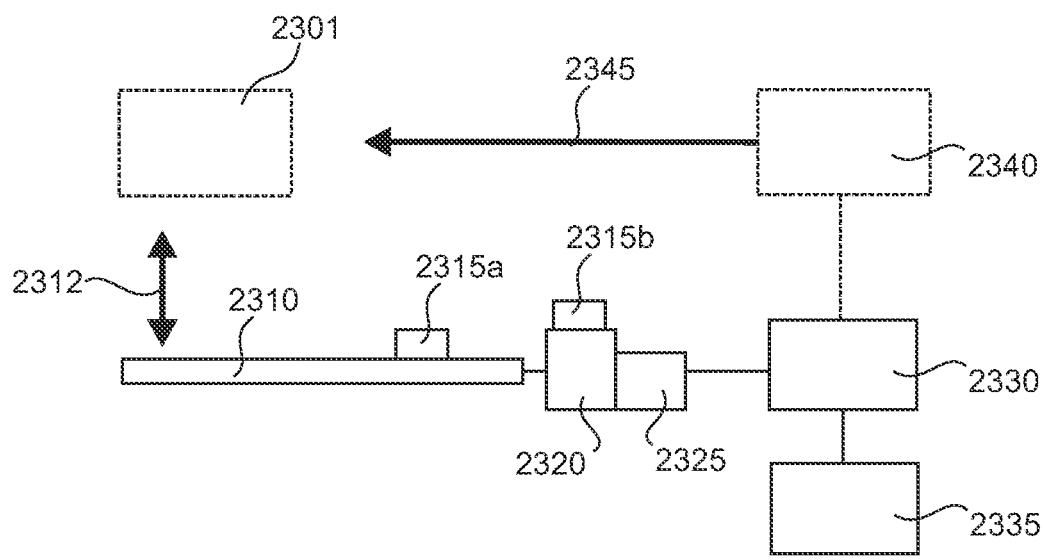
FIG. 23 shows aspects of a system for performing a surgical procedure in accordance with the present disclosure.

FIG. 23 shows aspects of a system for performing a surgical procedure in accordance with the present disclosure. The system is shown interfacing with a surgical site 2301 within a body, a subject, a patient, etc. The system includes a microsurgical tool 2310 in accordance with the present disclosure. During use, the microsurgical tool 2310 is configured to interact 2312 with the surgical site 2301 in accordance with the present disclosure. In aspects, the microsurgical tool 2310 may be coupled to a connector 2320, the connector providing a mechanical and electrical interface between the microsurgical tool 2310 and one or more other modules of the system. In aspects, the microsurgical tool may include an embedded local control circuit 2315a (a microcircuit, a switch network, a signal conditioning circuit, etc.) in accordance with the present disclosure. In aspects, the connector 2320 may include a local control circuit 2315b in accordance with the present disclosure. In aspects, the connector 2320 may be coupled to an operator input device 2325 (i.e. a foot pedal, an advancing slider, a torqueing mechanism, a recording button, an ablation button, etc.). In aspects, the connector 2320 may be coupled to a control unit 2330 configured to accept one or more signals from the microsurgical tool 2310, communicate one or more control signals thereto, send one or more pulsatile and/or radio frequency signals to the microcontroller, record one or more electrophysiological signals from the microsurgical tool, or the like.

In aspects, the control unit 2330 may be connected to a display 2335 configured to present one or more aspects of the recorded signals from the microsurgical tool to an operator, to present a map, at least partially dependent on the recorded signals, etc.

In aspects, the control unit 2330 may be coupled to a surgical subsystem 2340, the surgical subsystem 2340 configured to perform a surgical procedure 2345 to the surgical site 2301. Some non-limiting examples of suitable surgical procedures include an ablation, a cryoablation, an excision, a cut, a burn, a radio frequency ablation, radiosurgery, an ultrasonic ablation, an abrasion, a biopsy, and delivery of a substance (i.e. a neuromodulating substance in accordance with the present disclosure). The control unit 2330 may be configured to influence, direct, control, and/or provide feedback for one or more aspects of the surgical procedure 2340, based upon one or more of the electrophysiological signals conveyed by the microsurgical tool 2310.

Some non-limiting methods for performing a surgical procedure in accordance with the present disclosure are discussed herein.

In aspects, a method for addressing a surgical site on an organ in a body (e.g. a bowel wall, a stomach, a kidney, a gland, an artery, a vein, a renal artery, a kidney, a spleen, a pancreas, a prostate, a bladder, etc.) is considered. The method includes, monitoring one or more local physiological signals (e.g. an evoked potential, a neurological activity, MSNA, EMG, MMG, sympathetic tonal change, etc.) in accordance with the present disclosure at one or more measurement locations along an outer wall of the organ to determine one or more reference signals; performing at least a portion of a surgical procedure (e.g. an ablation, an excision, a cryoablation, a cut, a burn, an RF ablation, an abrasion, a radiosurgical procedure, a biopsy, delivery of a substance, etc.) in accordance with the present disclosure at or near to one or more surgical locations (e.g. proximal, distal, remotely therefrom, and/or collocated with one or more of the measurement locations); monitoring one or more local physiological signals at one or more of the measurement locations to determine one or more updated signals; and comparing one or more reference signals with one or more updated signals to determine an extent of completion for the surgical procedure.

In aspects, the extent of completion may include a change, reduction and/or substantial elimination of at least a portion of one or more of the local physiological signals (e.g. reduction in amplitude of a frequency band, reduction in responsiveness, a change in a lag between measurement locations, a change in cross-talk between measurement locations, substantial elimination of the signal, etc.)

In aspects, the extent of completion may include measuring a change in coherence between two or more signals obtained from sites affected by the surgical procedure (i.e. from a first site distal to where the surgical procedure was performed, and from a second site proximal to where the surgical procedure was performed).

In aspects, the procedure may be to perform a temporary neurological block. In this aspect, the method may be used to separate afferent and efferent traffic from either side of the temporary block, for further analysis, diagnosis of disease, evaluation of neurological activity, or the like. In aspects, a temporary block may be followed by a more permanent block if the analysis demonstrates that such a substantially permanent block would be warranted.

The step of monitoring to determine an updated signal may be performed before, during, and/or after the step of performing at least a portion of the surgical procedure. In aspects, monitoring, stimulation, and ablation may be performed in succession and/or in parallel.

In aspects, the method may include sweeping one or more electrodes over the lumen wall while monitoring, stimulating, and/or ablating the surface thereof. In aspects, simultaneous monitoring and sweeping may be used to generate a map of neurological activity along the lumen wall.

The step of performing at least a portion of the surgical procedure may be repeated. Thus the method may be incrementally applied, so as to head towards completion in a stepwise process without excessive application of the surgical procedure.

The method may include waiting after performing at least a portion of the surgical procedure. Monitoring may be performed during the waiting procedure, perhaps so as to determine a recovery period for the local physiological signal (i.e. a time period over which the local physiological signal recovers). Such a recovery period may be an indication of the extent of completion.

In aspects, the method may include stimulating one or more stimulation locations (proximal, distal, remotely therefrom, and/or collocated with one or more of the measurement locations and/or the surgical locations). The step of stimulating may be coordinated with the step of performing at least a portion of the surgical procedure, and/or with the step of monitoring to determine a reference and/or updated signal. The stimulation may be provided in any form in accordance with the present disclosure. In aspects, the stimulation may include one or more current pulses, one or more voltage pulses, combinations thereof, or the like. The step of stimulation may be advantageous for assessing the updated signal at one or more measurement locations and/or between two or more measurement locations in the presence of background noise and/or local physiological activity.

In aspects, the method may include monitoring one or more remote physiological parameters in accordance with the present disclosure at a remote location (e.g. in the vicinity of an alternative vessel, an organ, a ganglion, a nerve, etc.) substantially removed from the immediate vicinity of the surgical site to determine an updated remote physiological signal and/or reference remote physiological signal.

Some non-limiting examples of remote physiological parameters that may be monitored include water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive (e.g. bursts per minute, bursts per heartbeat, etc.), tissue tone, blood flow (e.g. through an artery, through a renal artery), a blood flow differential signal (e.g. a significantly abnormal and or sudden change in blood flow within a structure of the body, a vessel, an organ, etc.), blood perfusion (e.g. to an organ, an eye, etc.), a blood analyte level (e.g. a hormone concentration, norepinephrine, catecholamine, renine, angiotensin II, an ion concentration, a water level, an oxygen level, etc.), nerve traffic (e.g. post ganglionic nerve traffic in the peroneal nerve, celiac ganglion, superior mesenteric ganglion, aorticorenal ganglion, renal ganglion, and/or related nervous system structures), combinations thereof, and the like.

The updated remote physiological signal and/or reference remote physiological signal may be combined and/or compared with one or more reference signals, and/or one or more updated signals in order to determine the extent of completion, as part of a decision making process, and/or as part of a surgical control system (i.e. so as to determine whether to continue with, stop, or alter the surgical procedure).

The method may include selecting a surgical location. The step of selection may depend upon one or more monitoring steps, proximity to an alternative surgical location (i.e. perhaps a previously treated surgical location, etc.).

In aspects, the method may include sweeping the lumen and/or wall of a vessel while monitoring in order to localize one or more anatomical sites of interest, one or more regions of abnormal activity, etc.

In aspects, the steps of monitoring may be completed sequentially. Alternatively, additionally, or in combination, the steps of monitoring may be effectively continuously applied through the procedure. The comparison may be made using one or more data points obtained from one or more steps of monitoring. The comparison may be made via algorithmic combination of one or more measurements.

In aspects, the step of monitoring may be used to extract one or more electrophysiological parameters during a first period and monitoring an applied field (i.e. as caused by a stimulation and/or ablation event) during a second period.

In aspects, the method may include generating a topographical map from the one or more measurements (e.g. from one or more of the signals). The method may include determining a topographical map of physiological functionality in the vicinity of the surgical site derived from one or more of the physiological signals. The method may include updating the topographical map after the step of performing at least a portion of the surgical procedure. The method may include generating the map during a sweeping process (i.e. a longitudinal sweep, a circumferential sweep, a helical sweep, etc.).

In aspects, the method may include placement of a plurality of surgical tools, one or more surgical tools (i.e. a procedural tool) placed so as to access one or more of the surgical locations, and one or more surgical tools (i.e. a monitoring tool) placed so as to access one or more of the monitoring locations. In one non-limiting example, a procedural tool may be placed upon a first organ (e.g. a bowel wall, a stomach wall, a kidney, a gland, a renal artery, a left renal artery, etc.) and a monitoring tool may be placed upon a second organ (e.g. an opposing renal artery, a right renal artery, a femoral artery, an iliac artery, etc.). Thus, the monitoring tool may be used to monitor one or more of the measurement locations on the second organ. The procedural tool may be used to surgically treat one or more surgical locations on the first organ. Additionally, alternatively, or in combination, the procedural tool may monitor one or more monitoring locations on the first organ, perhaps in combination with monitoring performed on the second organ by the monitoring tool.

In aspects, the method may be performed with one or more surgical tools in accordance with the present disclosure.

One or more steps of monitoring may be performed with one or more sensing tips in accordance with the present disclosure.

One or more steps of performing at least a portion of the surgical procedure may be performed with one or more sensing tips in accordance with the present disclosure.

In one non-limiting example of a method for RF ablating tissue, the local tissue tone may be measured before, during, between individual RF pulses, and/or after a train of RF pulses. As the local tissue tone changes during application of the RF pulses, the tonal changes may be used to determine the extent of the therapy. As the RF ablation process is applied to the adjacent tissues (perhaps via one or more sensing tips), the tonal measurements (as determined by one or more sensing tips, perhaps the same tip through which the RF signal may be applied) may be monitored to determine an extent of completion of the procedure. Such an approach may be advantageous as the tonal measurement techniques may not be significantly affected by the local RF currents associated with the RF ablation procedure.

In aspects, an interventionalist/proceduralist may insert a catheter in accordance with the present disclosure into the aorta from either the superior or inferior approach (brachial or femoral arteries) and selectively cannulate the renal artery. In aspects, a guiding catheter may be used for this purpose. In aspects, a microsurgical tool in accordance with the present disclosure may be placed through the guiding catheter.

In aspects, an interventionalist/proceduralist may insert a surgical tool in accordance with the present disclosure via a percutaneous approach, perhaps under guidance with a visualization aid (i.e. ultrasound guidance, radiosurgical guidance, etc.). In aspects, a combination of vascular and percutaneous approaches may be coordinated (i.e. in the case of multi-tool procedures).

In aspects, the electrodes may be made to puncture the vessel wall. The electrodes may be forced to cause penetration of one or more of the electrodes into the intima, media, or adventitia of the vessel wall (i.e. artery, vein, etc.) to be measured. In aspects, one or more electrodes may be configured for microscopic or macroscopic spatial recording. Following a suitable period of recording, the device may be withdrawn into the guiding catheter and removed from the body.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A microsurgical tool comprising:
a control arm; and
a tissue interfacing tool coupled to the control arm;
the tissue interfacing tool comprising:
a plurality of sensing tips; and
one or more actuating elements;
wherein the one or more actuating elements are configured to wrap at least a portion of the tissue interfacing tool around a tissue structure in response to control signaling provided via the control arm; and
wherein at least one of the plurality of sensing tips is configured for ablating at least a portion of the tissue structure in response to the control signaling provided via the control arm.

2. The microsurgical tool in accordance with claim 1, wherein the plurality of sensing tips comprises a plurality of electrodes.

3. The microsurgical tool in accordance with claim 2, wherein the plurality of electrodes are arranged in one or more rows that cover at least a portion of the tissue structure when the one or more actuating elements wrap said at least a portion of the tissue interfacing tool around the tissue structure.

4. The microsurgical tool in accordance with claim 3, wherein the one or more rows of electrodes are arranged to cover said at least a portion of the tissue structure in a circumferential direction when the one or more actuating elements wrap said at least a portion of the tissue interface tool around the tissue structure.

5. The microsurgical tool in accordance with claim 3, wherein the one or more rows of electrodes are arranged to cover said at least a portion of the tissue structure in a longitudinal direction when the one or more actuating elements wrap said at least a portion of the tissue interface tool around the tissue structure.

6. The microsurgical tool in accordance with claim 2, wherein the plurality of electrodes are arranged in two or more rows that cover at least a portion of the tissue structure when the one or more actuating elements wrap said at least a portion of the tissue interfacing tool around the tissue structure.

7. The microsurgical tool in accordance with claim 6, wherein a first one of the two or more rows comprise ablating electrodes and at least a second one of the two or more rows comprise sensing electrodes.

8. The microsurgical tool in accordance with claim 6, wherein the two or more rows comprise a first row of ablating electrodes and second and third rows of sensing electrodes on first and second sides of the ablating electrodes.

9. The microsurgical tool in accordance with claim 1, wherein the tissue interfacing tool further comprises a local control circuit.

10. The microsurgical tool in accordance with claim 9, wherein the local control circuit is configured to condition one or more electrophysiological signals obtained from one or more of the plurality of sensing tips prior to conveying the one or more electrophysiological signals to the control arm.

11. The microsurgical tool in accordance with claim 10, wherein conditioning the one or more electrophysiological signals prior to conveying the one or more electrophysiological signals to the control arm comprises one or more of pre-amplification, radio frequency (RF) signal routing, analog to digital conversion, signal buffering, signal isolation, multiplexing and demultiplexing functions, and communication with externally located hardware.

12. The microsurgical tool in accordance with claim 1, further comprising a stimulating probe.

13. The microsurgical tool in accordance with claim 12, wherein the stimulating probe is configured to interface with an additional tissue site.

14. The microsurgical tool in accordance with claim 13, wherein the stimulating probe comprises one or more electrodes for interfacing with the additional tissue site.

15. The microsurgical tool in accordance with claim 14, wherein the stimulating probe further comprises an insulator that isolates the stimulating probe from surrounding tissues.

16. The microsurgical tool in accordance with claim 1, wherein at least one of the plurality of sensing tips comprises one or more stimulating electrodes configured to provide an ablating current to adjacent tissues.

17. The microsurgical tool in accordance with claim 1, wherein at least one of the one or more actuating elements comprises an electroactive material actuator comprising an active material configured to change shape upon command.

18. The microsurgical tool in accordance with claim 17, wherein the active material comprises one or more of a shape memory material, an electroactive polymer and a piezoceramic material.

19. A system comprising:
a microsurgical tool comprising a control arm and a tissue interfacing tool coupled to the control arm, the tissue interfacing tool comprising a plurality of sensing tips and one or more actuating elements; and
a controller coupled to the microsurgical tool, the controller being configured to provide control signaling to the control arm of the microsurgical tool, the control signaling comprising instructions for directing the one or more actuating elements to wrap at least a portion of the tissue interfacing tool around a tissue structure and for directing at least one of the plurality of sensing tips to ablate at least a portion of the tissue structure.

20. The system in accordance with claim 19, wherein the microsurgical tool further comprises a stimulating probe configured to interface with an additional tissue site.

* * * * *